(12) United States Patent
Zion et al.

(10) Patent No.: US 8,603,529 B2
(45) Date of Patent: *Dec. 10, 2013

(54) POLYNUCLEOTIDE APTAMER-BASED CROSS-LINKED MATERIALS AND USES THEREOF

(75) Inventors: Todd C. Zion, Marblehead, MA (US); Thomas M. Lancaster, Stoneham, MA (US)

(73) Assignee: Smartcells, Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/145,531

(22) PCT Filed: Jan. 27, 2010

(86) PCT No.: PCT/US2010/022237
§ 371 (c)(1),
(2), (4) Date: Jul. 20, 2011

(87) PCT Pub. No.: WO2010/088276
PCT Pub. Date: Aug. 5, 2010

(65) Prior Publication Data
US 2011/0281939 A1    Nov. 17, 2011

Related U.S. Application Data

(60) Provisional application No. 61/147,878, filed on Jan. 28, 2009, provisional application No. 61/159,643, filed on Mar. 12, 2009, provisional application No. 61/162,092, filed on Mar. 20, 2009, provisional application No. 61/162,053, filed on Mar. 20, 2009, provisional application No. 61/162,107, filed on Mar. 20, 2009, provisional application No. 61/162,105, filed on Mar. 20, 2009, provisional application No. 61/163,084, filed on Mar. 25, 2009, provisional application No. 61/219,897, filed on Jun. 24, 2009, provisional application No. 61/223,572, filed on Jul. 7, 2009, provisional application No. 61/252,857, filed on Oct. 19, 2009.

(51) Int. Cl.
*A61K 9/14*      (2006.01)
*A61K 38/28*     (2006.01)
*C07H 21/04*     (2006.01)

(52) U.S. Cl.
USPC ........... 424/486; 536/23.1; 530/303; 514/5.9; 514/6.8

(58) Field of Classification Search
None
See application file for complete search history.

(56) References Cited

U.S. PATENT DOCUMENTS

| | | | |
|---|---|---|---|
| 5,994,517 A | 11/1999 | Tso et al. | |
| 7,935,683 B2 * | 5/2011 | Mizu et al. | 514/54 |
| 2002/0068295 A1 * | 6/2002 | Madou et al. | 435/6 |
| 2004/0123343 A1 | 6/2004 | La Rosa et al. | |
| 2007/0099820 A1 * | 5/2007 | Lancaster et al. | 514/3 |

FOREIGN PATENT DOCUMENTS

| WO | WO-2005/106035 | 11/2005 |
|---|---|---|
| WO | WO-2008/016356 | 2/2008 |

OTHER PUBLICATIONS

International Search Report and Written Opinion for PCT/US10/22237, mailed on Dec. 1, 2010.
Lindhorst et al. Trivalent alpha-D-mannoside clusters as inhibitors of type-1 fimbriae-mediated adhesion of *Escherichia coli*: structural variation and biotinylation. J. Chem. Soc. Perkin Trans 1:823-831 (2001).

* cited by examiner

*Primary Examiner* — Richard Schnizer
(74) *Attorney, Agent, or Firm* — John David Reilly; Immac J. Thampoe

(57) ABSTRACT

In one aspect, the disclosure provides cross-linked materials that include multivalent polynucleotide aptamers that bind a target molecule; and conjugates that include two or more separate affinity ligands bound to a conjugate framework, wherein the two or more affinity ligands compete with the target molecule for binding with the aptamers and wherein conjugates are cross-linked within the material as a result of non-covalent interactions between aptamers and affinity ligands on different conjugates. These materials are designed to release amounts of conjugate in response to desired concentrations of the target molecule. Depending on the end application, in various embodiments, the conjugates may also include a drug and/or a detectable label. The drug, detectable label and affinity ligands may be covalently or non-covalently bound to the conjugate framework.

11 Claims, 6 Drawing Sheets

| Sequence | SEQ ID NO. |
|---|---|
| GGGAGUCGACCGACCAGAAUUAUGUGCGUCUACAUCUAGACUCAU------------------------------------------------- | 1 |
| GGGAGUCGACCGACCAGAAUUAUCUGCGUGU-UAUCUUCAAUCAUUAACAGUACACUUAAUAUGUGCGUCUACAUCUAGACUCAU | 2 |
| GGGAGUCGACCGACCAGAAUUAUCUGCGUGU-UAUCCCCAAUCAUUAACAGUACACUUAAUAUGUGCGUCUACAUCUAGACUCAU | 3 |
| GGGAGUCGACCGACCAGAAUUAUCUGCGUGU-UAUCCCCAGUCAUUAACAGUACACUUAAUAUGUGCGUCUACAUCUAGACUCAU | 7 |
| GGGAGUCGACCGACCAGAAUUAUCCGCGUGU-UAUCCCCAGUCAUUAACAGUACACUUAAUAUGUGCGUCUACAUCUAGACUCAU | 5 |
| GGGAGUCGACCGACCAGAAUACAGUACGGGG-GUGAUCACCAAUGCUGAAGCGUAUGCGUCUACAUCUAGACUCAU | 4 |
| GGGAGUCGACCGACCAGAAGUCAGGAUAGGU-GCAAGAAUGCGAAAUUCGCAGGCUGGUGUAUGCGUCUACAUCUAGACUCAU | 6 |

Figure 2

SEQUENCE LISTING

```
<160> NUMBER OF SEQ ID NOS: 12

<210> SEQ ID NO 1
<211> LENGTH: 45
<212> TYPE: DNA
<213> ORGANISM: Artificial Sequence
<220> FEATURE:
<223> OTHER INFORMATION: Monoclonal aptamer

<400> SEQUENCE: 1
gggagucgac cgaccagaau uaugugcguc uacaucuaga cucau            45

<210> SEQ ID NO 2
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 2
gggagucgac cgaccagaau uaucugcgug uuaucuucaa ucauuaacag uacacuuaau    60
augugcgucu acaucuagac ucau                                           84

<210> SEQ ID NO 3
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 3
gggagucgac cgaccagaau uaucugcgug uuaucccaa ucauuaacag uacacuuaau     60
augugcgucu acaucuagac ucau                                           84

<210> SEQ ID NO 4
<211> LENGTH: 84
<212> TYPE: DNA
<213> ORGANISM: Artificial Sequence
<220> FEATURE:
```

```
<223> OTHER INFORMATION: Monoclonal aptamer

<400> SEQUENCE: 4
gggagucgac cgaccagaau acaguacggg ggugaucacc aaugcugaau gcagaagcgu      60
augugcgucu acaucuagac ucau                                            84

<210> SEQ ID NO 5
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 5
gggagucgac cgaccagaau uauccgcgug uuauccccaa ucauuaacag uacacuuaau      60
augugcgucu acaucuagac ucau                                            84

<210> SEQ ID NO 6
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 6
gggagucgac cgaccagaag ucaggauagg ugcaagaaug cgaaauucgc aggcuggugu      60
augugcgucu acaucuagac ucau                                            84

<210> SEQ ID NO 7
<211> LENGTH: 84
<212> TYPE: DNA
<213> ORGANISM: Artificial Sequence
<220> FEATURE:
<223> OTHER INFORMATION: Monoclonal aptamer

<400> SEQUENCE: 7
gggagucgac cgaccagaau uaucugcgug uuauccccag ucauuaacag uacacuuaau      60
augugcgucu acaucuagac ucau                                            84

<210> SEQ ID NO 8
<211> LENGTH: 40
<212> TYPE: DNA
<213> ORGANISM: Artificial Sequence
<220> FEATURE:
<223> OTHER INFORMATION: Consensus aptamer sequence
<220> FEATURE:
<221> NAME/KEY: misc_feature
<222> LOCATION: (1)..(1)
<223> OTHER INFORMATION: t/u
<220> FEATURE:
<221> NAME/KEY: misc_feature
<222> LOCATION: (2)..(2)
<223> OTHER INFORMATION: t/u
<220> FEATURE:
<221> NAME/KEY: misc_feature
<222> LOCATION: (4)..(4)
<223> OTHER INFORMATION: t/u
<220> FEATURE:
<221> NAME/KEY: misc_feature
<222> LOCATION: (10)..(10)
<223> OTHER INFORMATION: t/u
<220> FEATURE:
<221> NAME/KEY: misc_feature
<222> LOCATION: (12)..(12)
<223> OTHER INFORMATION: t/u
<220> FEATURE:
<221> NAME/KEY: misc_feature
<222> LOCATION: (13)..(13)
```

```
<223> OTHER INFORMATION: t/u
<220> FEATURE:
<221> NAME/KEY: misc_feature
<222> LOCATION: (15)..(15)
<223> OTHER INFORMATION: t/u
<220> FEATURE:
<221> NAME/KEY: misc_feature
<222> LOCATION: (22)..(22)
<223> OTHER INFORMATION: t/u
<220> FEATURE:
<221> NAME/KEY: misc_feature
<222> LOCATION: (25)..(25)
<223> OTHER INFORMATION: t/u
<220> FEATURE:
<221> NAME/KEY: misc_feature
<222> LOCATION: (26)..(26)
<223> OTHER INFORMATION: t/u
<220> FEATURE:
<221> NAME/KEY: misc_feature
<222> LOCATION: (32)..(32)
<223> OTHER INFORMATION: t/u
<220> FEATURE:
<221> NAME/KEY: misc_feature
<222> LOCATION: (37)..(37)
<223> OTHER INFORMATION: t/u
<220> FEATURE:
<221> NAME/KEY: misc_feature
<222> LOCATION: (38)..(38)
<223> OTHER INFORMATION: t/u

<400> SEQUENCE: 8
nnancygcgn gnnancyyca rncannaaca gnacacnnaa                              40

<210> SEQ ID NO 9
<211> LENGTH: 40
<212> TYPE: DNA
<213> ORGANISM: Artificial Sequence
<220> FEATURE:
<223> OTHER INFORMATION: Consensus aptamer sequence
<220> FEATURE:
<221> NAME/KEY: misc_feature
<222> LOCATION: (1)..(1)
<223> OTHER INFORMATION: t/u
<220> FEATURE:
<221> NAME/KEY: misc_feature
<222> LOCATION: (6)..(6)
<223> OTHER INFORMATION: t/u
<220> FEATURE:
<221> NAME/KEY: misc_feature
<222> LOCATION: (14)..(14)
<223> OTHER INFORMATION: t/u
<220> FEATURE:
<221> NAME/KEY: misc_feature
<222> LOCATION: (17)..(17)
<223> OTHER INFORMATION: t/u
<220> FEATURE:
<221> NAME/KEY: misc_feature
<222> LOCATION: (24)..(24)
<223> OTHER INFORMATION: t/u
<220> FEATURE:
<221> NAME/KEY: misc_feature
<222> LOCATION: (27)..(27)
<223> OTHER INFORMATION: t/u
<220> FEATURE:
<221> NAME/KEY: misc_feature
<222> LOCATION: (31)..(31)
<223> OTHER INFORMATION: t/u

<400> SEQUENCE: 9
nacagnacgg gggngancac caangcngaa ngcagaagcg                              40

<210> SEQ ID NO 10
<211> LENGTH: 40
<212> TYPE: DNA
<213> ORGANISM: Artificial Sequence
<220> FEATURE:
```

```
<223> OTHER INFORMATION: Consensus aptamer sequence
<220> FEATURE:
<221> NAME/KEY: misc_feature
<222> LOCATION: (2)..(2)
<223> OTHER INFORMATION: t/u
<220> FEATURE:
<221> NAME/KEY: misc_feature
<222> LOCATION: (8)..(8)
<223> OTHER INFORMATION: t/u
<220> FEATURE:
<221> NAME/KEY: misc_feature
<222> LOCATION: (12)..(12)
<223> OTHER INFORMATION: t/u
<220> FEATURE:
<221> NAME/KEY: misc_feature
<222> LOCATION: (20)..(20)
<223> OTHER INFORMATION: t/u
<220> FEATURE:
<221> NAME/KEY: misc_feature
<222> LOCATION: (27)..(27)
<223> OTHER INFORMATION: t/u
<220> FEATURE:
<221> NAME/KEY: misc_feature
<222> LOCATION: (28)..(28)
<223> OTHER INFORMATION: t/u
<220> FEATURE:
<221> NAME/KEY: misc_feature
<222> LOCATION: (36)..(36)
<223> OTHER INFORMATION: t/u
<220> FEATURE:
<221> NAME/KEY: misc_feature
<222> LOCATION: (39)..(39)
<223> OTHER INFORMATION: t/u

<400> SEQUENCE: 10
gncagganag gngcaagaan gcgaaanncg caggcnggng                               40

<210> SEQ ID NO 11
<211> LENGTH: 21
<212> TYPE: PRT
<213> ORGANISM: Homo sapiens

<400> SEQUENCE: 11

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 12
<211> LENGTH: 30
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

POLYNUCLEOTIDE APTAMER-BASED CROSS-LINKED MATERIALS AND USES THEREOF

RELATED APPLICATIONS

This application is a national phase application of International Application No. PCT/US2010/22237, filed Jan. 27, 2010, which claims priority to U.S. Provisional Application No. 61/147,878 filed Jan. 28, 2009, U.S. Provisional Application No. 61/159,643 filed Mar. 12, 2009, U.S. Provisional Application No. 61/162,107 filed Mar. 20, 2009, U.S. Provisional Application No. 61/162,053 filed Mar. 20, 2009, U.S. Provisional Application No. 61/162,092 filed Mar. 20, 2009, U.S. Provisional Application No. 61/162,105 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, and U.S. Provisional Application No. 61/252,857 filed Oct. 19, 2009, the content of each of which is hereby incorporated by reference in its entirety.

In accordance with 37 CFR 1.52(e)(5), a Sequence Listing in the form of a text file (entitled "Sequence listing_0038.txt," created on Jan. 25, 2010, and 5 kilobytes) is incorporated herein by reference in its entirety.

STATEMENT REGARDING FEDERALLY SPONSORED RESEARCH OR DEVELOPMENT

This invention was made with government support under Grant Numbers DK072774 and DK077292, awarded by the National Institutes of Health ("NIH"). The U.S. government has certain rights in the invention.

BACKGROUND

The majority of "controlled-release" drug delivery systems known in the prior art (e.g., U.S. Pat. No. 4,145,410 to Sears which describes drug release from capsules which are enzymatically labile) are incapable of releasing drugs at intervals and concentrations which are in direct proportion to the amount of a molecular indicator (e.g., a metabolite) present in the human body. The delivery or release of drug in these prior art systems is thus not literally "controlled," but simply a slow release which is independent of external or internal factors.

The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

In certain embodiments of the Zion system multivalent glucose-binding molecules are combined with a glycosylated polymer-insulin conjugate. The glycosylated polymer contains multiple saccharide binding groups and forms insoluble hydrogels or particles in the presence of the glucose-binding molecule. The gel releases the glycosylated polymer-insulin conjugate in response to increases in glucose concentration. The Zion system has been demonstrated using the lectin concanavalin A (Con A) as an exemplary multivalent glucose-binding molecule. Unfortunately, Con A and many of the other readily available lectins have the potential to stimulate lymphocyte proliferation. By binding to carbohydrate receptors on the surfaces of certain types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in vivo uses of lectins could be significantly diminished if an alternative multivalent glucose binding molecule could be provided. Suitable alternatives should however also be able to function as cross-linking agents within a Zion system which responds to useful concentrations of target molecule.

SUMMARY

In one aspect, the disclosure provides cross-linked materials that include multivalent polynucleotide aptamers that bind a target molecule; and conjugates that include two or more separate affinity ligands bound to a conjugate framework, wherein the two or more affinity ligands compete with the target molecule for binding with the aptamers and wherein conjugates are cross-linked within the material as a result of non-covalent interactions between aptamers and affinity ligands on different conjugates. These materials are designed to release amounts of conjugate in response to desired concentrations of the target molecule. Depending on the end application, in various embodiments, the conjugates may also include a drug and/or a detectable label. The drug, detectable label and affinity ligands may be covalently or non-covalently bound to the conjugate framework. The disclosure also provides methods of using these materials and methods of making these materials. In another aspect, the disclosure provides exemplary aptamers for use in glucose responsive materials instead of lectins such as Con A.

DEFINITIONS

Definitions of specific functional groups, chemical terms and general terms used throughout the specification are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987.

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl —As used herein, the term "arylalkyl" refers to an alkyl group substituted with an aryl group (e.g., an aromatic or heteroaromatic group).

Bivalent hydrocarbon chain —As used herein, the term "bivalent hydrocarbon chain" (also referred to as a "bivalent alkylene group") is a polymethylene group, i.e., —(CH$_2$)$_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic —As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cycloheptyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}$Ph, which may be substituted with $R^\circ$; —$(CH_2)_{0-4}O(CH_2)_{0-1}$Ph which may be substituted with $R^\circ$; —CH=CHPh, which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}$SR—, SC(S)SR$^\circ$; —$(CH_2)_{0-4}SC(O)R^\circ$; —$(CH_2)_{0-4}C(O)NR^\circ_2$; —$C(S)NR^\circ_2$; —$C(S)SR^\circ$;

—SC(S)SR°, —(CH$_2$)$_{0-4}$OC(O)NR°$_2$; —C(O)N(OR°R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —CH$_2$)$_{0-2}$OR●, —(CH$_2$)$_{0-2}$CH(OR●)$_2$; —O(haloR●), —CN, —N$_3$, (CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, —(haloR●), —OH, —OR●, —O(haloR●), —CN, —C(O)OH, —C(O)OR●, —NH$_2$, —NH$_2$, —NR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group—As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, in-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxyl protecting groups include methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Aptamer—As used herein, the term "aptamer" or "polynucleotide aptamer" refers to a polynucleotide that binds specifically to a target molecule. In general, an aptamer is said to "bind specifically" to its target molecule if it associates at a detectable level with the target molecule and does not associate detectably with unrelated molecular entities (e.g., molecules which share no common structural features with the target molecule) under similar conditions. Specific association between a target molecule and an aptamer will typically be dependent upon the presence of a particular structural feature of the target molecule such as an epitope recognized by the aptamer. Generally, if an aptamer is specific for epitope A, the presence of a molecule containing epitope A or the presence of free unlabeled epitope A in a reaction containing both free labeled epitope A and the aptamer thereto, will reduce the amount of labeled epitope A that binds to the aptamer. In general, it is to be understood that specificity need not be absolute. Indeed, it is well known in the art that aptamers may cross-react with other epitopes in addition to the target epitope. Such cross-reactivity may be acceptable depending upon the application for which the aptamer is to be used. Thus the degree of specificity of an aptamer will depend on the context in which it is being used. It is also to be understood that specificity may be evaluated in the context of additional factors such as the affinity of the aptamer for the target molecule versus the affinity of the aptamer for non-target molecules.

Biodegradable—As used herein, the term "biodegradable" refers to molecules that degrade (i.e., lose at least some of their covalent structure) under physiological or endosomal conditions. Biodegradable molecules are not necessarily hydrolytically degradable and may require enzymatic action to degrade.

Biomolecule—As used herein, the term "biomolecule" refers to molecules (e.g., polypeptides, amino acids, polynucleotides, nucleotides, polysaccharides, sugars, lipids, nucleoproteins, glycoproteins, lipoproteins, steroids, metabolites, etc.) whether naturally-occurring or artificially created (e.g., by synthetic or recombinant methods) that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Drug—As used herein, the term "drug" refers to small molecules or biomolecules that alter, inhibit, activate, or otherwise affect a biological event. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anti-coagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, patents, applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996, and the United States Pharmacopeia-25/National formulary-20, published by the United States Pharmcopeial Convention, Inc., Rockville Md., 2001. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, are all considered acceptable for use in accordance with the present invention.

Hyperbranched—As used herein, a "hyperbranched" structure is a covalent structure that includes at least one branched branch (e.g., a dendrimeric structure). A hyperbranched structure may include polymeric and/or non-polymeric substructures.

Percentage homology—As used herein, the terms "percentage homology" refer to the percentage of sequence identity between two sequences after optimal alignment as defined in the present disclosure. For example, two nucleotide sequences are said to be "identical" if the sequence of nucleotides in the two sequences is the same when aligned for maximum correspondence as described below. Sequence comparisons between two nucleotide sequences are typically performed by comparing sequences of two optimally aligned sequences over a region or "comparison window" to identify and compare regions of sequence similarity. Optimal alignment of sequences for comparison may be conducted by the local homology algorithm of Smith and Waterman, *Ad. App. Math.* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci. USA* 85:2444 (1988), by computerized implementation of these algorithms, or by visual inspection.

Percentage of sequence identity—"Percentage of sequence identity" is determined by comparing two optimally aligned sequences over a comparison window, where the portion of the nucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide residue occurs in both sequences to yield the number of matched positions, dividing the number of matched positions by the total number of positions in the window of comparison and multiplying the result by 100 to yield the percentage of sequence identity. This definition of sequence identity given above is the definition that would be used by one of ordinary skill in the art. The definition by itself does not need the help of any algorithm. The algorithms are only helpful to facilitate the optimal alignments of sequences, rather than calculate sequence identity. From this definition, it follows that there is a well defined and only one value for the sequence identity between two compared sequences which value corresponds to the value obtained for the optimal alignment.

Polymer—As used herein, a "polymer" or "polymeric structure" is a structure that includes a string of covalently bound monomers. A polymer can be made from one type of monomer or more than one type of monomer. The term "polymer" therefore encompasses copolymers, including block-copolymers in which different types of monomer are grouped separately within the overall polymer. A polymer can be linear or branched.

Polynucleotide—As used herein, a "polynucleotide" is a polymer of nucleotides. The terms "polynucleotide", "nucleic acid", and "oligonucleotide" may be used interchangeably. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl) uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Polypeptide—As used herein, a "polypeptide" is a polymer of amino acids. The terms "polypeptide", "protein", "oligopeptide", and "peptide" may be used interchangeably. Polypeptides may contain natural amino acids, non-natural amino acids (i.e., compounds that do not occur in nature but that can be incorporated into a polypeptide chain) and/or amino acid analogs as are known in the art. Also, one or more of the amino acid residues in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. These modifications may include cyclization of the peptide, the incorporation of D-amino acids, etc.

Polysaccharide—As used herein, a "polysaccharide" is a polymer of saccharides. The terms "polysaccharide", "carbohydrate", and "oligosaccharide", may be used interchangeably. The polymer may include natural saccharides (e.g., arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose) and/or modified saccharides (e.g., 2'-fluororibose, 2'-deoxyribose, and hexose). Exemplary disaccharides include sucrose, lactose, maltose, trehalose, gentiobiose, isomaltose, kojibiose, laminaribiose, mannobiose, melibiose, nigerose, rutinose, and xylobiose.

Small molecule—As used herein, the term "small molecule" refers to molecules, whether naturally-occurring or artificially created (e.g., via chemical synthesis), that have a relatively low molecular weight. Typically, small molecules are monomeric and have a molecular weight of less than about 1,500 Da.

Treat—As used herein, the term "treat" (or "treating", "treated", "treatment", etc.) refers to the administration of a material of the present disclosure to a subject in need thereof with the purpose to alleviate, relieve, alter, ameliorate, improve or affect a condition (e.g., diabetes), a symptom or symptoms of a condition (e.g., hyperglycemia), or the predisposition toward a condition.

BRIEF DESCRIPTION OF THE DRAWING

FIG. 2: shows the sequence homology of several exemplary 84 bp monoclonal aptamers as compared to monoclonal 2. Red letters differ from the original sequence.

FIG. 5: is a schematic of a cross-linked material 10 which is capable of controllably releasing conjugates 20 in response to a target molecule (e.g., glucose). The materials are prepared by combining the conjugates 20 with multivalent polynucleotide aptamers 30 that non-covalently bind the affinity ligands 40 of the conjugates 20 and thereby cross-link the conjugates 20 to form the cross-linked material 10. The non-covalent bonds between the multivalent polynucleotide aptamers 30 and the affinity ligands 40 are competitively dissociated in the presence of excess amounts of the target molecule (e.g., glucose).

DETAILED DESCRIPTION OF CERTAIN EMBODIMENTS

This application refers to a number of documents including patent and non-patent documents. The entirety of each of these documents is incorporated herein by reference.

Figure 5:
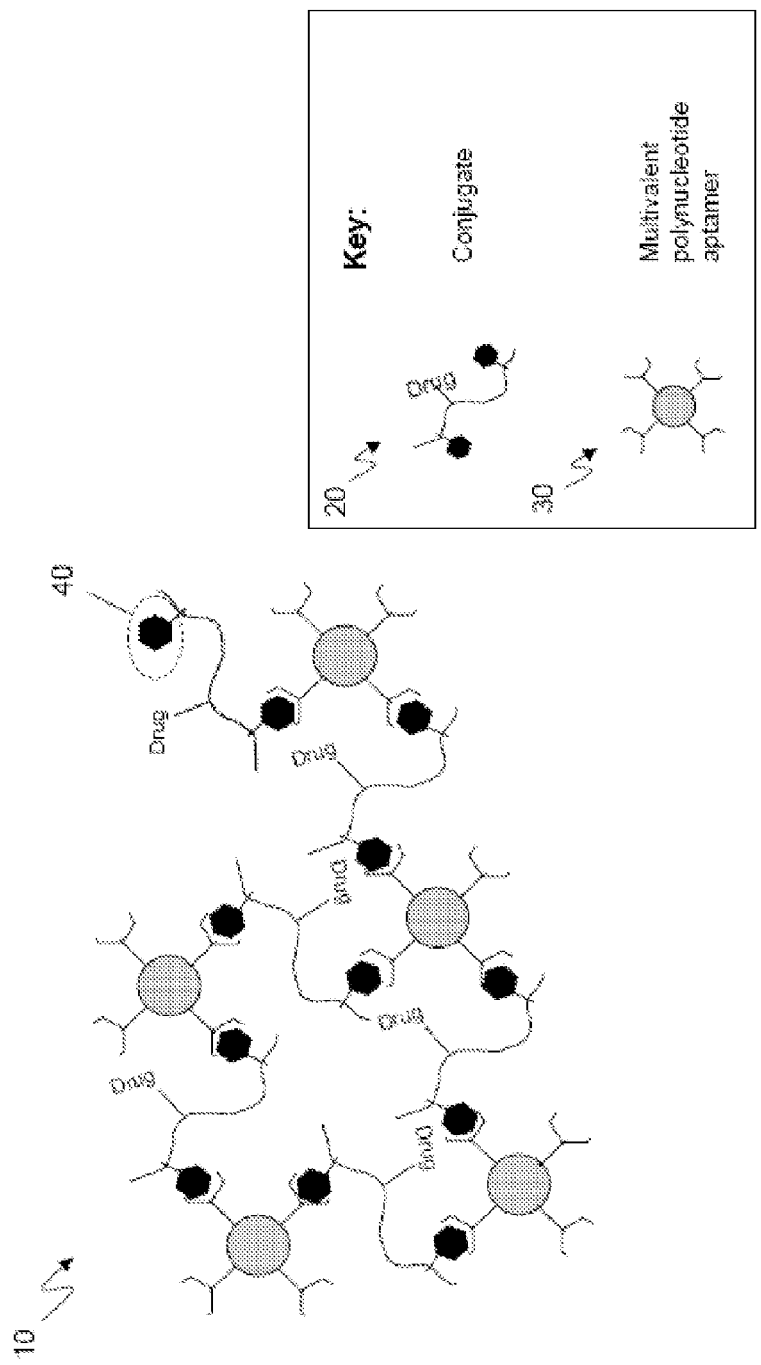
FIG. 5 (lower) shows pegylated Con A elution profiles from polyacrylamide bead column (■), glycogen bead column (♦), and native Con A elution from glycogen bead column (●). Elution steps 1-15 (left to right): Bind, 3× buffer washes, 400, 800, 1600, 3200, 6400, 4×12500 mg/dL glucose, respectively.

In one aspect and as shown in FIG. 5, the disclosure provides a cross-linked material 10 that includes multivalent polynucleotide aptamers 30 that bind a target molecule; and conjugates 20 that include two or more separate affinity ligands 40 bound to a conjugate framework, wherein the two or more affinity ligands 40 compete with the target molecule for binding with the aptamers 30 and wherein conjugates 20 are cross-linked within the material 10 as a result of non-covalent interactions between aptamers 30 and affinity ligands 40 on different conjugates 20.

These materials are designed to release amounts of conjugate in response to desired concentrations of the target molecule. Depending on the end application, in various embodiments, the conjugates may also include a drug and/or a detectable label. The drug, detectable label and affinity ligands may be covalently or non-covalently bound to the conjugate framework. The disclosure also provides methods of using these materials and methods of making these materials. In another aspect, the disclosure provides exemplary aptamers for use in glucose responsive materials instead of lectins such as Con A.

The aptamers bind a target molecule (e.g., without limitation glucose, lactate, a hormone, etc.) and are multivalent. The conjugates include a conjugate framework with two or more separate affinity ligands that compete with the target molecule for binding with the aptamers. When aptamers and conjugates are combined in the absence of the target molecule, a non-covalently cross-linked material is formed. When the material is placed in the presence of free target molecules these compete for the interactions between the aptamers and the conjugates. Above a certain concentration of free target molecule, the level of competition becomes such that the material begins to degrade by releasing conjugates. As a result, conjugates are released from the material in a manner which is directly tied to the local concentration of the target molecule.

Polynucleotide Aptamers

The polynucleotide aptamers bind the target molecule and are multivalent (i.e., capable of binding more than one target molecule). The present disclosure is not limited to any particular target molecule. Thus, in various embodiments, the target molecule can be a metabolite (e.g., without limitation glucose, folate, lactate, glutamate, glutamine, pyruvate, citrate, malate, an amino acid, a lipid, etc.). In other embodiments, the target molecule can be a hormone which may be peptidic or non-peptidic (e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone-releasing hormone, human chorionic gonadotropin, histamine, human placental lactogen, insulin, insulin-like growth factor, growth hormone, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone, thyroxine, triiodothyronine, vasopressin, etc.).

In general, monovalent aptamers will first be generated based on their binding properties for the target molecule. As is well known in the art, aptamers to a variety of target molecules can be generated through a process of in vitro selection. An exemplary method is described in Example 3 below. See also Ellington and Szostak (1990) *Nature* 346:818; Tuerk and Gold (1990) *Science* 249:505; and U.S. Pat. No. 5,582,981.

Typically, the process begins with the synthesis of a library consisting of randomly generated polynucleotide sequences of fixed length flanked by constant 5' and 3' ends that serve as primers. In certain embodiments (e.g., when optimizing an aptamer) one might start with a sequence which is known to bind the target molecule and generate a library which includes a collection of polynucleotides which exhibit a limited range of changes from the starting sequence (e.g., a random set of single mutations). The sequences in the library are then exposed to the target molecule and those that do not bind the target are removed (e.g., by affinity chromatography). The bound sequences are then eluted and amplified (e.g., by cloning and subsequent transcription or by PCR) to prepare for subsequent rounds of selection in which the stringency of the elution conditions is increased or modified to identify sequences with the desired binding affinity and/or specificity. Jarosch et al. (2006) *Nucleic Acids Res.* 34:86 have described methods that allow the process to be performed without the constant primer regions.

In various embodiments, the selection process may involve steps in which the stringency of the elution conditions are gradually increased in order to select aptamers with high affinity for the target molecule.

In various embodiments, the selection process may involve steps in which the elution conditions are modified (e.g., by using a different affinity column) in order to select aptamers with desired specificity for the target molecule.

In various embodiments the selection process may generate a collection of sublibraries (or "pools") each of which comprises aptamers with similar affinities and/or specificities for the target molecule. In various embodiments the selection process may generate a single aptamer sequence (or "monoclonal"). In various embodiments the aptamers are DNA based. In various embodiments the aptamers are RNA based. In various embodiments the aptamers are mixed RNA/DNA aptamers.

Multivalent aptamers can be generated by covalently or non-covalently linking two or more of these monovalent aptamers into a single construct. An exemplary method is described in Example 4 below. Typically, two or more aptamers (which may have the same or different sequences) may be bound directly to one another (e.g., via a coupling agent) or indirectly through an independent framework. In various embodiments 2, 3, 4, 5, 6, 7 or 8 aptamers may be combined into a single construct. In various embodiments the 2, 3, 4, 5, 6, 7 or 8 aptamers may have the same sequence. It will be appreciated that either one of these approaches may require the aptamers to be chemically modified (e.g., to include pendant reactive groups) prior to coupling. It will also be appreciated that the aptamers of the present disclosure are not limited to a particular coupling reaction or framework (e.g., they can be prepared using frameworks that include polymeric and/or non-polymeric structures). It will further be appreciated that the frameworks may be linear, branched, hyperbranched and/or a combination of these. Exemplary frameworks and coupling chemistries are described below in the context of the conjugates.

In various embodiments the aptamers are covalently bound to each other or a framework. In such embodiments, the aptamers can be directly bound (i.e., with no intervening chemical groups) or indirectly bound through a spacer (e.g., a coupling agent or covalent chain that provides some physical separation between the aptamers or between the aptamers and framework). As discussed below in the context of the conjugates it is to be understood that aptamers may be covalently bound to each other or a framework through any number of chemical linkages, including but not limited to amide, ester, ether, isourea, and imine bonds.

In various embodiments, the two or more aptamers are non-covalently bound to each other or to a framework. In certain embodiments, the dissociation constant ($K_d$) of the non-covalent linkage in human serum is less than 1 pmol/L. For example, aptamers may be non-covalently bound to each other or a framework via a non-covalent ligand-receptor pair as is well known in the art (e.g., without limitation a biotin-avidin based pair). In such an embodiment, one member of the ligand receptor-pair is covalently bound to one aptamer while the other member of the pair is covalently bound to the other aptamer or framework. When the aptamers (or aptamers and framework) are combined, the strong non-covalent interaction between the ligand and its receptor causes the aptamers to become non-covalently bound to each other (or the framework). Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-S-transferase (GST), c-myc, FLAG® and further those described in Kessler pp. 105-152 of *Advances in Mutagenesis*" Ed. by Kessler, Springer-Verlag, 1990; *"Affinity Chromatography: Methods and Protocols (Methods in Molecular Biology)*" Ed. by Pascal Baillon, Humana Press, 2000; and *"Immobilized Affinity Ligand Techniques"* by Hermanson et al., Academic Press, 1992.

In various embodiments, a multivalent aptamer of the present disclosure binds glucose and includes at least 40, 50, 60, 70 or 80 contiguous nucleotides of SEQ ID NO. 1, 2, 3, 4, 5, 6 or 7 (see FIG. 2). In various embodiments, a multivalent aptamer of the present disclosure binds glucose and comprises one or more regions having at least 70% homology with at least 40, 50, 60, 70 or 80 contiguous nucleotides of SEQ ID NO. 1, 2, 3, 4, 5, 6 or 7. In various embodiments, a multivalent aptamer of the present disclosure binds glucose and comprises one or more regions having at least 80% homology with at least 40, 50, 60, 70 or 80 contiguous nucleotides of SEQ ID NO. 1, 2, 3, 4, 5, 6 or 7. In various embodiments, a multivalent aptamer of the present disclosure binds glucose and comprises one or more regions having at least 90% homology with at least 40, 50, 60, 70 or 80 contiguous nucleotides of SEQ ID NO. 1, 2, 3, 4, 5, 6 or 7. In various embodiments, a multivalent aptamer of the present disclosure binds glucose and comprises one or more regions having at least 95% homology with at least 40, 50, 60, 70 or 80 contiguous nucleotides of SEQ ID NO. 1, 2, 3, 4, 5, 6 or 7. In certain embodiments, a multivalent aptamer may include two or more copies of any one of the foregoing nucleotide sequences.

In various embodiments, a multivalent aptamer of the present disclosure binds glucose and includes a nucleotide sequence of SEQ ID NO. 8, 9 or 10:

| SEQUENCE[1] | SEQ ID NO. |
|---|---|
| NNANCYGCGNGNNANCYYCARNCANNAA CAGNACACNNAA | 8 |
| NACAGNACGGGGNGANCACCAANGCNG AANGCAGAAGCG | 9 |
| GNCAGGANAGGNGCAAGAANGCGAAANN CGCAGGCNGGNG | 10 |

[1]N = U/T; Y = U/T or C; R = A or G

SEQ ID NO. 8 is a consensus sequence based on the central (i.e., non-primer) regions of SEQ ID NOs. 2, 3, 5, 7 (see FIG. 2). SEQ ID NO. 9 is based on the central region of SEQ ID NO. 4. SEQ ID NO. 10 is based on the central region of SEQ ID NO. 6. In certain embodiments, a multivalent aptamer may include two or more copies of a nucleotide sequence of SEQ ID NO. 8, 9 or 10.

In certain embodiments, the nucleotide sequence is an RNA sequence and N=U. In certain embodiments, the nucleotide sequence is a DNA sequence and N=T.

In certain embodiments, a multivalent aptamer of the present disclosure binds glucose and includes a nucleotide sequence of SEQ ID NO. 8 wherein Y=U/T. In certain embodiments, a multivalent aptamer of the present disclosure binds glucose and includes a nucleotide sequence of SEQ ID NO. 8 wherein Y=C. In certain embodiments, a multivalent aptamer of the present disclosure binds glucose and includes a nucleotide sequence of SEQ ID NO. 8 wherein Y(6)=U/T and Y(17-18)=C. In certain embodiments, a multivalent aptamer of the present disclosure binds glucose and includes a nucleotide sequence of SEQ ID NO. 8 wherein R=A. In certain embodiments, a multivalent aptamer of the present disclosure binds glucose and includes a nucleotide sequence of SEQ ID NO. 8 wherein R=G.

In various embodiments, a multivalent aptamer of the present disclosure binds glucose and comprises one or more regions having at least 70% homology with at least 30 contiguous nucleotides of SEQ ID NO. 8, 9 or 10. In various embodiments, a multivalent aptamer of the present disclosure binds glucose and comprises one or more regions having at least 80% homology with at least 30 contiguous nucleotides of SEQ ID NO. 8, 9 or 10. In various embodiments, a multivalent aptamer of the present disclosure binds glucose and comprises one or more regions having at least 90% homology with at least 30 contiguous nucleotides of SEQ ID NO. 8, 9 or 10. In various embodiments, a multivalent aptamer of the present disclosure binds glucose and comprises one or more regions having at least 95% homology with at least 30 contiguous nucleotides of SEQ ID NO. 8, 9 or 10.

In various embodiments, a multivalent aptamer of the present disclosure binds glucose and comprises one or more regions having at least 70% homology with SEQ ID NO. 8, 9 or 10. In various embodiments, a multivalent aptamer of the present disclosure binds glucose and comprises one or more regions having at least 80% homology with SEQ ID NO. 8, 9 or 10. In various embodiments, a multivalent aptamer of the present disclosure binds glucose and comprises one or more regions having at least 90% homology with SEQ ID NO. 8, 9 or 10. In various embodiments, a multivalent aptamer of the present disclosure binds glucose and comprises one or more regions having at least 95% homology with SEQ ID NO. 8, 9 or 10.

In various embodiments, the present disclosure provides a pool of monovalent aptamers that bind glucose and each independently comprise a region having at least 70% homology with at least 30 contiguous nucleotides of SEQ ID NO. 8, 9 or 10. In various embodiments, the present disclosure provides a pool of monovalent aptamers that bind glucose and each independently comprise a region having at least 80% homology with at least 30 contiguous nucleotides of SEQ ID NO. 8, 9 or 10. In various embodiments, the present disclosure provides a pool of monovalent aptamers that bind glucose and each independently comprise a region having at least 90% homology with at least 30 contiguous nucleotides of SEQ ID NO. 8, 9 or 10. In various embodiments, the present disclosure provides a pool of monovalent aptamers that bind glucose and each independently comprise a region having at least 95% homology with at least 30 contiguous nucleotides of SEQ ID NO. 8, 9 or 10. In certain embodiments, the pool includes more than 10, more than 20, more than 50 or more than 100 monovalent aptamers.

In various embodiments, the present disclosure provides a pool of monovalent aptamers that bind glucose and each independently comprise a region having at least 70% homology with SEQ ID NO. 8, 9 or 10. In various embodiments, the present disclosure provides a pool of monovalent aptamers that bind glucose and each independently comprise a region having at least 80% homology with SEQ ID NO. 8, 9 or 10. In various embodiments, the present disclosure provides a pool of monovalent aptamers that bind glucose and each independently comprise a region having at least 90% homology with SEQ ID NO. 8, 9 or 10. In various embodiments, the present disclosure provides a pool of monovalent aptamers that bind glucose and each independently comprise a region having at least 95% homology with SEQ ID NO. 8, 9 or 10. In certain embodiments, the pool includes more than 10, more than 20, more than 50 or more than 100 monovalent aptamers.

Conjugates

The conjugates include two or more separate affinity ligands bound to a conjugate framework. The two or more separate affinity ligands compete with the target molecule for binding with the aptamer. Depending on the end application, the conjugates may also include a drug and/or a detectable label. The affinity ligands, drug, and/or detectable label may be covalently or non-covalently bound to the conjugate framework.

Affinity Ligands

The two or more separate affinity ligands may have the same or different chemical structures. The two or more separate affinity ligands may have the same chemical structure as the target molecule itself or may be a chemically related species of the target molecule. The only requirement is that they compete with the target molecule for binding with the aptamer. In certain embodiments, the relative affinity of the conjugate and target molecule for the aptamer is in the range of 1:1 to 100:1 (where a relative affinity of 100:1 means that, in an equilibrium mixture of conjugate, target molecule and aptamer (in pH 7 HEPES buffered saline at 37 C), the aptamer will bind about equal molar amounts of conjugate and target molecule if the concentration of target molecule is 100× the concentration of conjugate). In certain embodiments, the relative affinity is in the range of 1:1 to 50:1, 1:1 to 10:1, 1:1 to 5:1 or 1:1 to 2:1. In various embodiments it may be advantageous for the affinity ligands to have a different chemical structure from the target molecule, e.g., in order to fine tune the relative affinity of the aptamer for the conjugates and the target molecule. For example, when the target molecule is glucose one might use a saccharide or a polysaccharide as one or more of affinity ligands. For example, when the target molecule is glucose the affinity ligands may include a saccharide. Thus, in certain embodiments, the affinity ligands are capable of competing with glucose for binding to an aptamer of the present disclosure.

In certain embodiments, the affinity ligand is of formula (IVa) or (IVb):

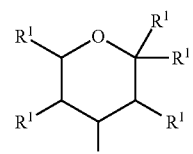

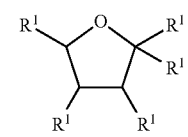

wherein:
each $R^1$ is independently hydrogen, —$OR^y$, —$N(R^y)_2$, —$SR^y$, —O—Y, -G-Z, or —$CH_2R^x$;
each $R^x$ is independently hydrogen, —$ORS^y$, —$N(R^y)_2$, —SW, or —O—Y;
each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$;
each Y is independently a monosaccharide, disaccharide, or trisaccharide;
each G is independently a covalent bond or an optionally substituted $C_{1-9}$ alkylene, wherein one or more methylene units of G is optionally replaced by —O—, —S—, —$N(R^2)$—, —C(O)—, —OC(O)—, —C(O)O—, —C(O)N($R^2$)—, —$N(R^2)C(O)$—, —$N(R^2)C(O)N(R^2)$—, —$SO_2$—, —$SO_2N(R^2)$—, —$N(R^2)SO_2$—, or —$N(R^2)SO_2N(R^2)$—;
each Z is independently halogen, —$N(R^2)_2$, —$OR^2$, —$SR^2$, —$N_3$, —C≡$CR^2$, —$CO_2R^2$, —$C(O)R^2$, or —$OSO_2R^2$; and
each $R^2$ is independently hydrogen or an optionally substituted group selected from $C_{1-6}$ aliphatic, phenyl, a 4-7 membered heterocyclic ring having 1-2 heteroatoms selected from nitrogen, oxygen, or sulfur, or a 5-6 membered monocyclic heteroaryl ring having 1-4 heteroatoms selected from nitrogen, oxygen, or sulfur.

In certain embodiments, the affinity ligand of formula (IVa) or (IVb) is a monosaccharide. In certain embodiments, the affinity ligand is a disaccharide. In certain embodiments, the affinity ligand is a trisaccharide. In certain embodiments, the affinity ligand is a tetrasaccharide. In certain embodiments, the affinity ligand comprises no more than four saccharide moieties.

As defined generally above, each $R^1$ is independently hydrogen, —$OR^y$, —$N(R^y)_2$, —$SR^y$, —O—Y, -G-Z, or —$CH_2R^x$. In certain embodiments, $R^1$ is hydrogen. In certain embodiments, $R^1$ is —OH. In other embodiments, $R^1$ is —NHC(O)$CH_3$. In certain embodiments, $R^1$ is —O—Y. In certain other embodiments, $R^1$ is -G-Z. In some embodiments, $R^1$ is —$CH_2OH$. In other embodiments, $R^1$ is —$CH_2$—O—Y. In yet other embodiments, $R^1$ is —$NH_2$. One of ordinary skill in the art will appreciate that each $R^1$ substituent in formula (IVa) or (IVb) may be of (R) or (S) stereochemistry.

As defined generally above, each $R^x$ is independently hydrogen, —$OR^y$, —$N(R^y)_2$, —$SR^y$, or —O—Y. In some embodiments, $R^x$ is hydrogen. In certain embodiments, $R^x$ is —OH. In other embodiments, $R^x$ is —O—Y.

As defined generally above, each $R^y$ is independently —$R^2$, —$SO_2R^2$, —$S(O)R^2$, —$P(O)(OR^2)_2$, —$C(O)R^2$, —$CO_2R^2$, or —$C(O)N(R^2)_2$. In some embodiments, $R^y$ is hydrogen. In other embodiments, $R^y$ is —$R^2$. In some embodiments, R$^y$ is —C(O)R$^2$. In certain embodiments, R$^y$ is acetyl. In other embodiments, R$^y$ is —SO$_2$R$^2$, —S(O)R$^2$, —P(O)(OR$^2$)$_2$, —CO$_2$R$^2$, or —C(O)N(R$^2$)$_2$.

As defined generally above, Y is a monosaccharide, disaccharide, or trisaccharide. In certain embodiments, Y is a monosaccharide. In some embodiments, Y is a disaccharide. In other embodiments, Y is a trisaccharide. In some embodiments, Y is mannose, glucose, fructose, galactose, rhamnose, or xylopyranose. In some embodiments, Y is sucrose, maltose, turanose, trehalose, cellobiose, or lactose. In certain embodiments, Y is mannose. In certain embodiments, Y is D-mannose. One of ordinary skill in the art will appreciate that the saccharide Y is attached to the oxygen group of —O—Y through anomeric carbon to form a glycosidic bond. The glycosidic bond may be of an alpha or beta configuration.

As defined generally above, each G is independently a covalent bond or an optionally substituted C$_{1-9}$ alkylene, wherein one or more methylene units of G is optionally replaced by —O—, —S—, —N(R$^2$)—, —C(O)—, —OC(O)—, —C(O)O—, —C(O)N(R$^2$)—, —N(R$^2$)C(O)—, —N(R$^2$)C(O)N(R$^2$)—, —SO$_2$—, —N(R$^2$)—, —N(R$^2$)SO$_2$—, or —N(R$^2$)SO$_2$N(R$^2$)—. In some embodiments, G is a covalent bond. In certain embodiments, G is —O—C$_{1-8}$ alkylene. In certain embodiments, G is —OCH$_2$CH$_2$—.

As defined generally above, each Z is independently halogen, —N(R$^2$)$_2$, —OR$^2$, —SR$^2$, —N$_3$, —C≡CR$^2$, —CO$_2$R$^2$, —C(O)R$^2$, or —OSO$_2$R$^2$. In some embodiments, Z is a halogen or —OSO$_2$R$^2$. In other embodiments, Z is —N$_3$ or —C≡CR$^2$. In certain embodiments, Z is —N(R$^2$)$_2$, —OR$^2$, or —SR$^2$. In certain embodiments, Z is —SH. In certain embodiments, Z is —NH$_2$. In certain embodiments, -G-Z is —OCH$_2$CH$_2$NH$_2$.

In some embodiments, the R$^1$ substituent on the C1 carbon of formula (IVa) is -G-Z to give a compound of formula (IVa-i):

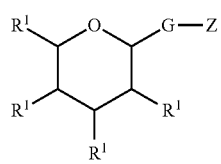

IVa-i wherein R$^1$, G, and Z are as defined and described herein.

In some embodiments, the ligand is of formula (IVa-ii):

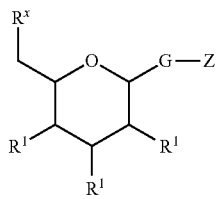

IVa-ii wherein R$^1$, R$^x$, G, and Z are as defined and described herein.

For example, in certain embodiments, one might use an affinity ligand that includes one or more of the following: glucose, sucrose, maltose, mannose, derivatives of these (e.g., glucosamine, mannosamine, methylglucose, methylmannose, ethylglucose, ethylmannose, etc.) and/or higher order combinations of these (e.g., a bimannose, a linear and/or branched trimannose, etc.). In certain embodiments, the affinity ligand includes a monosaccharide. In certain embodiments, the affinity ligand includes a disaccharide. In certain embodiments, the affinity ligand includes a trisaccharide. In certain embodiments, the affinity ligand includes a polysaccharide. In some embodiments, the affinity ligand includes a saccharide and one or more amine groups. In some embodiments, the affinity ligand is aminoethylglucose (AEG). In some embodiments, the affinity ligand is aminoethylmannose (AEM). In some embodiments, the affinity ligand is aminoethylbimannose (AEBM). In some embodiments, the affinity ligand is aminoethyltrimannose (AETM). In some embodiments, the affinity ligand is β-aminoethyl-N-acetylglucosamine (AEGA). In some embodiments, the affinity ligand is aminoethylfucose (AEF). In other embodiments, the affinity ligand is D-glucosamine (GA). In certain embodiments, a saccharide ligand is of the "D" configuration. In other embodiments, a saccharide ligand is of the "L" configuration. Below we show the structures of these exemplary affinity ligands. Other exemplary affinity ligands will be recognized by those skilled in the art.

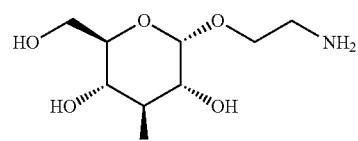

AEG

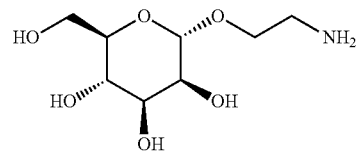

AEM

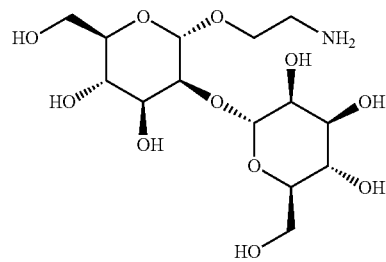

AEBM

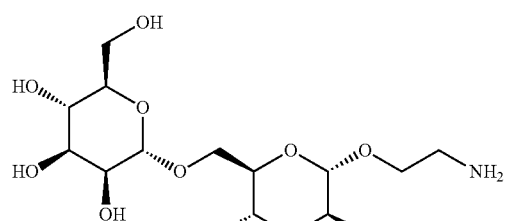

AETM

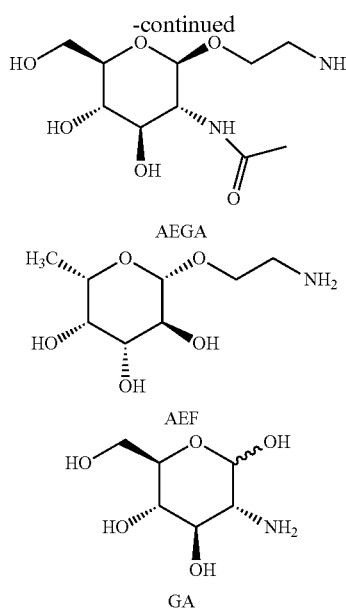

AEGA

AEF

GA

In various embodiments, the affinity ligand is a polysaccharide, glycopeptide or glycolipid. In certain embodiments, the affinity ligand includes from 2-10 saccharide moieties, e.g., 2, 3, 4, 5, 6, 7, 8, 9 or 10 moieties. The terminal and/or internal residues of the polysaccharide, glycopeptide or glycolipid may be selected based on the saccharide specificity of the aptamer in question (e.g., see Goldstein et al., *Biochem. Biophys. Acta* 317:500-504, 1973 and L is et al., *Ann. Rev. Biochem.* 55:35-67, 1986).

In various embodiments, the affinity ligands for a particular conjugate/aptamer combination may be selected empirically. According to such embodiments one or more affinity ligands are screened based on their relative binding affinities for the aptamer as compared to glucose. In certain embodiments a library of saccharides and/or polysaccharides are screened in this manner. A suitable affinity ligand will exhibit a detectable level of competition with glucose but will not compete so strongly that it prevents all binding between the aptamer and glucose.

Other exemplary target molecule/affinity ligand combinations will be recognized by those skilled in the art. In general, an affinity ligand can be generated for any target molecule using the target molecule itself and/or by generating derivatives of the target molecule (e.g., by making chemical and/or stereochemical modifications to the target molecule and then screening the resulting derivative for its relative affinity to the aptamer in question).

As discussed in more detail below, the affinity ligands may be naturally present within the framework of the conjugate (e.g., as part of a polymer backbone or as a side group of a monomer). Alternatively (or additionally) affinity ligands may be artificially incorporated into the conjugate framework (e.g., in the form of a chemical group that is synthetically added to a conjugate framework). In certain embodiments, a conjugate may include a framework which comprises 5 or more, 10 or more, 20 or more, 25 or more, 50 or more, or 100 or more affinity ligands. In certain embodiments, a conjugate may include a framework which comprises 2-5, 2-10, 2-20, 2-25, 2-50 or 2-100 affinity ligands. In certain embodiments, a conjugate may include a framework which comprises as few as 2, 3 or 4 separate affinity ligands.

Methods for conjugating affinity ligands to a conjugate framework are discussed in more detail below. In certain embodiments, when the affinity ligands include a saccharide, the conjugation (whether direct or indirect) involves the C1, C2 or C6 position of the saccharide. In certain embodiments, the conjugation involves the C1 position. The C1 position is also referred to as the anomeric carbon and may be connected to the conjugate framework in the alpha or beta conformation. In certain embodiments, the C1 position is configured as the alpha anomer. In other embodiments, the C1 position is configured as the beta anomer.

Drug

As noted above, in various embodiments, a conjugate may comprise a drug. For example, a drug may be included when the material is to be used for therapeutic purposes, e.g., to controllably deliver a drug in a patient. It is to be understood that a conjugate can comprise any drug. A conjugate can comprise more than one copy of the same drug and/or can comprise more than one type of drug. The conjugates are not limited to any particular drug and may include small molecule drugs or biomolecular drugs. In general, the drug(s) used will depend on the disease or disorder to be treated.

For example, without limitation, in various embodiments a conjugate can comprise any one of the following drugs: diclofenac, nifedipine, rivastigmine, methylphenidate, fluoroxetine, rosiglitazone, prednison, prednisolone, codeine, ethylmorphine, dextromethorphan, noscapine, pentoxiverine, acetylcysteine, bromhexine, epinephrine, isoprenaline, orciprenaline, ephedrine, fenoterol, rimiterol, ipratropium, cholinetheophyllinate, proxiphylline, bechlomethasone, budesonide, deslanoside, digoxine, digitoxin, disopyramide, proscillaridin, chinidine, procainamide, mexiletin, flecamide, alprenolol, proproanolol, nadolol, pindolol, oxprenolol, labetalol, timolol, atenolol, pentaeritrityltetranitrate, isosorbiddinitrate, isosorbidmononitrate, niphedipin, phenylamine, verapamil, diltiazem, cyclandelar, nicotinylalcholhol, inositolnicotinate, alprostatdil, etilephrine, prenalterol, dobutamine, dopamine, dihydroergotamine, guanetidine, betanidine, methyldopa, reserpine, guanfacine, trimethaphan, hydralazine, dihydralazine, prazosine, diazoxid, captopril, nifedipine, enalapril, nitroprusside, bendroflumethiazide, hydrochlorthiazide, metychlothiazide, polythiazide, chlorthalidon, cinetazon, clopamide, mefruside, metholazone, bumetanide, ethacrynacide, spironolactone, amiloride, chlofibrate, nicotinic acid, nicheritrol, brompheniramine, cinnarizine, dexchlorpheniramine, clemastine, antazoline, cyproheptadine, proethazine, cimetidine, ranitidine, sucralfat, papaverine, moxaverine, atropin, butylscopolamin, emepron, glucopyrron, hyoscyamine, mepensolar, methylscopolamine, oxiphencyclimine, probanteline, terodilin, sennaglycosides, sagradaextract, dantron, bisachodyl, sodiumpicosulfat, etulos, diphenolxylate, loperamide, salazosulfapyridine, pyrvin, mebendazol, dimeticon, ferrofumarate, ferrosuccinate, ferritetrasemisodium, cyanochobalamine, folid acid heparin, heparin co-factor, diculmarole, warfarin, streptokinase, urokinase, factor VIII, factor IX, vitamin K, thiopeta, busulfan, chlorambucil, cyclophosphamid, melfalan, carmustin, mercatopurin, thioguanin, azathioprin, cytarabin, vinblastin, vinchristin, vindesin, procarbazine, dacarbazine, lomustin, estramustin, teniposide, etoposide, cisplatin, amsachrin, aminogluthetimid, phosphestrol, medroxiprogresterone, hydroxiprogesterone, megesterol, noretisteron, tamoxiphen, ciclosporin, sulfosomidine, bensylpenicillin, phenoxymethylpenicillin, dicloxacillin, cloxacillin, flucoxacillin, ampicillin, amoxicillin, pivampicillin, bacampicillin, piperacillin, meziocillin, mecillinam, pivmecillinam, cephalotin, cephalexin, cephradin, cephydroxil, cephaclor, cefuroxim, cefotaxim, ceftazidim, cefoxitin, aztreonam, imipenem, cilastatin, tetracycline, lymecycline, demeclocycline, metacycline, oxitetracycline, doxycycline, chloramphenicol, spiramycin, fusidic acid, lincomycin, clindamycin, spectinomycin, rifampicin, amphotericin B, griseofulvin, nystatin, vancomycin, metronidazole, timidazole, trimethoprim, norfloxacin, salazosulfapyridin, aminosalyl, isoniazid, etambutol, nitrofurantoin, nalidixic acid, metanamine, chloroquin, hydroxichloroquin, timidazol, ketokonazol, acyclovir, interferon idoxuridin, retinal, tiamin, dexpantenol, pyridoxin, folic acid, ascorbic acid, tokoferol, phytominadion, phenfluramin, corticotropin, tetracosactid, tyrotropin, somatotoprin, somatrem, vasopressin, lypressin, desmopressin, oxytocin, chloriongonadotropin, cortison, hydrocortisone, fluodrocortison, prednison, prednisolon, fluoximesteron, mesterolon, nandrolon, stanozolol, oximetolon, cyproteron, levotyroxin, liotyronin, propylthiouracil, carbimazol, tiamazol, dihydrotachysterol, alfacalcidol, calcitirol, insulin, tolbutamid, chlorpropamid, tolazamid, glipizid, glibenclamid, phenobarbital, methyprylon, pyrityidion, meprobamat, chlordiazepoxid, diazepam, nitrazepam, baclofen, oxazepam, dikaliumclorazepat, lorazepam, flunitrazepam, alprazolam, midazolam, hydroxizin, dantrolene, chlomethiazol, propionmazine, alimemazine, chlorpromazine, levomepromazine, acetophenazine, fluphenazine, perphenazine, prochlorperazine, trifluoperazine, dixyrazine, thiodirazine, periciazin, chloprothixene, tizanidine, zaleplon, zuclopentizol, flupentizol, thithixen, haloperidol, trimipramin, opipramol, chlomipramin, desipramin, lofepramin, amitriptylin, nortriptylin, protriptylin, maptrotilin, caffeine, cinnarizine, cyclizine, dimenhydinate, meclozine, prometazine, thiethylperazine, metoclopramide, scopolamine, phenobarbital, phenyloine, ethosuximide, primidone, carbamazepine, chlonazepam, orphenadrine, atropine, bensatropine, biperiden, metixene, procylidine, levodopa, bromocriptin, amantadine, ambenon, pyridostigmine, synstigmine, disulfuram, morphine, codeine, pentazocine, buprenorphine, pethidine, phenoperidine, phentanyl, methadone, piritramide, dextropropoxyphene, ketobemidone, acetylsalicylic acid, celecoxib, phenazone, phenylbutazone, azapropazone, piroxicam, ergotamine, dihydroergotamine, cyproheptadine, pizitifen, flumedroxon, allopurinol, probenecid, sodiummaurothiomalate auronofin, penicillamine, estradiol, estradiolvalerianate, estriol, ethinylestradiol, dihydrogesteron, lynestrenol, medroxiprogresterone, noretisterone, cyclophenile, clomiphene, levonorgestrel, mestranol, ornidazol, timidazol, ekonazol, chlotrimazol, natamycine, miconazole, sulbentin, methylergotamine, dinoprost, dinoproston, gemeprost, bromocriptine, phenylpropanolamine, sodiumchromoglicate, azetasolamide, dichlophenamide, betacarotene, naloxone, calciumfolinate, in particular clonidine, thephylline, dipyradamol, hydrochlothiazade, scopolamine, indomethacine, furosemide, potassium chloride, morphine, ibuprofen, salbutamol, terbutalin, calcitonin, etc. It is to be undersrtood that this list is intended to be exemplary and that any drug, whether known or later discovered, may be used in a conjugate of the present disclosure.

In various embodiments, a conjugate may include a hormonal drug which may be peptidic or non-peptidic, e.g., adrenaline, noradrenaline, angiotensin, atriopeptin, aldosterone, dehydroepiandrosterone, androstenedione, testosterone, dihydrotestosterone, calcitonin, calcitriol, calcidiol, corticotropin, cortisol, dopamine, estradiol, estrone, estriol, erythropoietin, follicle-stimulating hormone, gastrin, ghrelin, glucagon, gonadotropin-releasing hormone, growth hormone, growth hormone-releasing hormone, human chorionic gonadotropin, histamine, human placental lactogen, insulin, insulin-like growth factor, inhibin, leptin, a leukotriene, lipotropin, melatonin, orexin, oxytocin, parathyroid hormone, progesterone, prolactin, prolactin-releasing hormone, a prostglandin, renin, serotonin, secretin, somatostatin, thrombopoietin, thyroid-stimulating hormone, thyrotropin-releasing hormone (or thyrotropin), thyrotropin-releasing hormone, thyroxine, triiodothyronine, vasopressin, etc. In certain embodiments, the hormone may be selected from glucagon, insulin, insulin-like growth factor, leptin, thyroid-stimulating hormone, thyrotropin-releasing hormone (or thyrotropin), thyrotropin-releasing hormone, thyroxine, and triiodothyronine. It is to be understood that this list is intended to be exemplary and that any hormonal drug, whether known or later discovered, may be used in a conjugate of the present disclosure.

In various embodiments, a conjugate may include a thyroid hormone.

In various embodiments, a conjugate may include an antidiabetic drug (i.e., a drug which has a beneficial effect on patients suffering from diabetes).

Figure 6:
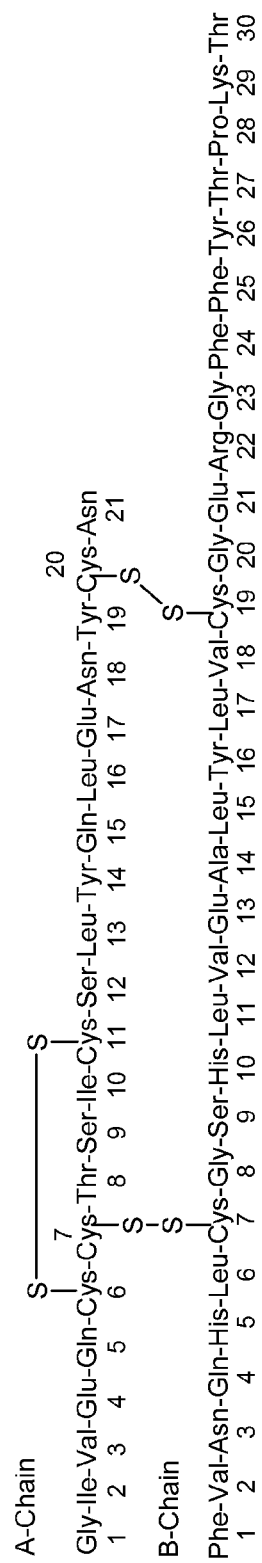
FIG. 6: shows the structure of wild-type human insulin.

In various embodiments, a conjugate may include an insulin molecule. By "an insulin molecule" we intend to encompass both wild-type and modified forms of insulin as long as they are bioactive (i.e., capable of causing a detectable reduction in glucose when administered in vivo). Wild-type insulin includes insulin from any species whether in purified, synthetic or recombinant form (e.g., human insulin, porcine insulin, bovine insulin, rabbit insulin, sheep insulin, etc.). A number of these are available commercially, e.g., from Sigma-Aldrich (St. Louis, Mo.). A variety of modified forms of insulin are known in the art (e.g. see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of one or more amino acids). In general, a bioactive mutant form of insulin will typically differ from wild-type insulin by 1-10 (e.g., from 1-5 or 1-2) amino acid substitutions, additions or deletions. The wild-type sequence of human insulin (A-chain and B-chain) is shown below and in FIG. 6.

```
A-Chain (SEQ ID NO: 11):
GIVEQCCTSICSLYQLENYCN

B-Chain (SEQ ID NO: 12):
FVNQHLCGSHLVEALYLVCGERGFFYTPKT
```

Human insulin differs from rabbit, porcine, bovine, and sheep insulin only in amino acids A8, A9, A10, and B30 (see table below).

| Insulin | Amino Acid Position | | | |
| --- | --- | --- | --- | --- |
|  | A8 | A9 | A10 | B30 |
| human | Thr | Ser | Ile | Thr |
| rabbit | Thr | Ser | Ile | Ser |
| porcine | Thr | Ser | Ile | Ala |
| bovine | Ala | Ser | Val | Ala |
| sheep | Ala | Gly | Val | Ala |

In various embodiments, an insulin molecule of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which proline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a lysine residue and lysine at position B29 has been replaced with a glutamic acid residue ($Lys^{B3}Glu^{B29}$-human insulin).

In various embodiments, an insulin molecule of the present disclosure has an isoelectric point that is shifted relative to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin molecule of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure is truncated. For example, in certain embodiments, a B-peptide sequence of an insulin polypeptide of the present disclosure is missing B1, B2, B3, B26, B27, B28, B29 and/or B30. In certain embodiments, combinations of residues are missing from the B-peptide sequence of an insulin polypeptide of the present disclosure. For example, the B-peptide sequence may be missing residues B(1-2), B(1-3), B(29-30), B(28-30), B(27-30) and/or B(26-30). In some embodiments, these deletions and/or truncations apply to any of the aforementioned insulin molecules (e.g., without limitation to produce des(B30)-insulin lispro, des(B30)-insulin aspart, des(B30)-insulin glulisine, des(B30)-insulin glargine, etc.).

In some embodiments, an insulin molecule contains additional amino acid residues on the N- or C-terminus of the A or B-peptide sequences. In some embodiments, one or more amino acid residues are located at positions A0, A21, B0 and/or B31. In some embodiments, one or more amino acid residues are located at position A0. In some embodiments, one or more amino acid residues are located at position A21. In some embodiments, one or more amino acid residues are located at position B0. In some embodiments, one or more amino acid residues are located at position B31. In certain embodiments, an insulin molecule does not include any additional amino acid residues at positions A0, A21, B0 or B31.

In certain embodiments, an insulin molecule of the present disclosure is mutated such that one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$; or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin molecule has aspartic acid at position A21 or aspartic acid at position B3, or both.

One skilled in the art will recognize that it is possible to mutate yet other amino acids in the insulin molecule while retaining biological activity. For example, without limitation, the following modifications are also widely accepted in the art: replacement of the histidine residue, of position B10 with aspartic acid ($His^{B10} \rightarrow Asp^{B10}$); replacement of the phenylalanine residue at position B1 with aspartic acid ($Phe^{B1} \rightarrow Asp^{B1}$); replacement of the threonine residue at position B30 with alanine ($Thr^{B30} \rightarrow Ala^{B30}$); replacement of the tyrosine residue at position B26 with alanine ($Tyr^{B26} \rightarrow Ala^{B26}$); and replacement of the serine residue at position B9 with aspartic acid ($Ser^{B9} \rightarrow Asp^{B9}$).

In various embodiments, an insulin molecule of the present disclosure has a protracted profile of action. Thus, in certain embodiments, an insulin molecule of the present disclosure may be acylated with a fatty acid. That is, an amide bond is formed between an amino group on the insulin molecule and the carboxylic acid group of the fatty acid. The amino group may be the alpha-amino group of an N-terminal amino acid of the insulin molecule, or may be the epsilon-amino group of a lysine residue of the insulin molecule. An insulin molecule of the present disclosure may be acylated at one or more of the three amino groups that are present in wild-type insulin or may be acylated on lysine residue that has been introduced into the wild-type sequence. In certain embodiments, an insulin molecule may be acylated at position B1. In certain embodiments, an insulin molecule may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin molecule of the present disclosure is covalently linked to a fatty acid moiety of general formula:

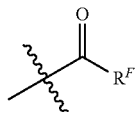

where $R^F$ is hydrogen or a $C_{1-30}$ alkyl group. In some embodiments, $R^F$ is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, or a $C_{12-14}$ alkyl group. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin molecule is Lys and the epsilon-amino group of $Lys^{B28}$ is conjugated to the fatty acid moiety. In certain embodiments, position B3 of the insulin molecule is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20). For example, insulin detemir (LEVEMIR®) is a long acting insulin mutant in which Thr$^{B30}$ has been deleted, and a C14 fatty acid chain (myristic acid) is attached to Lys$^{B29}$.

In certain embodiments, an insulin molecule of the present disclosure comprises the mutations and/or chemical modifications of one of the following insulin molecules: Lys$^{B28}$Pro$^{B29}$-human insulin (insulin lispro), Asp$^{B28}$-human insulin (insulin aspart), Lys$^{B3}$Glu$^{B29}$-human insulin (insulin glulisine), Arg$^{B31}$ Arg$^{B32}$-human insulin (insulin glargine), N$^{εB29}$-myristoyl-des(B30)-human insulin (insulin detemir), Ala$^{B26}$-human insulin, Asp$^{B1}$-human insulin, Arg$^{A0}$-human insulin, Asp$^{B1}$Glu$^{B13}$-human insulin, Gly$^{A21}$-human insulin, Gly$^{A21}$Arg$^{B31}$Arg$^{B32}$-human insulin, Arg$^{A0}$Arg$^{B31}$Arg$^{B32}$-human insulin, Arg$^{A0}$Gly$^{A21}$Arg$^{B31}$Arg$^{B32}$-human insulin, des(B30)-human insulin, des(B27)-human insulin, des(B28-B30)-human insulin, des(B1)-human insulin, des(B1-B3)-human insulin.

In certain embodiments, an insulin molecule of the present disclosure comprises the mutations and/or chemical modifications of one of the following insulin molecules: N$^{εB29}$-palmitoyl-humaninsulin, N$^{εB29}$-myrisotyl-human insulin, N$^{εB28}$-palmitoyl-Lys$^{B28}$Pro$^{B29}$-human insulin, N$^{εB28}$-myristoyl-Lys$^{B28}$Pro$^{B29}$-human insulin.

In certain embodiments, an insulin molecule of the present disclosure comprises the mutations and/or chemical modifications of one of the following insulin molecules: N$^{εB29}$-palmitoyl-des(B30)-human insulin, N$^{εB30}$-myristoyl-Thr$^{B29}$Lys$^{B30}$-human insulin, N$^{εB30}$-palmitoyl-Thr$^{B29}$Lys$^{B30}$-human insulin, N$^{εB29}$-(N-palmitoyl-γ-glutamyl)-des(B30)-human insulin, N$^{εB29}$-(N-lithocolyl-γ-glutamyl)-des(B30)-human insulin, N$^{εB29}$-(ω-carboxyheptadecanoyl)-des(B30)-human insulin, N$^{εB29}$-(ω-carboxyheptadecanoyl)-human insulin.

In certain embodiments, an insulin molecule of the present disclosure comprises the mutations and/or chemical modifications of one of the following insulin molecules: N$^{εB29}$-octanoyl-human insulin, N$^{εB29}$-myristoyl-Gly$^{A21}$Arg$^{B31}$Arg$^{B31}$-human insulin, N$^{εB29}$-myristoyl-Gly$^{A21}$Gln$^{B3}$Arg$^{B31}$Arg$^{B32}$-human insulin, N$^{εB29}$-myristoyl-Arg$^{A0}$Gly$^{A21}$Arg$^{B31}$Arg$^{B32}$-human insulin, N$^{εB29}$-Arg$^{A0}$Gly$^{A21}$Gln$^{B3}$Arg$^{B31}$Arg$^{B32}$-human insulin, N$^{εB29}$-myristoyl-Arg$^{A0}$Gly$^{A21}$Asp$^{B3}$Arg$^{B31}$Arg$^{B32}$-human insulin, N$^{εB29}$-myristoyl-Arg$^{B31}$Arg$^{B32}$-human insulin, N$^{εB29}$-myristoyl-Arg$^{A0}$Arg$^{B31}$Arg$^{B32}$-human insulin, N$^{εB29}$-octanoyl-Gly$^{A21}$Arg$^{B31}$Arg$^{B32}$-human insulin, N$^{εB29}$-octanoyl-Gly$^{A21}$Gln$^{B31}$Arg$^{B31}$Arg$^{B32}$-human insulin, N$^{εB29}$-octanoyl-Arg$^{A0}$Gly$^{A21}$Arg$^{B31}$Arg$^{B32}$-human insulin, N$^{ε29}$-octanoyl-Arg$^{A0}$Gly$^{A21}$Gln$^{B3}$Arg$^{B31}$Arg$^{B32}$-human insulin, N$^{εB29}$-octanoyl-Arg$^{B0}$Gly$^{A21}$Asp$^{B3}$Arg$^{B31}$Arg$^{B32}$-human insulin, N$^{εB29}$-octanoyl-Arg$^{B31}$Arg$^{B32}$-human insulin, N$^{εB29}$-Octanoyl-Arg$^{A0}$Arg$^{B31}$Arg$^{B32}$-human insulin.

In certain embodiments, an insulin molecule of the present disclosure comprises the mutations and/or chemical modifications of one of the following insulin polypeptides: N$^{εB28}$-myristoyl-Gly$^{A21}$Lys$^{B28}$Pro$^{B29}$Arg$^{B31}$Arg$^{B32}$-human insulin, N$^{εB28}$-myristoyl-Gly$^{A21}$Gln$^{B3}$Lys$^{B28}$Pro$^{B30}$Arg$^{B31}$Arg$^{B32}$-human insulin, N$^{εB28}$-myristoyl-Arg$^{A0}$Gly$^{A21}$Lys$^{B28}$Pro$^{B29}$Arg$^{B31}$Arg$^{B32}$-human insulin, N$^{εB28}$-myristoyl-Arg$^{A0}$Gly$^{A21}$Gln$^{B3}$Lys$^{B28}$Pro$^{B29}$Arg$^{B31}$Arg$^{B32}$-human insulin, N$^{εB28}$-myristoyl-Arg$^{A0}$Gly$^{A21}$Asp$^{B3}$Lys$^{B28}$Pro$^{B29}$Arg$^{B31}$Arg$^{B32}$-human insulin, N$^{εB28}$-myristoyl-Lys$^{B28}$Pro$^{B29}$Arg$^{B31}$ Arg$^{B32}$-human insulin, N$^{εB28}$-myristoyl-arg$^{A0}$Lys$^{B28}$Pro$^{B29}$Arg$^{B31}$Arg$^{B32}$-human insulin, N$^{εB28}$-octanoyl-Gly$^{A21}$Lys$^{B28}$Pro$^{B29}$Arg$^{B31}$Arg$^{B32}$-human insulin.

In certain embodiments, an insulin molecule of the present disclosure comprises the mutations and/or chemical modifications of one of the following insulin molecules: N$^{εB28}$-octanoyl-Gly$^{A21}$Gln$^{B3}$Lys$^{B28}$Pro$^{B29}$Arg$^{B31}$Arg$^{B32}$-human insulin, N$^{εB28}$-octanoyl-Arg$^{A0}$Gly$^{A21}$Lys$^{B28}$Pro$^{B29}$ Arg$^{B31}$Arg$^{B32}$-human insulin, N$^{εB28}$-octanoyl-Arg$^{A0}$Gly$^{A21}$Gln$^{B3}$Lys$^{B28}$Pro$^{B29}$Arg$^{B31}$Arg$^{B32}$-human insulin, N$^{εB28}$-octanoyl-Arg$^{A0}$Gly$^{A21}$Asp$^{B3}$Lys$^{B28}$Pro$^{B29}$ Arg$^{B31}$Arg$^{B32}$-human insulin, N$^{εB28}$-octanoyl-Lys$^{B28}$Pro$^{B29}$Arg$^{B31}$Arg$^{B32}$-human insulin, N$^{εB28}$-octanoyl-Arg$^{A0}$Lys$^{B28}$Pro$^{B29}$Arg$^{B3}$Arg$^{B32}$-human insulin.

In certain embodiments, an insulin molecule of the present disclosure comprises the mutations and/or chemical modifications of one of the following insulin molecules: N$^{εB29}$-tridecanoyl-des(B30)-human insulin, N$^{εB29}$-tetradecanoyl-des(B30)-human insulin, N$^{εB29}$-decanoyl-des(B30)-human insulin, N$^{εB29}$-dodecanoyl-des(B30)-human insulin, N$^{εB29}$-tridecanoyl-Gly$^{A21}$-des(B30)-human insulin, N$^{B29}$-tetradecanoyl-Gly$^{A21}$-des(B30)-human insulin, N$^{εB29}$-decanoyl-Gly$^{A21}$-des(B30)-human insulin, N$^{εB29}$-dodecanoyl-Gly$^{A21}$-des(B30)-human insulin, N$^{εB29}$-tridecanoyl-Gly$^{A21}$Gln$^{B3}$-des(B30)-human insulin, NB29-tetradecanoyl-Gly$^{A21}$Gln$^{B3}$-des(B30)-human insulin, N$^{εB29}$-decanoyl-Gly$^{A21}$-Gln$^{B3}$-des(B30)-human insulin, N$^{εB29}$-dodecanoyl-Gly$^{A21}$-GlnB3-des(B30)-human insulin, N$^{εB29}$-tridecanoyl-Ala$^{A21}$-des(B30)-human insulin, N$^{εB29}$-tetradecanoyl-Ala$^{A21}$-des(B30)-human insulin, N$^{εB29}$-decanoyl-Ala$^{A21}$-des(B30)-human insulin, N$^{εB29}$-dodecanoyl-Ala$^{A21}$-des(B30)-human insulin, N$^{εB29}$-tridecanoyl-Ala$^{A21}$-Gln$^{B3}$-des(B30)-human insulin, N$^{εB29}$-tetradecanoyl-Ala$^{A21}$Gln$^{B3}$-des(B30)-human insulin, N$^{εB29}$-decanoyl-Ala$^{A21}$Gln$^{B3}$-des(B30)-human insulin, N$^{εB29}$-dodecanoyl-Ala$^{A21}$Gln$^{B3}$-des(B30)-human insulin, N$^{εB29}$-tridecanoyl-Gln$^{B3}$-des(B30)-human insulin, N$^{εB29}$-tetradecanoyl-Gln$^{B3}$-des(B30)-human insulin, N$^{εB29}$-decanoyl-Gln$^{B3}$-des(B30)-human insulin, N$^{εB29}$-dodecanoyl-Gln$^{B3}$-des(B30)-human insulin.

In certain embodiments, an insulin molecule of the present disclosure comprises the mutations and/or chemical modifications of one of the following insulin molecules: N$^{εB29}$-tridecanoyl-Gly$^{A21}$-human insulin, N$^{εB29}$-tetradecanoyl-Gly$^{A21}$-human insulin, N$^{εB29}$-decanoyl-Gly$^{A21}$-human insulin, N$^{εB29}$-dodecanoyl-Gly$^{A21}$-human insulin, N$^{εB29}$-tridecanoyl-Ala$^{A21}$-human insulin, N$^{εB29}$-tetradecanoyl-Ala$^{A21}$-human insulin, N$^{εB29}$-decanoyl-Ala$^{A21}$-human insulin, N$^{εB29}$-dodecanoyl-Ala$^{A21}$-human insulin.

In certain embodiments, an insulin molecule of the present disclosure comprises the mutations and/or chemical modifications of one of the following insulin molecules: N$^{εB29}$-tridecanoyl-Gly$^{A21}$Gln$^{B3}$-human insulin, N$^{εB29}$-tetradecanoyl-Gly$^{A21}$Gln$^{B3}$-human insulin, N$^{εB29}$-decanoyl-Gly$^{A21}$Gln$^{B3}$-human insulin, N$^{εB29}$-dodecanoyl-Gly$^{A21}$Gln$^{B3}$-human insulin, N$^{εB29}$-tridecanoyl-Ala$^{A21}$Gln$^{B3}$-human insulin, N$^{εB29}$-tetradecanoyl-Ala$^{A21}$Gln$^{B3}$-human insulin, N$^{εB29}$-decanoyl-Ala$^{A21}$Gln$^{B3}$-human insulin, N$^{εB29}$-dodecanoyl-Ala$^{A21}$Gln$^{B3}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$-human insulin, $N^{\epsilon B29}$-tetradecanoyl-Gln$^{B3}$-human insulin, $N^{\epsilon B29}$-decanoyl-Gln$^{B3}$-human insulin, $N^{\epsilon B29}$-dodecanoyl-Gln$^{B3}$-human insulin.

In certain embodiments, an insulin molecule of the present disclosure comprises the mutations and/or chemical modifications of one of the following insulin molecules: $N^{\epsilon B29}$-tridecanoyl-Glu$^{B30}$-human insulin, $N^{\epsilon B29}$-tetradecanoyl-Glu$^{B30}$-human insulin, $N^{\epsilon B29}$-decanoyl-Glu$^{B30}$-human insulin, $N^{\epsilon B29}$-dodecanoyl-Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Glu$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{B30}$-human insulin, $N^{\epsilon B29}$-dodecanoyl-Ala$^{A21}$Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin.

In certain embodiments, an insulin molecule of the present disclosure comprises the mutations and/or chemical modifications of one of the following insulin molecules: $N^{\epsilon B29}$-formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In certain embodiments, an insulin molecule of the present disclosure comprises the mutations and/or chemical modifications of one of the following insulin molecules: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin molecule of the present disclosure comprises the mutations and/or chemical modifications of one of the following insulin molecules: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In certain embodiments, an insulin molecule of the present disclosure comprises the mutations and/or chemical modifications of one of the following insulin molecules: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin molecule of the present disclosure comprises the mutations and/or chemical modifications of one of the following insulin molecules: $N^{\epsilon B29}$-pentanoyl-human insulin, $N^{\alpha B1}$-pentanoyl-human insulin, $N^{\alpha A1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N^{\alpha B1}$-pentanoyl-human insulin.

In certain embodiments, an insulin molecule of the present disclosure comprises the mutations and/or chemical modifications of one of the following insulin molecules: $N^{\epsilon B29}$-hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin molecule of the present disclosure comprises the mutations and/or chemical modifications of one of the following insulin molecules: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In certain embodiments, an insulin molecule of the present disclosure comprises the mutations and/or chemical modifications of one of the following insulin molecules: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin molecule of the present disclosure comprises the mutations and/or chemical modifications of one of the following insulin molecules: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin molecule of the present disclosure comprises the mutations and/or chemical modifications of one of the following insulin molecules: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin molecule of the present disclosure comprises the mutations and/or chemical modifications of one of the following insulin molecules: $N^{\epsilon B28}$-formyl-Lys$^{B28}$Pro$^{B29}$-human insulin, $N^{\alpha B1}$-formyl-Lys$^{B28}$Pro$^{B29}$-human insulin, $N^{\alpha A1}$-formyl-Lys$^{B28}$Pro$^{B29}$-human insulin, $N^{\epsilon B28}$-formyl-$N^{\alpha B1}$-formyl-Lys$^{B28}$Pro$^{B29}$-human insulin, $N^{\epsilon B28}$-formyl-$N^{\alpha A1}$-formyl-Lys$^{B28}$Pro$^{B29}$-human insulin, $N^{\alpha A1}$-formyl-$N^{\alpha B1}$-formyl-Lys$^{B28}$Pro$^{B29}$-human insulin, $N^{\epsilon B28}$-formyl-$N^{\alpha A1}$-formyl-$N^{\alpha B1}$-formyl- Lys$^{B28}$ Pro$^{B29}$-human insulin, N$^{\epsilon B29}$-acetyl-Lys$^{B28}$Pro$^{B29}$-human insulin, N$^{\alpha B1}$-acetyl-Lys$^{B28}$Pro$^{B29}$-human insulin, N$^{\alpha A1}$-acetyl-Lys$^{B28}$Pro$^{B29}$-human insulin, N$^{\epsilon B28}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-acetyl-N$^{\alpha A1}$-acetyl-Lys$^{B28}$Pro$^{B29}$-human insulin, N$^{\alpha A1}$-acetyl-N$^{\alpha B1}$-acetyl-Lys$^{B28}$Pro$^{B29}$-human insulin, N$^{\epsilon B28}$-acetyl-N$^{\alpha A1}$-acetyl-N$^{\alpha B1}$-acetyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-propionyl-Lys$^{B28}$Pro$^{B29}$-human insulin, N$^{\alpha B1}$-propionyl-Lys$^{B28}$Pro$^{B29}$-human insulin, N$^{\alpha A1}$-propionyl-Lys$^{B28}$Pro$^{B29}$-human insulin, N$^{\epsilon B28}$-propionyl-N-propionyl-Lys$^{B28}$Pro$^{B29}$-human insulin, N$^{\epsilon B28}$-propionyl-N$^{\alpha A1}$-propionyl-Lys$^{B28}$Pro$^{B29}$-human insulin, N$^{\alpha A1}$-propionyl-N$^{\alpha B1}$-propionyl-Lys$^{B28}$Pro$^{B29}$-human insulin, N$^{\epsilon B28}$-propionyl-N$^{\alpha A1}$-propionyl-N$^{\alpha B1}$-propionyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-butyryl-Lys$^{B28}$Pro$^{B29}$-human insulin, N$^{\alpha B1}$-butyryl-Lys$^{B28}$Pro$^{B29}$-human insulin, N$^{\alpha A1}$-butyryl-Lys$^{B28}$Pro$^{B29}$-human insulin, N$^{\epsilon B28}$-butyryl-N$^{\alpha B1}$-butyryl-Lys$^{B28}$Pro$^{B29}$-human insulin, N$^{\epsilon B28}$-butyryl-N$^{\alpha A1}$-butyryl-Lys$^{B28}$Pro$^{B29}$-human insulin, N$^{\alpha A1}$-butyryl-N$^{\alpha B1}$-butyryl-Lys$^{B28}$Pro$^{B29}$-human insulin, N$^{\epsilon B28}$-butyryl-N$^{\alpha A1}$-butyryl-N$^{\alpha B1}$-butyryl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-pentanoyl-Lys$^{B28}$Pro$^{B29}$-human insulin, N$^{\alpha B1}$-pentanoyl-Lys$^{B28}$Pro$^{B29}$-human insulin, N$^{\alpha A1}$-pentanoyl-Lys$^{B28}$Pro$^{B29}$-human insulin, N$^{\epsilon B28}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-Lys$^{B28}$Pro$^{B29}$-human insulin, N$^{\alpha A1}$-pentanoyl-N$^{\alpha B1}$-pentanoyl-Lys$^{B28}$Pro$^{B29}$-human insulin, N$^{\epsilon B28}$-pentanoyl-N$^{\alpha A1}$-pentanoyl-N$^{\alpha B1}$-pentanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-hexanoyl-Lys$^{B28}$Pro$^{B29}$-human insulin, N$^{\alpha B1}$-hexanoyl-Lys$^{B28}$Pro$^{B29}$-human insulin, N$^{\alpha A1}$-hexanoyl-Lys$^{B28}$Pro$^{B29}$-human insulin, N$^{\epsilon B28}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-Lys$^{B28}$Pro$^{B29}$-human insulin, N$^{\alpha A1}$-hexanoyl-N$^{\alpha B1}$-hexanoyl-Lys$^{B28}$Pro$^{B29}$-human insulin, N$^{\epsilon B28}$-hexanoyl-N$^{\alpha A1}$-hexanoyl-N$^{\alpha B1}$-hexanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-heptanoyl-Lys$^{B28}$Pro$^{B29}$-human insulin, N$^{\alpha B1}$-heptanoyl-Lys$^{B28}$Pro$^{B29}$-human insulin, N$^{\alpha A1}$-heptanoyl-Lys$^{B28}$Pro$^{B29}$-human insulin, N$^{\epsilon B28}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-Lys$^{B28}$Pro$^{B29}$-human insulin, N$^{\alpha A1}$-heptanoyl-N$^{\alpha B1}$-heptanoyl-Lys$^{B28}$Pro$^{B29}$-human insulin, N$^{\epsilon B28}$-heptanoyl-N$^{\alpha A1}$-heptanoyl-N$^{\alpha B1}$-heptanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-octanoyl-Lys$^{B28}$Pro$^{B29}$-human insulin, N$^{\alpha B1}$-octanoyl-Lys$^{B28}$Pro$^{B29}$-human insulin, N$^{\alpha A1}$-octanoyl-Lys$^{B28}$Pro$^{B29}$-human insulin, N$^{\epsilon B28}$-octanoyl-N$^{\alpha B1}$-octanoyl-Lys$^{B28}$Pro$^{B29}$-human insulin, N$^{\epsilon B28}$-Octanoyl-N$^{\alpha A1}$-octanoyl-Lys$^{B28}$Pro$^{B29}$-human insulin, N$^{\alpha A1}$-octanoyl-N$^{\alpha B1}$-octanoyl-Lys$^{B28}$Pro$^{B29}$-human insulin, N$^{\epsilon B28}$-octanoyl-N$^{\alpha A1}$-octanoyl-N$^{\alpha B1}$-octanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-nonanoyl-Lys$^{B28}$Pro$^{B29}$-human insulin, N$^{\alpha B1}$-nonanoyl-Lys$^{B28}$Pro$^{B29}$-human insulin, N$^{\alpha A1}$-nonanoyl-Lys$^{B28}$Pro$^{B29}$-human insulin, N$^{\epsilon B28}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-Lys$^{B28}$Pro$^{B29}$-human insulin, N$^{\alpha A1}$-nonanoyl-N$^{\alpha B1}$-nonanoyl-Lys$^{B28}$Pro$^{B29}$-human insulin, N$^{\epsilon B28}$-nonanoyl-N$^{\alpha A1}$-nonanoyl-N$^{\alpha B1}$-nonanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B28}$-decanoyl-Lys$^{B28}$Pro$^{B29}$-human insulin, N$^{\alpha B1}$-decanoyl-Lys$^{B28}$Pro$^{B29}$-human insulin, N$^{\alpha A1}$-decanoyl-Lys$^{B28}$Pro$^{B29}$-human insulin, N$^{\epsilon B28}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-Lys$^{B28}$Pro$^{B29}$-human insulin, N$^{\alpha A1}$-decanoyl-N$^{\alpha B1}$-decanoyl-Lys$^{B28}$Pro$^{B29}$-human insulin, N$^{\epsilon B28}$-decanoyl-N$^{\alpha A1}$-decanoyl-N$^{\alpha B1}$-decanoyl-Lys$^{B28}$Pro$^{B29}$-human insulin.

In certain embodiments, an insulin molecule of the present disclosure comprises the mutations and/or chemical modifications of one of the following insulin molecules: N$^{\epsilon B29}$-pentanoyl-Gly$^{A21}$Arg$^{B31}$Arg$^{B32}$-human insulin, N$^{\alpha B1}$-hexanoyl-Gly$^{A21}$Arg$^{B31}$Arg$^{B32}$-human insulin, N$^{\alpha A1}$-heptanoyl-Gly$^{A21}$Arg$^{B31}$Arg$^{B32}$-human insulin, N$^{\epsilon B29}$-octanoyl-N$^{\alpha B1}$-octanoyl-Gly$^{A21}$Arg$^{B31}$Arg$^{B32}$-human insulin, N$^{\epsilon B29}$-propionyl-N$^{\alpha A1}$-propionyl-Gly$^{A21}$Arg$^{B31}$Arg$^{B32}$-human insulin, N$^{\alpha A1}$-acetyl-N$^{60\,B1}$-acetyl-Gly$^{A21}$Arg$^{B31}$Arg$^{B32}$-human insulin, N$^{\epsilon B29}$-formyl-N$^{\alpha A1}$-formyl-N$^{\alpha B1}$-formyl-Gly$^{A21}$Arg$^{B31}$Arg$^{B32}$-human insulin, N$^{\epsilon B29}$-formyl-des(B26)-human insulin, N$^{\alpha B1}$-acetyl-Asp$^{B28}$-human insulin, N$^{\epsilon B29}$-propionyl-N$^{\alpha A1}$-propionyl-N$^{60\;B1}$-propionyl-Asp$^{B1}$Asp$^{B3}$Asp$^{B21}$-human insulin, N$^{\epsilon B29}$-pentanoyl-Gly$^{A21}$-human insulin, N$^{\alpha B1}$-hexanoyl-Gly$^{A21}$-human insulin, N$^{\alpha A1}$-heptanoyl-Gly$^{A21}$-human insulin, N$^{\epsilon B29}$-octanoyl-N$^{\alpha B1}$-octanoyl-Gly$^{A21}$-human insulin, N$^{\epsilon B29}$-propionyl-N$^{\alpha A1}$-propionyl-Gly$^{A21}$-human insulin, N$^{\alpha A1}$-acetyl-N$^{\alpha B1}$-acetyl-Gly$^{A21}$-human insulin, N$^{\epsilon B29}$-formyl-N$^{\alpha A1}$-formyl-N$^{\alpha B1}$-formyl-Gly$^{A21}$-human insulin, N$^{\epsilon B29}$-butyryl-des(B30)-human insulin, N$^{\alpha B1}$-butyryl-des(B30)-human insulin, N$^{\alpha A1}$-butyryl-des(B30)-human insulin, N$^{\epsilon B29}$-butyryl-N$^{60\;B1}$-butyryl-des(B30)-human insulin, N$^{\epsilon B29}$-butyryl-N$^{\alpha A1}$-butyryl-des(B30)-human insulin, N$^{\alpha A1}$-butyryl-N$^{\alpha B1}$-butyryl-des(B30)-human insulin, N$^{\epsilon B29}$-butyryl-N$^{\alpha A1}$-butyryl-N$^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise any one of the aforementioned mutations and/or chemical modifications.

These and other modified insulin molecules are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011, 007; 5,866,538; and 5,750,497, the entire disclosures of which are hereby incorporated by reference.

In various embodiments, an insulin molecule of the present disclosure includes the three wild-type disulfide bridges (i.e., one between position 7 of the A-chain and position 7 of the B-chain, a second between position 20 of the A-chain and position 19 of the B-chain, and a third between positions 6 and 11 of the A-chain).

Methods for conjugating drugs including insulin molecules are described below. In certain embodiments, an insulin molecule is conjugated to the conjugate framework via the A1 amino acid residue. In certain embodiments the A1 amino acid residue is glycine. It is to be understood however, that the present disclosure is not limited to N-terminal conjugation and that in certain embodiments an insulin molecule may be conjugated via a non-terminal A-chain amino acid residue. In particular, the present disclosure encompasses conjugation via the epsilon-amine group of a lysine residue present at any position in the A-chain (wild-type or introduced by site-directed mutagenesis). It will be appreciated that different conjugation positions on the A-chain may lead to different reductions in insulin activity. In certain embodiments, an insulin molecule is conjugated to the conjugate framework via the B1 amino acid residue. In certain embodiments the B1 amino acid residue is phenylalanine It is to be understood however, that the present disclosure is not limited to N-terminal conjugation and that in certain embodiments an insulin molecule may be conjugated via a non-terminal B-chain amino acid residue. In particular, the present disclosure encompasses conjugation via the epsilon-amine group of a lysine residue present at any position in the B-chain (wild-type or introduced by site-directed mutagenesis). For example, in certain embodiments an insulin molecule may be conjugated via the B29 lysine residue. In the case of insulin glulisine, conjugation to the conjugate framework via the B3 lysine residue may be employed. It will be appreciated that different conjugation positions on the B-chain may lead to different reductions in insulin activity.

In certain embodiments, the ligands are conjugated to more than one conjugation point on a drug such as an insulin molecule. For example, an insulin molecule can be conjugated at both the A1 N-terminus and the B29 lysine. In some embodiments, amide conjugation takes place in carbonate buffer to conjugate at the B29 and A1 positions, but not at the B1 position. In other embodiments, an insulin molecule can be conjugated at the A1 N-terminus, the B1 N-terminus, and the B29 lysine. In yet other embodiments, protecting groups are used such that conjugation takes place at the B1 and B29 or B1 and A1 positions. It will be appreciated that any combination of conjugation points on an insulin molecule may be employed. In some embodiments, at least one of the conjugation points is a mutated lysine residue, e.g., $Lys^{43}$.

In various embodiments, a conjugate may include an insulin sensitizer (i.e., a drug which potentiates the action of insulin). Drugs which potentiate the effects of insulin include biguanides (e.g., metformin) and glitazones. The first glitazone drug was troglitazone which turned out to have severe side effects. Second generation glitazones include pioglitazone and rosiglitazone which are better tolerated although rosiglitazone has been associated with adverse cardiovascular events in certain trials.

In various embodiments, a conjugate may include an insulin secretagogue (i.e., a drug which stimulates insulin secretion by beta cells of the pancreas). For example, in various embodiments, a conjugate may include a sulfonylurea. Sulfonylureas stimulate insulin secretion by beta cells of the pancreas by sensitizing them to the action of glucose. Sulfonylureas can, moreover, inhibit glucagon secretion and sensitize target tissues to the action of insulin. First generation sulfonylureas include tolbutamide, chlorpropamide and carbutamide. Second generation sulfonylureas which are active at lower doses include glipizide, glibenclamide, gliclazide, glibornuride and glimepiride. In various embodiments, a conjugate may include a meglitinide. Suitable meglitinides include nateglinide, mitiglinide and repaglinide. Their hypoglycemic action is faster and shorter than that of sulfonylureas. Other insulin secretagogues include glucagon-like peptide 1 (GLP-1) and GLP-1 analogs (i.e., a peptide with GLP-1 like bioactivity that differs from GLP-1 by 1-10 amino acid substitutions, additions or deletions and/or by a chemical modification). GLP-1 reduces food intake by inhibiting gastric emptying, increasing satiety through central actions and by suppressing glucagon release. GLP-1 lowers plasma glucose levels by increasing pancreas islet cell proliferation and increases insulin production following food consumption. GLP-1 may be chemically modified, e.g., by lipid conjugation as in liraglutide to extend its in vivo half-life. Yet other insulin secretagogues include exendin-4 and exendin-4 analogs (i.e., a peptide with exendin-4 like bioactivity that differs from exendin-4 by 1-10 amino acid substitutions, additions or deletions and/or by a chemical modification). Exendin-4, found in the venom of the Gila Monster, exhibits GLP-1 like bioactivity. It has a much longer half-life than GLP-1 and, unlike GLP-1, it can be truncated by 8 amino acid residues at its N-terminus without losing bioactivity. The N-terminal region of GLP-1 and exendin-4 are almost identical, a significant difference being the second amino acid residue, alanine in GLP-1 and glycine in exendin-4, which gives exendin-4 its resistance to in vivo digestion. Exendin-4 also has an extra 9 amino acid residues at its C-terminus as compared to GLP-1. Mann et al. *Biochem. Soc. Trans.* 35:713-716, 2007 and Runge et al., *Biochemistry* 46:5830-5840, 2007 describe a variety of GLP-1 and exendin-4 analogs which may be used in a conjugate of the present disclosure. The short half-life of GLP-1 results from enzymatic digestion by dipeptidyl peptidase IV (DPP-IV). In certain embodiments, the effects of endogenous GLP-1 may be enhanced by administration of a DPP-IV inhibitor (e.g., vildagliptin, sitagliptin, saxagliptin, linagliptin or alogliptin).

In various embodiments, a conjugate may include amylin or an amylin analog (i.e., a peptide with amylin like bioactivity that differs from amylin by 1-10 amino acid substitutions, additions or deletions and/or by a chemical modification). Amylin plays an important role in glucose regulation (e.g., see Edelman and Weyer, *Diabetes Technol. Ther.* 4:175-189, 2002). Amylin is a neuroendocrine hormone that is co-secreted with insulin by the beta cells of the pancreas in response to food intake. While insulin works to regulate glucose disappearance from the bloodstream, amylin works to help regulate glucose appearance in the bloodstream from the stomach and liver. Pramlintide acetate (SYMLIN®) is an exemplary amylin analog. Since native human amylin is amyloidogenic, the strategy for designing pramlintide involved substituting certain residues with those from rat amylin, which is not amyloidogenic. In particular, proline residues are known to be structure-breaking residues, so these were directly grafted from the rat sequence into the human sequence. Glu-10 was also substituted with an asparagine.

In various embodiments, a pre-conjugated drug may contain one or more reactive moieties (e.g., carboxyl or reactive ester, amine, hydroxyl, aldehyde, sulthydryl, maleimidyl, alkynyl, azido, etc. moieties). As discussed below, these reactive moieties may, in certain embodiments, facilitate the conjugation process. Specific examples include peptidic drugs bearing alpha-terminal amine and/or epsilon-amine lysine groups. It will be appreciated that any of these reactive moieties may be artificially added to a known drug if not already present. For example, in the case of peptidic drugs a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

As discussed above, the present disclosure is not limited to any particular combination of drug and target molecule.

In various embodiments, a material of the present disclosure may be exploited to manipulate a natural feedback mechanism. For example, there are many natural feedback mechanisms (including most hormonal control mechanisms) in which the level of two endogenous substances are interrelated (e.g., glucose and insulin where the level of insulin increases as the level of glucose increases and the level of glucose decreases as the level of insulin increases). In such embodiments one of the endogenous substances can become the target molecule (e.g., glucose) while the other becomes the drug (e.g., insulin). Alternatively, in various embodiments, the drug can be a molecule that (a) has the same function as the other endogenous substance (e.g., reduces glucose levels), (b) stimulates the production of the other endogenous substance and/or (c) potentiates the effect(s) of the other endogenous substance. For example, when glucose is the target molecule one could use an insulin secretagogue or an insulin sensitizer instead of insulin as the drug.

Other non-limiting examples of artificial feedback systems, include, a material which releases glucagon conjugates in response to high levels of insulin, a material which releases anticoagulant conjugates (e.g., coumarines such as warfarin, acenocoumarol, phenprocoumon and phenindione, heparin, direct thrombin inhibitors such as argatroban, lepirudin, bivalirudin, and dabigatran, etc.) in response to thrombosis indicators; a material which releases lactate-lowering drug conjugates (e.g., dichloroacetate) in response to increased lactate levels; etc.

In various embodiments, a material can be designed to release conjugates which include a drug with a function that is not directly related to the target molecule. Without limitation, a material which responds to a target molecule which increases in concentration after a meal (e.g., glucose) may be used to provide long-term, mealtime dosing of a drug. Any drug which needs to be dosed periodically and/or with food would benefit from such a delivery system. As is well known in the art, many traditional drugs need to be administered with food or at mealtimes. For example, drugs which inhibit the absorption of fats (e.g., orlistat) are advantageously present during mealtime. Similarly, drugs which lower lipid levels, e.g., lovastatin, attorvastatin, or simvastatin, or triglyceride levels, e.g., gemfibrozil, may also be advantageously released at mealtimes.

Detectable Label

As noted above, in various embodiments, a conjugate may comprise a detectable label. For example, a detectable label may be included in order to detect the location of conjugates within an organism, tissue or cell; when the conjugates are used in a sensor; etc. It is to be understood that a conjugate can comprise any detectable label known in the art. A conjugate can comprise more than one copy of the same label and/or can comprise more than one type of label. In general, the label(s) used will depend on the end application and the method used for detection.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, γ-phthalaldehyde, fluorescamine, etc. are all exemplary fluorescent labels. Chemiluminescent labels, i.e., labels that are capable of converting a secondary substrate to a chromogenic product are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase, acetylcholinesterase, luciferin, luciferase, aequorin and the like are all exemplary protein based chemiluminescent labels. Luminol, isoluminol, theromatic acridinium ester, imidazole, acridinium salt, oxalate ester, etc. are exemplary non-protein based chemiluminescent labels. Another non-limiting and commonly used example of an indirectly detectable label is an affinity ligand, i.e., a label with strong affinity for a secondary binding partner (e.g., an antibody or aptamer) which may itself be directly or indirectly detectable.

In general, a detectable label may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In various embodiments, a pre-conjugated label may contain one or more reactive moieties (e.g., carboxyl or reactive ester, amine, hydroxyl, aldehyde, sulthydryl, maleimidyl, alkynyl, azido, etc. moieties). As discussed below, these reactive moieties may, in certain embodiments, facilitate the conjugation process. Specific examples include peptidic labels bearing alpha-terminal amine and/or epsilon-amine lysine groups. It will be appreciated that any of these reactive moieties may be artificially added to a known label if not already present. For example, in the case of peptidic labels a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

Conjugate Framework

Conjugates can be prepared from frameworks that naturally include affinity ligands (e.g., polysaccharides such as glycogen and dextran naturally include glucose affinity ligands) and/or by artificially incorporating affinity ligands into a natural or synthetic framework. It is to be understood that the conjugates of the present disclosure are not limited to a particular framework. For example, conjugates may be prepared using frameworks that include polymeric and/or non-polymeric structures. It is also to be understood that the conjugate frameworks may be linear, branched, hyperbranched and/or a combination of these. The following section describes some exemplary conjugate frameworks.

In various embodiments, a conjugate may be prepared from a framework that includes a polymeric structure. For example, a polymer with pendant reactive groups (e.g., carboxyl or reactive ester, amine, hydroxyl, aldehyde, sulfhydryl, maleimidyl, alkynyl, azido, etc.) may be employed. It will be appreciated that different pendant groups may be mixed in a single framework (e.g., by co-polymerizing appropriate monomers in desired ratios to produce a polymeric framework). As discussed below, these reactive groups may be used to attach affinity ligands, drugs and/or detectable labels to the framework. Co-polymers, mixtures, and adducts of different frameworks may also be used. Such combinations may be useful for optimizing the mechanical and chemical properties of a material.

In various embodiments, frameworks having carboxyl (or reactive ester) pendant groups (—COOH bearing frameworks, or CBFs) may be used. Such frameworks may naturally include carboxyl groups or may be modified to include them. Exemplary polymeric CBFs include but are not limited to carboxylated polysaccharides (CPS) such as alginate (Ag), carboxymethylated-D-manno-D-glucan (CMMG, available from Daiichi Pharmaceutical Co.), carboxymethyldextran (CMDex), carboxymethylchitin (CMCh, available from Katakura Chikkalin Co.), N-desulfated N-acetylated heparin (DSH), and hyaluronic acid (HA). DSH and CMDex may be synthesized according to Sugahara, et al., Biol. Pharm. Bull., 24, 535-543 (2001). In general, hydroxylated frameworks may be carboxylated through reaction with chloroacetic acid under basic conditions. In the case of a polymeric framework the degree of carboxyl substitution with respect to monomer may vary between 1 and 100 mol %. Naturally occurring carboxylated polymers include but are not limited to carboxylated poly(amino acids) (CPAA) such as poly-L-glutamate and poly-L-aspartate. The carboxylate content may be varied between 1 and 100% mol COOH/mol AA residue by copolymerizing carboxylated amino acids (e.g., amino acids with a carboxyl group in addition to the carboxyl group which becomes part of the polymer backbone) with non-carboxylated amino acids (e.g., amino acids whose only carboxyl group becomes part of the polymer backbone).

In various embodiments, frameworks having amine pendant groups (—NH$_2$ bearing frameworks, or NBFs) may be used. Such frameworks may be naturally occurring or may be chemically modified to include a primary amine. The latter include but are not limited to polymeric frameworks, e.g., amine pendant polysaccharides (NPS) such as deacetylated chitosan (Ch) (Sigma Aldrich, Milwaukee, Wis.) and diethylaminoethyl ether dextran (DEAEDex), MW 500,000 g/mol (Polysciences, Warrington, Pa.). In the case of such polymeric frameworks the degree of amine substitution with respect to monomer may vary between 1 and 100 mol %. Other suitable NBFs include, but are not limited to, polynucleotides where one or more of the purine bases has been derivatized with an amine group at the 2' location. Naturally occurring aminated polymers include but are not limited to poly(amino acids) such as poly-L-lysine (PLL) and its enantiomer. The amine content may be varied between 1 and 100% mol NH$_2$/mol amino acid residue by copolymerizing an aminated amino acid (e.g., an amino acid with an amine in addition to the amine group that eventually becomes part of the polymer backbone) with non-aminated amino acids (e.g., an amino acid whose only amine is that which eventually becomes part of the polymer backbone).

In various embodiments, polymers having hydroxyl pendant groups (—OH bearing frameworks, or OBFs) may be used. Such frameworks may be naturally hydroxylated or may be chemically modified to include a hydroxyl group. In addition to dextran, naturally occurring polymeric OBFs include but are not limited to polysaccharides such as yeast mannan (Mn), pullulan (Pl), amylose (Am), amylopectin (AmP), glycogen (Gl), cellulose (Cl), hyaluronate (Hy), chondroitin (ChD), and dextrin (Dx), all of which may be obtained commercially from Sigma Aldrich. In addition, poly (amino acids) such as poly(serine), poly(threonine), poly(tyrosine), and poly(4-hydroxyproline) may also be employed as hydroxylated polymers. The hydroxyl content of the poly (amino acids) may be varied between 1 and 100% mol —OH/mol amino acid residue by co-polymerizing hydroxylated amino acids with non-hydroxylated amino acids. Of course, carboxyl (or reactive ester), amino, and hydroxyl pendant groups may be mixed in a single polymer by co-polymerizing the appropriate amino acids in desired ratios.

In various embodiments, frameworks having sulfhydryl pendant groups (—SH bearing frameworks, or SBFs) may be used. SBFs may be naturally sulfhydrylated or may be chemically modified using standard organic chemistry techniques to include a sulfhydryl group. In other embodiments, frameworks having aldehyde, maleimidyl, alkynyl, azido, etc. pendant groups may be used.

In addition to the aforementioned classes of frameworks, some exemplary polymers that may be used include poly (lactic acid) (PLA), poly(glycolic acid) (PGA), PLA-PGA co-polymers (PLGA), poly(anhydrides), poly(hydroxy acids), poly(ortho esters), poly(propylfumerates), poly(caprolactones), polyamides, polyacetals, biodegradable polycyanoacrylates and biodegradable polyurethanes.

In various embodiments, conjugates of the following general formula (I) may be employed:

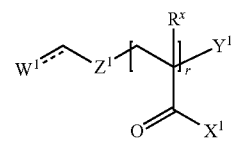

I

Various embodiments of the conjugates of formula (I) are described in more detail in Example 12; however, in general it is to be understood that $R^x$ is hydrogen or optionally substituted $C_{1-6}$ alkyl;

$Z^1$ is an optionally substituted bivalent $C_{1-10}$ hydrocarbon chain, wherein 1, 2, 3, 4 or 5 methylene units of $Z^1$ are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety, wherein R$^a$ is hydrogen, optionally substituted aliphatic, optionally substituted heteroaliphatic, optionally substituted aryl, optionally substituted heteroaryl, or a suitable amino protecting group; and R$^b$ is hydrogen, optionally substituted aliphatic, optionally substituted heteroaliphatic, optionally substituted aryl, or optionally substituted heteroaryl;

each occurrence of $X^1$ is independently —OR$^c$ or —N(R$^d$)$_2$, wherein R$^c$ is hydrogen, optionally substituted aliphatic, optionally substituted heteroaliphatic, optionally substituted aryl, optionally substituted heteroaryl, a suitable hydroxyl protecting group, a cation group, or an affinity ligand, and each R$^d$ is, independently, hydrogen, optionally substituted aliphatic, optionally substituted heteroaliphatic, optionally substituted aryl, optionally substituted heteroaryl, a suitable amino protecting group, or an affinity ligand, with the proviso that at least two occurrences of $X^1$ include an affinity ligand;

$Y^1$ is hydrogen, halogen, optionally substituted aliphatic, optionally substituted heteroaliphatic, optionally substituted aryl, optionally substituted heteroaryl, —OR$^e$ or —SR$^e$ wherein R$^e$ is hydrogen, optionally substituted aliphatic, optionally substituted heteroaliphatic, optionally substituted aryl, or optionally substituted heteroaryl;

r is an integer between 5-25, inclusive;

$W^1$ is a drug; and

------ corresponds to a single or double covalent bond.

In various embodiments, conjugates of the following general formula (II) may be employed:

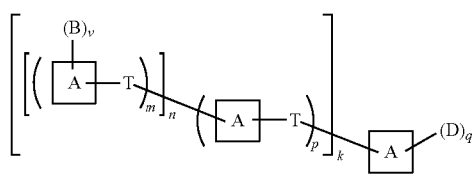

II wherein:

each occurrence of [(Ⓐ—T)] represents a potential branch within the conjugate;

each occurrence of (Ⓐ—T) represents a potential repeat within a branch of the conjugate;

each occurrence of Ⓐ is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently an affinity ligand;

each occurrence of $L^B$ is independently a covalent bond or a group derived from the covalent conjugation of a T with an X;

-D is -T-$L^D$-W;

each occurrence of W is independently a drug or a detectable label;

each occurrence of $L^D$ is independently a covalent bond or a group derived from the covalent conjugation of a T with a W;

k is an integer from 2 to 11, inclusive, defining at least two k-branches within the conjugate;

q is an integer from 1 to 4, inclusive;

k+q is an integer from 3 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

It is to be understood that general formula (II) (and other formulas herein) does not expressly list every hydrogen. For example, if the central Ⓐ is a $C_6$ aryl group and k+q<6 it will be appreciated that the open position(s) on the $C_6$ aryl ring include a hydrogen.

In general, it will be appreciated that each occurrence of Ⓐ represents a potential branching node and that the number of branches at each node are determined by the values of k for the central Ⓐ and n for non-central occurrences of Ⓐ. Since k≥2 the conjugate will always include at least two k-branches. One of ordinary skill will appreciate that because each occurrence of n may be an integer from 0 to 5, the present disclosure contemplates both branched and hyperbranched (e.g., dendrimer-like) embodiments of these conjugates. The proviso which requires that within each k-branch at least one occurrence of n is ≥1 and at least one occurrence of v is ≥1 ensures that every conjugate includes at least two separate k-branches with an occurrence of B (i.e., an affinity ligand).

In certain embodiments, each occurrence of Ⓐ in a p-bracketed moiety is substituted by a number of n-bracketed moieties corresponding to a value of n≥1. For example, when k=2 and p=2 in both k-branches, the conjugate may be of the formula (IIa):

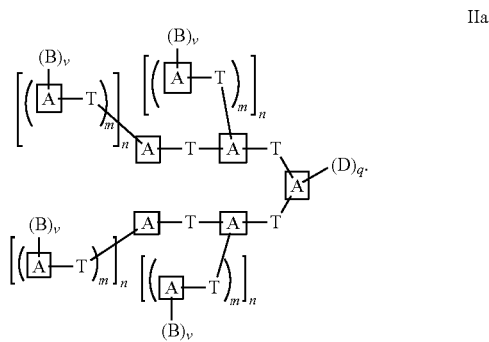

IIa

In other embodiments, only terminal occurrences of Ⓐ in a p-bracketed moiety are substituted by a number of n-bracketed moieties corresponding to a value of n≥1. For example, when k=2 and p=2 in both k-branches (and n=0 for the first p-bracketed moiety in both k-branches), the conjugate may be of the formula (IIb):

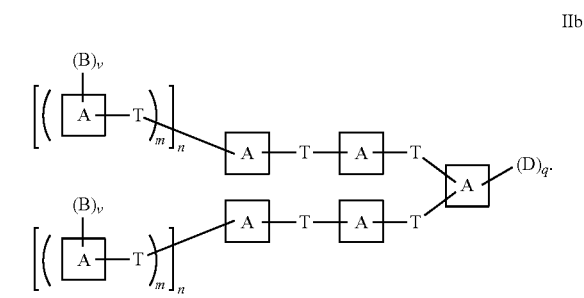

IIb

In certain embodiments, each occurrence of Ⓐ in an m-bracketed moiety is substituted by a number of B moieties corresponding to the value of v≥1. For example, when k=2, each occurrence of p=1, and each occurrence of m=2, the conjugate may be of the formula (IIc):

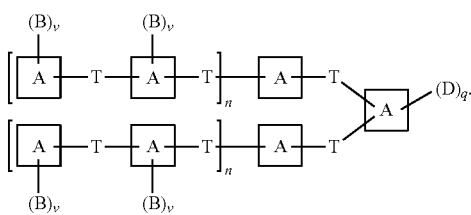

IIc

In other embodiments, only terminal occurrences of [A] in an m-bracketed moiety are substituted by a number of B moieties corresponding to a value of v≥1. For example, when k=2, each occurrence of p=1, and each occurrence of m=2 (and v=0 for the first m-bracketed moiety in each n-branch), the conjugate may be of the formula (IId):

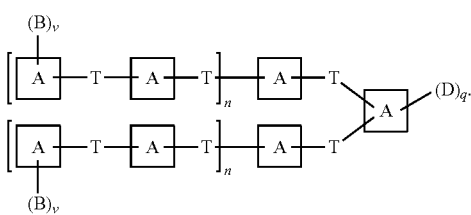

IId

By way of further example, when q=1 and n=1 in both k-branches of the previous formula, the conjugate may be of the formula (IIe):

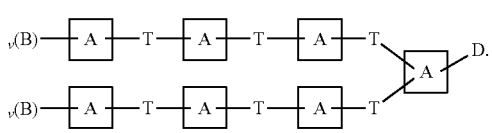

IIe

Alternatively, when q=1 and n=2 in both k-branches of the previous formula, the conjugate may be of the formula (IIf):

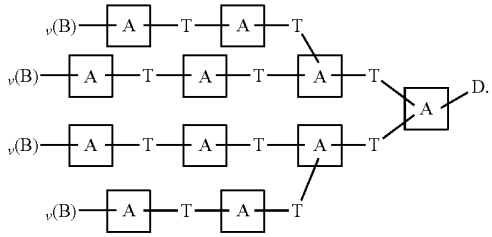

IIf

In various embodiments, the present disclosure also provides conjugates which include affinity ligands and/or a drug or detectable label which are non-covalently bound the conjugate framework.

For example, in some embodiments, the present disclosure provides conjugates of any of the foregoing formulas, wherein:
each of [A], T, D, k, q, k+q, p, n, m and v is defined as described above and herein;
—B is -T-LRP$^B$-X;
each occurrence of X is independently an affinity ligand; and
each occurrence of LRP$^B$ is independently a ligand-receptor pair which forms a non-covalent bond between T and X with a dissociation constant in human serum of less than 1 pmol/L.

In yet other embodiments, the present disclosure provides conjugates of any of the foregoing formulas, wherein:

each of [A], T, B, k, q, k+q, p, n, m and v is defined as described above and herein;
-D is -T-LRP$^D$-W;
each occurrence of W is independently a drug or a detectable label; and
each occurrence of LRP$^D$ is independently a ligand-receptor pair which forms a non-covalent bond between T and W with a dissociation constant in human serum of less than 1 pmol/L.

In other embodiments, the present disclosure provides conjugates of any of the foregoing formulas wherein:
each of [A], T, k, q, k+q, p, n, m and v is defined as described above and herein;
—B is -T-LRP$^B$-X;
each occurrence of X is independently an affinity ligand;
each occurrence of LRP$^B$ is independently a ligand-receptor pair which forms a non-covalent bond between T and X with a dissociation constant in human serum of less than 1 pmol/L.
-D is -T-LRP$^D$-W;
each occurrence of W is independently a drug or a detectable label; and
each occurrence of LRP$^D$ is independently a ligand-receptor pair which forms a non-covalent bond between T and W with a dissociation constant in human serum of less than 1 pmol/L.

In various embodiments, a conjugate of the present disclosure may have the general formula (III):

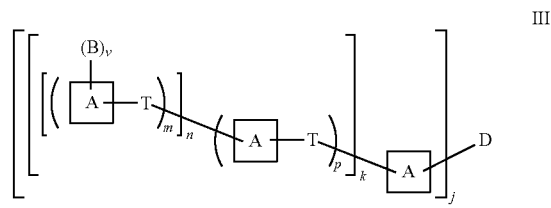

III wherein [A], B, T, D, v, m, n, and p are as defined and described herein, k is an integer from 1 to 11, inclusive, and j is an integer from 2 to 4, inclusive. Conjugates of formula (III) may have multiple sites of conjugation of ligand to drug. It will be appreciated that, when q is 1, similar subgenera described to those described above (formulae (IIa) to (IIf)) can be contemplated by one skilled in the art for conjugates of formula (III) wherein j is 2, 3, or 4.

For purposes of exemplification and for the avoidance of confusion it is to be understood that an occurrence of: -[A]-D-[A]- in a conjugate of formula (III) (i.e., when j is 2) could be represented as: -[A]-T-L$^D$-L$^D$-T-[A]- (when the drug is covalently bound to the conjugate framework) or -[A]-T-LRP$^D$-W-LRP$^D$-T-[A]- (when the drug is non-covalently bound to the conjugate framework).

Description of Exemplary Groups

[A] (Node)

In certain embodiments, each occurrence of [A] is independently an optionally substituted group selected from the group consisting of acyl, aliphatic, heteroaliphatic, awl, heteroaryl, and heterocyclic. In some embodiments, each occurrence of [A] is the same. In some embodiments, the central [A] is different from all other occurrences of [A]. In certain embodiments, all occurrences of [A] are the same except for the central [A].

In some embodiments, [A] is an optionally substituted awl or heteroaryl group. In some embodiments, [A] is 6-membered aryl. In certain embodiments, [A] is phenyl.

In certain embodiments, [A] is a heteroatom selected from N, O, or S. In some embodiments, [A] is nitrogen atom. In some embodiments, A is an oxygen atom. In some embodiments, A is sulfur atom. In some embodiments, A is a carbon atom.

T (Spacer)

In certain embodiments, each occurrence of T is independently a bivalent, straight or branched, saturated or unsaturated, optionally substituted $C_{1-20}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an awl group, or a heteroaryl group. In certain embodiments, one, two, three, four, or five methylene units of T are optionally and independently replaced. In certain embodiments, T is constructed from a $C_{1-10}$, $C_{1-8}$, $C_{1-6}$, $C_{1-4}$, $C_{2-12}$, $C_{4-12}$, $C_{6-12}$, $C_{8-12}$, or $C_{10-12}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group. In some embodiments, one or more methylene units of T is replaced by a heterocyclic group. In some embodiments, one or more methylene units of T is replaced by a triazole moiety. In certain embodiments, one or more methylene units of T is replaced by —C(O)—. In certain embodiments, one or more methylene units of T is replaced by —C(O)N(R)—. In certain embodiments, one or more methylene units of T is replaced by —O—.

In some embodiments, T is

In some embodiments, T is

In some embodiments, T is

In some embodiments, T is

In some embodiments, T is

In some embodiments, T is

In certain embodiments, each occurrence of T is the same.

In certain embodiments, each occurrence of T (outside groups B and D) is a covalent bond and the conjugate is of the general formula (V) or (VI):

wherein A, B, D, v, m, n, p, k, and j are as defined and described for formula (II) or (III), respectively.

In certain embodiments of general formulae (V) and (VI), each occurrence of A except for the central A is a covalent bond, each occurrence of v=1, and the conjugate is of the formula (VII) or (VIII):

wherein A, B, D, q, k, and j are as defined and described for formula (II) or (III), respectively.

In certain such embodiments for formula (VII), k=2 and q=1.
In other embodiments, k=3 and q=1.
In other embodiments, k=2 and q=2.
In certain such embodiments for formula (VIII), k=1 and j=2.
In other embodiments, k=2 and j=2.
In other embodiments, k=3 and j=2.
In other embodiments, k=1 and j=3.
In other embodiments, k=2 and j=3.
In other embodiments, k=3 and j=3.

In some embodiments, the present disclosure provides conjugates of general formula (VIIa):

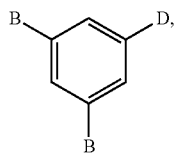

VIIa wherein B and D are as defined and described herein.

For example, in some embodiments, the present disclosure provides conjugates of formula:

In some embodiments, the present disclosure provides conjugates of general formula (VIIb):

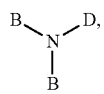

VIIb wherein B and D are as defined and described herein.

For example, in some embodiments, the present disclosure provides conjugates of formula:

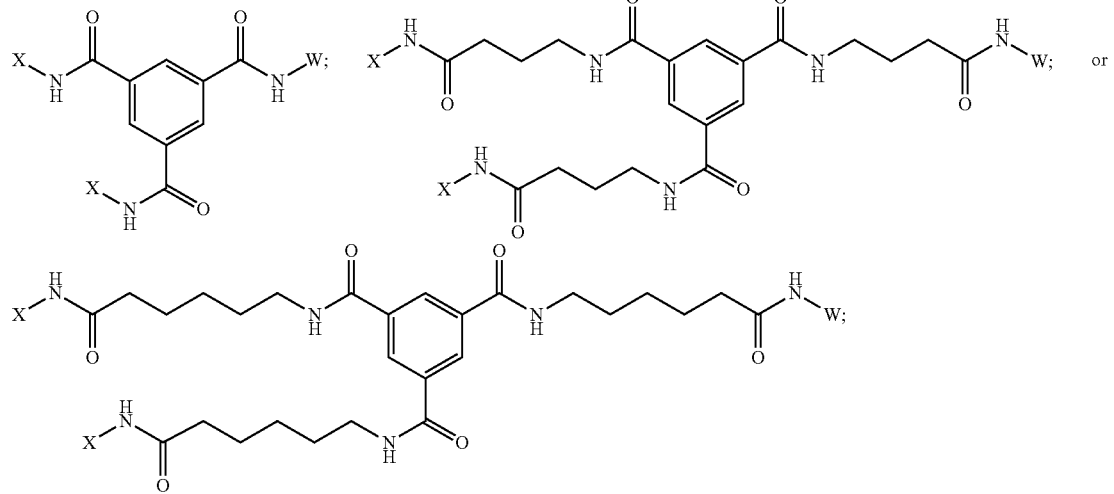

wherein W and X is as defined and described herein.

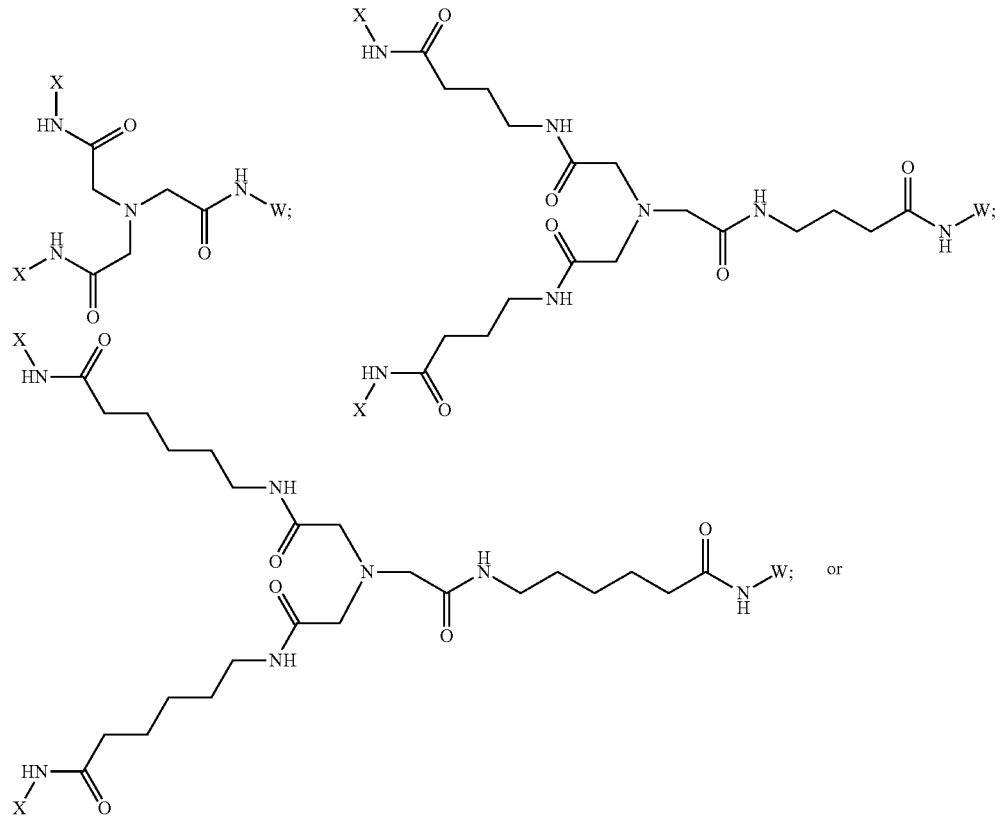

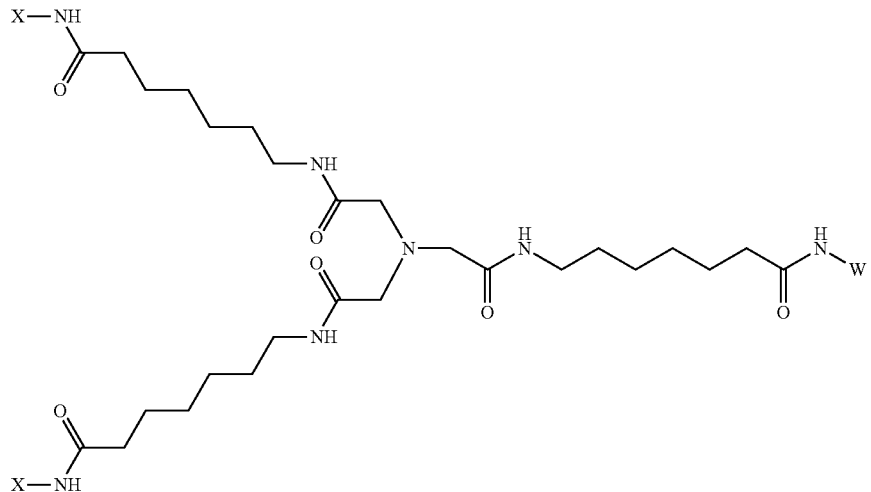

wherein W and X are as defined and described herein.

In some embodiments, the present disclosure provides conjugates of general formula (VIIc):

VIIc wherein B and D are as defined and described herein.

For example, in some embodiments, the present disclosure provides conjugates of formula:

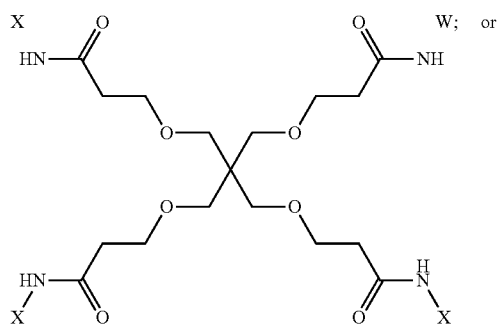

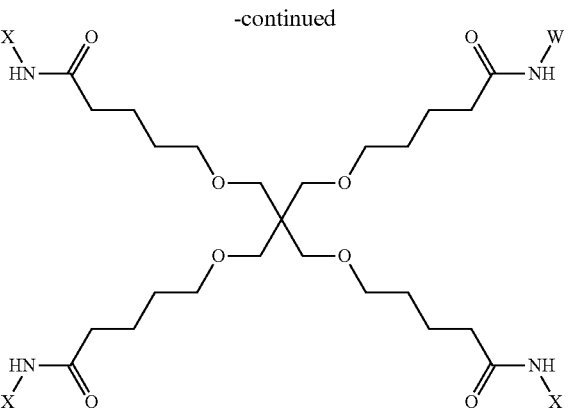

wherein W and X are as defined and described herein.

It will be appreciated that similar subgenera to those of formulae (VIIa), (VIIb), and (VIIc), and species thereof, can be contemplated by one skilled in the art for conjugates of formula (VIII) wherein j is 2, 3, or 4. For example, when j is 2, in certain embodiments, the present disclosure provides conjugates of formula:

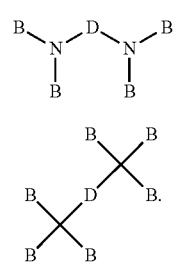

VIIIb-i

VIIIc-i wherein B and D are as defined and described herein.

In certain embodiments, the present disclosure provides conjugates of formula:

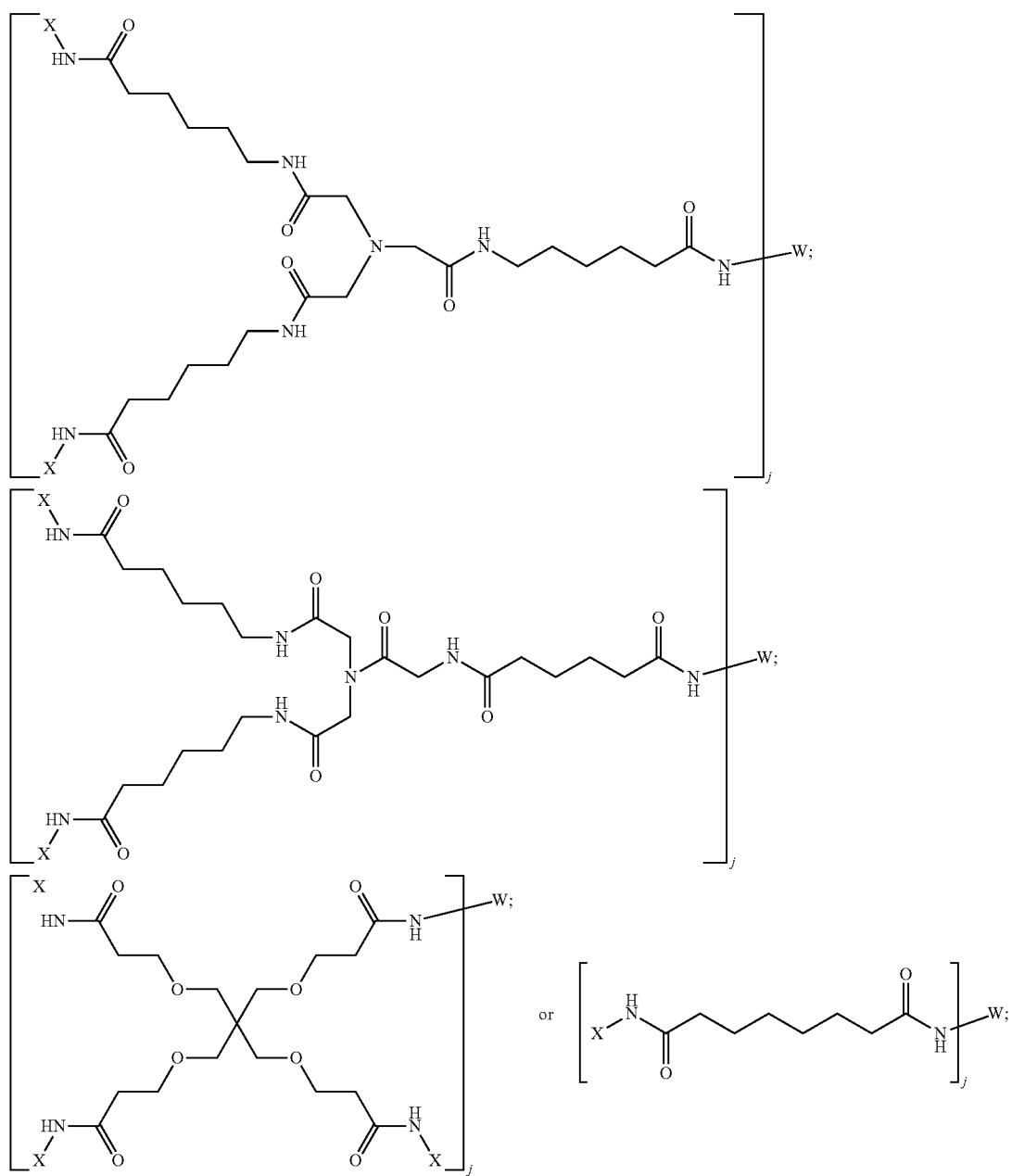

wherein W, X, and j are as defined and described herein.

B (Ligand)

In various embodiments, —B is -T-$L^B$-X where X is a ligand; and $L^B$ is a covalent bond or a group derived from the covalent conjugation of an X with a T. Exemplary ligands and their saccharide components were described above.

D (Drug)

In various embodiments, -D is -T-$L^D$-W where W is a drug and $L^D$ is a covalent bond or a group derived from the covalent conjugation of a W with a T. Exemplary drugs were described above.

D (Detectable Label)

As noted above, in various embodiments, the W in D is a detectable label. For example, a detectable label may be included in order to detect the location of conjugates within an organism, tissue or cell; when the conjugates are used in a sensor; etc. It is to be understood that a conjugate can comprise any detectable label known in the art. A conjugate can comprise more than one copy of the same label and/or can comprise more than one type of label. In general, the label(s) used will depend on the end application and the method used for detection.

The detectable label may be directly detectable or indirectly detectable, e.g., through combined action with one or more additional members of a signal producing system. Examples of directly detectable labels include radioactive, paramagnetic, fluorescent, light scattering, absorptive and colorimetric labels. Fluorescein isothiocyanate, rhodamine, phycoerythrin phycocyanin, allophycocyanin, γ-phthalaldehyde, fluorescamine, etc. are all exemplary fluorescent labels. Chemiluminescent labels, i.e., labels that are capable of converting a secondary substrate to a chromogenic product are examples of indirectly detectable labels. For example, horseradish peroxidase, alkaline phosphatase, glucose-6-phosphate dehydrogenase, malate dehydrogenase, staphylococcal nuclease, delta-V-steroid isomerase, yeast alcohol dehydrogenate, α-glycerophosphate dehydrogenase, triose phosphate isomerase, asparaginase, glucose oxidase, β-galactosidase, ribonuclease, urease, catalase, glucoamylase, acetylcholinesterase, luciferin, luciferase, aequorin and the like are all exemplary protein based chemiluminescent labels. Luminol, isoluminol, theromatic acridinium ester, imidazole, acridinium salt, oxalate ester, etc. are exemplary non-protein based chemiluminescent labels. Another non-limiting and commonly used example of an indirectly detectable label is an affinity ligand, i.e., a label with strong affinity for a secondary binding partner (e.g., an antibody or aptamer) which may itself be directly or indirectly detectable.

In general, a detectable label may be visualized or detected in a variety of ways, with the particular manner of detection being chosen based on the particular detectable label, where representative detection means include, e.g., scintillation counting, autoradiography, measurement of paramagnetism, fluorescence measurement, light absorption measurement, measurement of light scattering and the like.

In various embodiments, a pre-conjugated label may contain one or more reactive moieties (e.g., carboxyl or reactive ester, amine, hydroxyl, aldehyde, sulfhydryl, maleimidyl, alkynyl, azido, etc. moieties). As discussed below, these reactive moieties may, in certain embodiments, facilitate the conjugation process. Specific examples include peptidic labels bearing alpha-terminal amine and/or epsilon-amine lysine groups. It will be appreciated that any of these reactive moieties may be artificially added to a known label if not already present. For example, in the case of peptidic labels a suitable amino acid (e.g., a lysine) may be added or substituted into the amino acid sequence. In addition, as discussed in more detail below, it will be appreciated that the conjugation process may be controlled by selectively blocking certain reactive moieties prior to conjugation.

$L^B$ and $L^D$ (Covalent Conjugation)

One of ordinary skill will appreciate that a variety of conjugation chemistries may be used to covalently conjugate an X with a T and/or a W with a T (generally "components"). Such techniques are widely known in the art, and exemplary techniques are discussed below. Components can be directly bonded (i.e., with no intervening chemical groups) or indirectly bonded through a spacer (e.g., a coupling agent or covalent chain that provides some physical separation between the conjugated element and the remainder of the conjugate framework). It is to be understood that components may be covalently bound to a conjugate framework through any number of chemical bonds, including but not limited to amide, amine, ester, ether, thioether, isourea, imine, etc. bonds. In certain embodiments, $L^B$ and/or $L^D$ (generally "L" for the purposes of this section) is a covalent bond. In some embodiments, L is an optionally substituted moiety derived from conjugating an optionally substituted carbonyl-reactive, thiol-reactive, amine-reactive, or hydroxyl-reactive moiety of T with a carboxyl, thiol, amine, or hydroxyl group of X or W. In some embodiments, L is an optionally substituted moiety derived from conjugating an optionally substituted carboxyl-reactive, thiol-reactive, amine-reactive, or hydroxyl-reactive moiety of X or W with a carboxyl, thiol, amine, or hydroxyl group of T. In some embodiments, L is

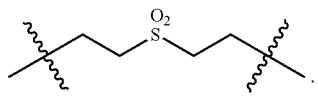 [SMILES: *CCS(=O)(=O)CC*]

In some embodiments, L is a succinimide moiety.

In various embodiments, components may be covalently bound to a conjugate framework using "click chemistry" reactions as is known in the art. These include, for example, cycloaddition reactions, nucleophilic ring-opening reactions, and additions to carbon-carbon multiple bonds (e.g., see Kolb and Sharpless, *Drug Discovery Today* 8:1128-1137, 2003 and references cited therein as well as Dondoni, *Chem. Asian J.* 2:700-708, 2007 and references cited therein). As discussed above, in various embodiments, the components may be bound to a conjugate framework via natural or chemically added pendant groups. In general, it will be appreciated that the first and second members of a pair of reactive groups (e.g., a carboxyl group and an amine group which react to produce an amide bond) can be present on either one of the component and framework (i.e., the relative location of the two members is irrelevant as long as they react to produce a conjugate). Exemplary linkages are discussed in more detail below. In various embodiments, carboxyl (or reactive ester) bearing components can be conjugated to —OH bearing frameworks (OBFs) using the procedure outlined by Kim et al., *Biomaterials* 24:4843-4851 (2003). Briefly, the OBF is dissolved in DMSO along with the carboxyl bearing component and reacted by means of N',N'-dicyclohexylcarbodiimide (DCC) and 4-dimethylaminopyridine (DMAP) as catalysts under a dry atmosphere. Carboxyl bearing components can be conjugated to —NH$_2$ bearing frameworks (NBFs) using a carbodiimide (EDAC) coupling procedure. Using this procedure, the carboxyl bearing component is functionalized by reaction with EDAC in a pH 5 buffer followed by the addition of the NBF. In either of these cases (and in any of the following cases), the resulting products may be purified by any number of means available to those skilled in the art including, but not limited to, size exclusion chromatography, reversed phase chromatography, silica gel chromatography, ion exchange chromatography, ultrafiltration, and selective precipitation.

In various embodiments, amine bearing components can be coupled to —COOH bearing frameworks (CBFs). CBFs using activated ester moieties (e.g., see Hermanson in *Bioconjugate Techniques, 2nd edition*, Academic Press, 2008 and references cited therein). Briefly, a CBF with terminal activated carboxylic acid esters such as —NHS, —SSC, —NPC, etc. is dissolved in an anhydrous organic solvent such as DMSO or DMF. The desired number of equivalents of amine bearing component are then added and mixed for several hours at room temperature. Amine bearing components can also be conjugated to CBFs to produce a stable amide bond as described by Baudys et al., *Bioconj. Chem.* 9:176-183, 1998. This reaction can be achieved by adding tributylamine (TBA) and isobutylchloroformate to a solution of the CBF and an amine bearing component in dimethylsulfoxide (DMSO) under anhydrous conditions. Amine bearing components can alternatively be coupled to OBFs through cyanalation using reagents including, but not limited to, cyanogen bromide (CNBr), N-cyanotriethylammonium tetrafluoroborate (CTEA), 1-Cyano-4-(Dimethylamino)-pyridinium tetrafluorborate (CDAP), and p-nitrophenylcyanate (pNPC). CNBr reactions can be carried out at mildly basic pH in aqueous solution. CDAP reactions are carried out in a mixture of DMSO and water at mildly basic pH using triethylamine (TEA) as a catalyst. In certain embodiments, amine bearing components can be conjugated to NBFs, e.g., through glutaraldehyde coupling in aqueous buffered solutions containing pyridine followed by quenching with glycine. In certain embodiments, amine bearing components can be conjugated to aldehyde bearing frameworks using a Schiff Base coupling procedure followed by reduction (e.g., see see Hermanson in *Bioconjugate Techniques*, 2$^{nd}$ edition, Academic Press, 2008 and references cited therein as well as Mei et al. in *Pharm. Res.* 16: 1680-1686, 1999 and references cited therein). Briefly, a framework with terminal activated aldehydes (e.g., acetaldehyde, propionaldehyde, butyraldehyde, etc.) is dissolved in an aqueous buffer with the pH at or below neutral to prevent unwanted aldehyde hydrolysis. The desired number of equivalents of an amine bearing component are then added and mixed at room temperature followed by addition of an excess of suitable reducing agent (e.g., sodium borohydride, sodium cyanobrohydride, sodium triacetoxyborohydride pyridine borane, triethylamine borane, etc.).

In various embodiments, hydroxyl bearing components can be conjugated to OBFs according to the divinylsulfone (DVS) procedure. Using this procedure, the OBF is added to a pH 11.4 bicarbonate buffer and activated with DVS followed by addition of a hydroxyl bearing component after which glycine is added to neutralize and quench the reaction. Hydroxyl bearing components may also be coupled to OBFs using activated ester moieties as described above to produce ester bonds.

In various embodiments, sulfhydryl bearing components can be coupled to maleimide bearing frameworks (MBFs) using a relatively mild procedure to produce thioether bonds (e.g., see Hermanson in *Bioconjugate Techniques*, 2$^{nd}$ edition, Academic Press, 2008 and references cited therein). Because the maleimide group is much less susceptible to hydrolysis than activated esters, the reaction can be carried out under aqueous conditions. Briefly, an MBF is dissolved in a buffered aqueous solution at pH 6.5-7.5 followed by the desired number of equivalents of sulfhydryl bearing component. After mixing at room temperature for several hours, the thioether coupled conjugate may be purified. Sulfhydryl bearing components can also be conjugated to NBFs according to a method described by Thoma et al., *J. Am. Chem. Soc.* 121:5919-5929, 1999. This reaction involves suspending the NBF in anhydrous dimethylformamide (DMF) followed by the addition of 2,6-lutidine and acid anhydride and subsequent purification of the reactive intermediate. A sulfhydryl bearing component is then added to a solution of the intermediate in DMF with triethylamine.

In various embodiments, azide bearing components can be coupled to an alkyne bearing framework (ABF) using the copper(I)-catalyzed modern version of the Huisgen-type azide-alkyne cycloaddition to give a 1,4-di-substituted 1,2,3-triazole (e.g., see Dondoni, *Chem. Asian J.* 2:700-708, 2007 and references cited therein as well as Dedola et al., *Org. Biomol. Chem.* 5: 1006-1017, 2007). This reaction, commonly referred to as a "click" reaction, may be carried out for example in neat THF using N,N-diisopropylethylamine and Cu(PPh$_3$)$_3$Br as the catalyst system (e.g., see Wu et al., *Chem. Commun.* 5775-5777, 2005). The reaction may also be carried out in a 3:1 (THF:water) mixture using sodium ascorbate and CuSO$_4$.5H$_2$O as the catalyst system (e.g., see Wu et al., supra). In either case, the azide bearing component is added to the ABF at the desired number of equivalents followed by mixing for 12-48 hours at room temperature. Alternatively, alkyne bearing components may be conjugated to an azide bearing framework using exactly the same conditions described above.

Certain components may naturally possess more than one of the same chemically reactive moiety. In some examples, it is possible to choose the chemical reaction type and conditions to selectively react the component at only one of those sites. For example, in the case where insulin is conjugated through reactive amines, in certain embodiments, the N-terminal α-Phe-B1 is a preferred site of attachment over the N-terminal α-Gly-A1 and ε-Lys-B29 to preserve insulin bioactivity (e.g., see Mei et al., *Pharm. Res.* 16: 1680-1686, 1999 and references cited therein as well as Tsai et al., *J. Pharm. Sci.* 86: 1264-1268, 1997). In an exemplary reaction between insulin with hexadecenal (an aldehyde-terminated molecule), researchers found that mixing the two components overnight in a 1.5M pH 6.8 sodium salicylate aqueous solution containing 54% isopropanol at a ratio of 1:6 (insulin:aldehyde mol/mol) in the presence of sodium cyanoborohydride resulted in over 80% conversion to the single-substituted Phe-B1 secondary amine-conjugated product (Mei et al., *Pharm. Res.* 16:1680-1686, 1999). Their studies showed that the choice of solvent, pH, and insulin:aldehyde ratio all affected the selectivity and yield of the reaction. In most cases, however, achieving selectivity through choice of chemical reaction conditions is difficult. Therefore, in certain embodiments it may be advantageous to selectively protect the component (e.g., insulin) at all sites other than the one desired for reaction followed by a deprotection step after the material has been reacted and purified. For example, there are numerous examples of selective protection of insulin amine groups available in the literature including those that may be deprotected under acidic (BOC), slightly acidic (citraconic anhydride), and basic (MSC) conditions (e.g., see Tsai et al., *J. Pharm. Sci.* 86: 1264-1268, 1997; Dixon et al., *Biochem. J.* 109: 312-314, 1968; and Schuettler et al., *D. Brandenburg Hoppe Seyler's Z. Physiol. Chem.* 360: 1721, 1979). In one example, the Gly-A1 and Lys-B29 amines may be selectively protected with tert-butoxycarbonyl (BOC) groups which are then removed after conjugation by incubation for one hour at 4 C in a 90% trifluoroacetic acid (TFA)/10% anisole solution. In one embodiment, a dry powder of insulin is dissolved in anhydrous DMSO followed by an excess of triethylamine. To this solution, approximately two equivalents of di-tert-butyl dicarbonate solution in THF is added slowly and the solution allowed to mix for 30-60 minutes. After reaction, the crude solution is poured in an excess of acetone followed by drop-wise addition of dilute HCl to precipitate the reacted insulin. The precipitated material is centrifuged, washed with acetone and dried completely under vacuum. The desired di-BOC protected product may be separated from unreacted insulin, undesired di-BOC isomers, and mono-BOC and tri-BOC byproducts using preparative reverse phase HPLC or ion exchange chromatography (e.g., see Tsai et al., *J. Pharm. Sci.* 86: 1264-1268, 1997). In the case of reverse phase HPLC, a solution of the crude product in 70% water/30% acetonitrile containing 0.1% TFA is loaded onto a C8 column and eluted with an increasing acetonitrile gradient. The desired di-BOC peak is collected, rotovapped to remove acetonitrile, and lyophilized to obtain the pure product.

LRP$^B$ and LRP$^D$ (Non-Covalent Conjugation)

One of ordinary skill will appreciate that a variety of conjugation chemistries may be used to non-covalently conjugate an X with a T and/or W with a T (generally "components"). Such techniques are widely known in the art, and exemplary techniques are discussed below. In certain embodiments, the dissociation constant ($K_d$) of the non-covalent linkage in human serum is less than 1 pmol/L. For example, a component may be non-covalently bound to a conjugate framework via a non-covalent ligand-receptor pair as is well known in the art (e.g., without limitation a biotin-avidin based pair). In such an embodiment, one member of the ligand receptor-pair is covalently bound to the component while the other member of the pair is covalently bound to the conjugate framework. When the component and conjugate framework are combined, the strong non-covalent interaction between the ligand and its receptor causes the component to become non-covalently bound to the conjugate framework. Typical ligand/receptor pairs include protein/co-factor and enzyme/substrate pairs. Besides the commonly used biotin/avidin pair, these include without limitation, biotin/streptavidin, digoxigenin/anti-digoxigenin, FK506/FK506-binding protein (FKBP), rapamycin/FKBP, cyclophilin/cyclosporin and glutathione/glutathione transferase pairs. Other suitable ligand/receptor pairs would be recognized by those skilled in the art, e.g., monoclonal antibodies paired with a epitope tag such as, without limitation, glutathione-5-transferase (GST), c-myc, FLAG® and further those described in Kessler pp. 105-152 of *Advances in Mutagenesis*" Ed. by Kessler, Springer-Verlag, 1990; "*Affinity Chromatography: Methods and Protocols (Methods in Molecular Biology)*" Ed. by Pascal Baillon, Humana Press, 2000; and "*Immobilized Affinity Ligand Techniques*" by Hermanson et al., Academic Press, 1992.

k and q

For conjugates of general formula (II), k is an integer from 2 to 11, inclusive, defining at least two k-branches within the conjugate. In certain embodiments, k=2 or 3. q is an integer from 1 to 4, inclusive, and defines the number of D groups which are bound to the central $\boxed{A}$ group. In certain embodiments, q=1. In some embodiments, q=2. k+q is an integer from 3 to 6, inclusive. In certain embodiments, k+q=3 or 4.

For conjugates of general formula (III), when j is 2, 3, or 4, k is an integer from 1 to 11, inclusive. In certain embodiments, k is 1, 2, or 3. q is an integer from 1 to 4, inclusive, and defines the number of D groups which are bound to the central $\boxed{A}$ group. In certain embodiments, q=1. In some embodiments, q=2. k+q is an integer from 3 to 6, inclusive. In certain embodiments, k+q=3 or 4.

p and m

Each occurrence of p is independently an integer from 1 to 5, inclusive. In certain embodiments, each occurrence of p is the same. In certain embodiments, p=1, 2 or 3. In certain embodiments, p=1.

Each occurrence of m is independently an integer from 1 to 5, inclusive. In certain embodiments, each occurrence of m is the same. In certain embodiments, m=1, 2 or 3. In certain embodiments, m=1.

n and v

Each occurrence of n is independently an integer from 0 to 5, inclusive, with the proviso that within each k-branch at least one occurrence of n is ≥1. Branches within a given k-branch are referred to herein as n-branches.

In certain embodiments, each occurrence of $\boxed{A}$ in a p-bracketed moiety is substituted by a number of n-bracketed moieties corresponding to a value of n≥1, e.g., see formula (IIa) above. In some such embodiments, each occurrence of n in the conjugate is the same. In some of these embodiments, n=1 or 2.

In other embodiments, only terminal occurrences of $\boxed{A}$ in a p-bracketed moiety are substituted by a number of n-bracketed moieties corresponding to a value of n≥1, e.g., see formula (IIb) above. In certain embodiments, each k-branch includes just one occurrence of n≥1 (i.e., all other occurrences of n=0). In some such embodiments, each occurrence of n in the conjugate is the same. In some of these embodiments, n=1 or 2.

Each occurrence of v is independently an integer from 0 to 5, inclusive, with the proviso that within each k-branch at least one occurrence of v is ≥1.

In certain embodiments, each occurrence of $\boxed{A}$ in an m-bracketed moiety is substituted by a number of B moieties corresponding to the value of v≥1, e.g., see formula (IIc) above. In some such embodiments, each occurrence of v in the conjugate is the same. In some of these embodiments, v=1 or 2.

In other embodiments, only terminal occurrences of $\boxed{A}$ in an m-bracketed moiety are substituted by a number of B moieties corresponding to a value of v≥1, e.g., see formula (IId) above. In certain embodiments, each k-branch includes just one occurrence of v≥1 (i.e., all other occurrences of v=0). In some such embodiments, each occurrence of v in the conjugate is the same. In some of these embodiments, v=1 or 2. In certain embodiments, each n-branch includes at least one occurrence of v≥1. In certain embodiment, each n-branch includes just one occurrence of v≥1 (i.e., all other occurrences of v=0). In some such embodiments, each occurrence of v in the conjugate is the same. In some of these embodiments, v=1 or 2.

j j of formula (III) is an integer from 1 to 4, inclusive, and defines the number of conjugations to the D group. In certain embodiments, j=1. In certain embodiments, j=2. In some embodiments, j=3. In other embodiments, j=4.

Loading Levels

In general, the amount of drug (or detectable label) that is loaded onto a conjugate will depend on the molecular weight of the drug (or detectable label) and can be controlled by adjusting the molecular weight of the conjugate framework and/or the level of chemical activation (i.e., when pendant groups are added to the framework). In various embodiments, the drug and/or detectable label loading level may be in the range of 5 to 99% w/w of drug and/or detectable label to conjugate (e.g., including drug). In various embodiments, loading levels within the narrower range of 50 to 99% may be used, e.g., in the range of 80 to 99%.

Other

In various embodiments, a biodegradable framework may be used. In various embodiments, a non-biodegradable framework may be used, e.g., when biodegradability is not relevant to the application and/or when the resulting framework or conjugate is sufficiently well excreted that biodegradability is not necessary. In various embodiments, the conjugate framework (or spacer when present, e.g., between a drug and framework) is susceptible to digestion by an enzyme. In various embodiments, the enzyme is present at the site of administration. One skilled in the art will recognize that a number of enzymes are present in patients that could cleave a conjugate framework. Without limitation, these include saccharidases, peptidases, and nucleases. Exemplary saccharidases include, but are not limited to, maltase, sucrase, amylase, glucosidase, glucoamylase, and dextranase. Exemplary peptidases include, but are not limited to, dipeptidyl peptidase-IV, prolyl endopeptidase, prolidase, leucine aminopeptidase, and glicyl glycine dipeptidase. Exemplary nucleases include, but are not limited to, deoxyribonuclease I, ribonuclease A, ribonucelase T1, and nuclease S1.

One skilled in the art will also recognize that, depending on the choice of enzyme, there are a number of conjugate frameworks that are susceptible to enzymatic cleavage. For example, in cases where saccharidase degradation is desired, frameworks which include polysaccharides can be used (e.g., without limitation, a conjugate that includes a polysaccharide comprising repeating chains of 1,4-linked alpha-D-glucose residues will be degraded by alpha-amylases). Without limitation, suitable polysaccharides include glycogen and partially digested glycogen derived from any number of sources, including but not limited to, sweet corn, oyster, liver (human, bovine, rabbit, rat, horse), muscle (rabbit leg, rabbit abdominal, fish, rat), rabbit hair, slipper limpet, baker's yeast, and fungus. Other polysaccharide polymers and spacers that one could use include carboxylated polysaccharides, —$NH_2$ pendant polysaccharides, hydroxylated polysaccharides, alginate, collagen-glycosaminoglycan, collagen, mannan, amylose, amylopectin, cellulose, hyaluronate, chondroitin, dextrin, chitosan, etc. In cases where peptidase cleavage is desired, polypeptides that contain amino acid sequences recognized by the cleaving enzyme can be used (e.g., without limitation, a conjugate that includes a [-Glycine-Proline-] sequence will be degraded by prolidase). In certain embodiments one could use co-polymers of aminated and non-aminated amino acids, co-polymers of hydroxylated and non-hydroxylated amino acids, co-polymers of carboxylated and non-carboxylated amino acids, co-polymers of the above or adducts of the above. In cases where nuclease degradation is desired, polynucleotides can be used (e.g., without limitation, a conjugate that includes a polynucleotide containing an oligomer of sequential adenosine residues will be degraded by ribonuclease A).

In various embodiments, the pharmacokinetic and/or pharmacodynamic behavior of a conjugate (i.e., conjugated drug and/or drug which has been released from a conjugate by chemical or enzymatic degradation) may be substantially the same as the corresponding unconjugated drug (e.g., when both are administered subcutaneously). For example, from a pharmacokinetic (PK) perspective, the serum concentration curve may be substantially the same as when an equivalent amount of unconjugated drug is administered. Additionally or alternatively, the serum $T_{max}$, serum $C_{max}$, mean serum residence time (MRT), mean serum absorption time (MAT) and/or serum half-life may be substantially the same as when the unconjugated drug is administered. From a pharmacodynamic (PD) perspective, the conjugate may act on substances within the body in substantially the same way as the unconjugated drug. For example, in the case of an insulin conjugate, the conjugate may affect blood glucose levels in substantially the same way as unconjugated insulin. In this case, substantially similar pharmacodynamic behavior can be observed by comparing the time to reach minimum blood glucose concentration ($T_{nadir}$), the duration over which the blood glucose level remains below a certain percentage of the initial value (e.g., 70% of initial value or $T_{70\% BGL}$), etc. It will be appreciated that these PK and PD characteristics can be determined according to any of a variety of published pharmacokinetic and pharmacodynamic methods (e.g., see Baudys et al., *Bioconjugate Chem.* 9:176-183, 1998 for methods suitable for subcutaneous delivery).

In one embodiment, a conjugate (i.e., in isolated form without aptamers) produces pharmacokinetic (PK) parameters such as time to reach maximum serum drug concentration ($T_{max}$), mean drug residence time (MRT), serum half-life, and mean drug absorption time (MAT) that are within 40% of those values determined for the unconjugated drug. In various embodiments, a conjugate produces PK parameters that are within 35%, 30%, 25%, 20%, 15% or even 10% of those produced by the unconjugated drug. In some embodiments, a conjugate produces PK parameters that are within 20% of those produce by the unconjugated drug. For example, in embodiments involving an insulin conjugate for subcutaneous delivery the conjugate may produce an insulin $T_{max}$ between 15-30 minutes, a mean insulin residence time (MRT) of less than 50 minutes, or a mean insulin absorption time (MAT) of less than 40 minutes, all of which are within 20% of those values determined from the human recombinant insulin treatment group. In certain embodiments, the conjugate may produce an insulin $T_{max}$ between 20-25 minutes, a mean insulin residence time (MRT) of less than 45 minutes, and a mean insulin absorption time (MAT) of less than 35 minutes. In certain embodiment, the conjugate may produce a serum half-life of less than 120 minutes, e.g., less than 100 minutes.

In one embodiment, an inventive conjugate produces pharmacodynamic (PD) parameters such as time to reach minimum/maximum blood concentration of a substance ($T_{nadir}$/$T_{max}$) or duration over which the blood level of the substance remains below/above 70%/130% of the initial value ($T_{70\% BL}$/$T_{130\% AL}$). For example, in embodiments involving an insulin conjugate for subcutaneous delivery the conjugate may produce a glucose $T_{nadir}$ between 45-60 minutes and a glucose $T_{70\% BGL}$ of less than 180 minutes, both of which are within 20% of those determined from the human recombinant insulin treatment group. In certain embodiments the conjugate may produce a glucose $T_{nadir}$ between 50-55 minutes and a glucose $T_{70\% BGL}$ of less than 160 minutes. In various embodiments, a conjugate produces PD parameters that are within 40%, 35%, 30%, 25%, 20%, 15% or even 10% of those produced by the unconjugated drug. In some embodiments, a conjugate produces PD parameters that are within 20% of those produce by the unconjugated drug.

Intermediates for Preparing Conjugates

In one aspect, the invention provides reagents for preparing conjugates of the present disclosure. Thus, in various embodiments, a compound of general formula (II) is provided wherein:

each of [A], T, D, k, q, k+q, p, n, m and v is defined as described above and herein;
  B is -T-$L^{B'}$; and
  each occurrence of $L^{B'}$ is independently hydrogen, an alkyne-containing moiety, an azide-containing moiety, or an optionally substituted carbonyl-reactive, thiol-reactive, amine-reactive, or hydroxyl-reactive moiety.

In other embodiments, a compound of general formula (II) is provided wherein:

each of [A], T, B, k, q, k+q, p, n, m and v is defined as described above and herein;
  D is -T-$L^{D'}$; and
  each occurrence of $L^{D'}$ is independently hydrogen, an alkyne-containing moiety, an azide-containing moiety, or an optionally substituted carbonyl-reactive, thiol-reactive, amine-reactive, or hydroxyl-reactive moiety.

Methods for Preparing Conjugates

We have exemplified methods for preparing the aforementioned conjugates using insulin as an exemplary drug and aminoethylglucose (AEG), aminoethylmannose (AEM), aminoethylbimannose (AEBM), and/or amino ethyltrimannose (AETM) as exemplary affinity ligands. Without limitation, conjugates with two affinity ligands and one drug molecule and with short distances between all framework components may be prepared using tris(hydroxymethyl)aminomethane (Tris), Tris-succinimidyl aminotriacetate (TSAT), tris-Succinimidyl-1,3,5-benzenetricarboxylate (TSB), and Benzene-1,3,5-tricarboxy-($N^4$-butyric-NHS-ester)amide (TSB-C4) as conjugate frameworks. If more space between framework components is desired then Succinimidyl (6-aminocaproyl)aminotriacetate (TSAT-C6), Succinimidyl (6-amino(PEO-6))aminotriacetate (TSAT-PEO-6), Benzene-1,3,5-tricarboxy-(N-6-aminocaproic-NHS ester)amide (TSB-C6), and Benzene-1,3,5-tricarboxy-(N-10-aminodecanoic-NHS ester)amide (TSB-C10) may be used. The TSAT-C6 spacer arm chemistry imparts more hydrophobic character to the conjugate as compared to TSAT-PEO-6.

For example, for purposes of illustration, in one embodiment, both the affinity ligand (e.g., AEG, AEM, AEMB and AETM) and insulin may be reacted to a TSAT-C6 framework through the terminal activated esters to produce insulin-TSAT-C6-AEG-2, insulin-TSAT-C6-AEM-2, insulin-TSAT-C6-AEMB-2, and insulin-TSAT-C6-AETM-2 conjugates. The various affinity ligands are synthesized ahead of time as discussed in the Examples. In addition, the A1 and B29 amino groups of insulin are BOC-protected as described in the Examples so that each insulin can only react at the Phe-B1 α-amino group. Approximately one equivalent of BOC-insulin as a 40-50 mg/ml solution in DMSO is added at room temperature to a 50 mg/ml solution of TSAT-C6 in DMSO containing excess triethylamine and allowed to react for approximately one hour. Next, an excess of AEG, AEM, AEMB, and/or AETM (2-10 equivalents) as a 100 mg/ml solution in DMSO is added and allowed to react for an additional 2 hours. After reaction, the DMSO solution is superdiluted by 10× into a pH 5 saline buffer after which the pH is adjusted to 8.0 and the solution passed through a Biogel P2 column to remove low molecular reactants and salts. The material eluting in the void fraction is concentrated using a 3K ultrafiltration apparatus after which it is injected on a prep scale reverse phase HPLC column (C8, acetonitrile/water mobile phase containing 0.1% TFA) to purify the desired product from unreacted BOC2-insulin. The desired elution peak is collected pooled and rotovapped to remove acetonitrile followed by lyophilization to obtain a dry powder. Finally, the BOC protecting groups are removed by dissolving the lyophilized powder in 90% TFA/10% anisole for one hour at 4 C followed by 10× superdilution in HEPES pH 8.2 buffer containing 0.150M NaCl. The pH is adjusted to between 7.0 and 8.0 using NaOH solution after which the material is passed through a Biogel P2 column to remove anisole, BOC, and any other contaminating salts. The deprotected, purified aqueous conjugate solution is then concentrated to the desired level and stored at 4 C until needed.

It will be appreciated that this exemplary procedure may be used to produce other conjugates with different affinity ligands and drugs, different conjugation chemistries, different separations between framework components, and/or different valencies by substituting the TSAT-C6 framework with a different framework as described below.

For example, if yet more distance is required between framework components and/or a preserved charge is required at the site of conjugation, then an appropriately-sized amine-bearing diethyl acetal (e.g., aminopropionaldehyde diethyl acetal (APDA) or aminobutyraldehyde diethyl acetal (ABDA)) may be conjugated to one of the reactive groups on the frameworks listed here followed by complete reaction of the remaining reactive groups with the affinity ligand of interest (e.g. AEM, AEBM, or AETM). A reactive aldehyde group can then be revealed from the diethyl acetal under acidic conditions followed by a reductive amination with insulin to complete the drug conjugation step then ABDA-TSAT, ABDA-LCTSAT, etc. may be employed.

In yet another example, tetrakis-(N-succinimidyl carboxypropyl)pentaerythritol (TSPE), may be used to attach three affinity ligands and one drug molecule for increased multivalency. It will also be appreciated by those skilled in the art that any of the above teachings may be used to produce hyperbranched (e.g., dendrimer-like) conjugates with even higher order valencies. For example, Rockendorf and Lindhorst provide a comprehensive review of current approaches for producing hyperbranched structures in *Topics in Current Chemistry.* 217: 202-238, 2001.

Furthermore, ligands already containing a predetermined degree of multivalency may again be reacted according to the procedures described above to produce even higher orders of ligand multiplicity. For example, a divalent AEM-2, AEBM-2, or AETM-2 molecule containing a terminal reactive amine may be prepared by conjugating two of each affinity ligand to a suitable framework to which a reactive amine is also conjugated. A trivalent AEM-3, AEBM-3, or AETM-3 molecule containing a terminal reactive amine may be prepared by conjugating three of each affinity ligand to a suitable framework to which a reactive amine is also conjugated. The $NH_2$-divalent sugars may be reacted with the same frameworks described above to produce drug conjugates with 4 and 6 ligands per drug molecule. The $NH_2$-trivalent sugars may be reacted with the same frameworks described above to produce drug conjugates with 6 and 9 ligands per drug molecule.

In all cases, it should be recognized that a mixture of different ligands may be conjugated to the same drug via a multivalent framework by adjusting the framework chemistry, valency, and the ligand: framework stoichiometry. For example, Insulin-AEM-1-AEBM-1, Insulin-AEBM-1-AETM-1, Insulin AEM-2-AETM-2, and Insulin AEM-1-AETM-2 may all be synthesized according to this mixed ligand method.

Finally, in some cases, it may be desirable to conjugate the affinity ligand to the framework through a different means than the drug. For example, a divalent maleimide/monovalent activate ester functionalized framework (e.g., succinimidyl-3,5-dimaleimidophenyl benzoate (SDMB)) may be used to conjugate two sulfhydryl functionalized affinity ligands and one amine-functionalized drug in separate steps. For example, insulin or another amine-containing drug may be conjugated to the activated ester portion of the framework using methods described herein. In a separate step, the aminoethylsugar (AEM, AEBM, AETM) may be converted to a terminal sulfhydryl-bearing ligand by reaction with 4-iminothiolane. Finally, the framework-di-maleimide-insulin conjugate may be mixed with an excess of sulfhydryl-functionalized sugar to produce the resulting divalent-sugar-insulin conjugate.

Cross-Linked Materials

When aptamers and conjugates are combined in the absence of the target molecule, a non-covalently cross-linked material is formed. In various embodiments, the material may be prepared in aqueous solution through self-assembly by mixing solutions of the aptamer and conjugate. In various embodiments, particles of the material may be prepared by reverse emulsion. As described in more detail in U.S. Patent Application Publication No. 2004-0202719, this can be achieved by adding the aforementioned aqueous solution to a mixture of a hydrophobic liquid and a surfactant and agitating the mixture.

Once formed, the cross-linked material can be used for a variety of applications. When the material is placed in the presence of free target molecules these compete for the interactions between the aptamers and the conjugates. Above a certain concentration of free target molecule, the level of competition becomes such that the material begins to degrade by releasing conjugates from the surface. In various embodiments, the extent and/or rate of release increases as the concentration of target molecule increases. As a result, conjugates are released from the material in a manner which is directly tied to the local concentration of the target molecule.

In general, the release properties of the material will depend on the nature of the aptamers, conjugates, target molecule and conditions (e.g., pH, temperature, etc.). If the affinity of the aptamers for the conjugates is much greater than for the target molecule then the material will only release conjugates at high concentrations of target molecule. As the relative affinity of the aptamers for the conjugates is decreased, release of conjugates from the material will occur at lower target molecule concentrations. The release properties of the material can also be adjusted by varying the relative amounts of aptamer to conjugate. Higher ratios of aptamer to conjugate will lead to materials that release conjugates at higher target molecule concentrations. Lower ratios of aptamer to conjugate will lead to materials that release conjugates at lower target molecule concentrations. It will be appreciated that, depending on the application, these variables will enable one to produce materials which respond to a wide variety of target molecule concentrations.

In various embodiments, the cross-linked material is insoluble when placed in pH 7 HEPES buffered saline at 37 C (25 mM HEPES containing 150 mM NaCl). In various embodiments, the cross-linked material remains substantially insoluble when target molecule is added to the buffer up to a threshold concentration called the set point. Above the set point, the cross-linked material exhibits an increase in the extent and rate of release of conjugates. It will be appreciated that this transition may occur sharply or may occur gradually over a range of concentrations around the set point. In general, the desired set point and transition will depend on the nature of the target molecule and the intended application for the material. In particular, when the material is designed to respond to an increase in the level of a particular target molecule, the desired set point may be determined based on the normal physiological range of concentrations of the target molecule. It is to be understood that the amount of target molecule present in a patient may fluctuate based on internal and/or external factors. For example, in certain embodiments, the amount of target molecule may fluctuate naturally over time, e.g., in response to changes in hormonal cycles or metabolic pathways (lactate increasing during an endurance event, etc.). In certain embodiments, the fluctuations may result from an external event, e.g., an increase in glucose following a meal. In various embodiments, external factors may be used to artificially trigger the release of conjugates from a material of the present disclosure. For example, if release of conjugate is sensitive to an increase in glucose one could artificially release conjugates for a short period of time by ingesting a high-glucose drink.

In various embodiments, the target molecule is glucose. The normal physiological range of glucose concentrations in humans is 60 to 200 mg/dL. Glucose concentrations below 60 mg/dL are considered hypoglycemic. Glucose concentrations above 200 mg/dL are considered hyperglycemic. In various embodiments, a material of the present disclosure may remain substantially insoluble when placed in pH 7 HEPES buffered saline containing 20, 30, 40, 50, 60, 70, 80, 90, or 100 mg/dL glucose at 37 C for six hours using USP dissolution test method II at 50 rpm. In various embodiments, less than 1, 2, 4, 6, 8, or 10% of the material dissolves when placed in pH 7 HEPES buffered saline with 20, 30, 40, 50, 60, 70, 80, 90, or 100 mg/dL glucose at 37 C for six hours using USP dissolution test method II at 50 rpm. In various embodiments, at least 10, 20, 30, 40, 50, 60, 70, 80, 90 or 100% of a material of the present disclosure dissolves when it is placed in pH 7 HEPES buffered saline with 100, 150, 200, 250, 300, 350 or 400 mg/dL glucose at 37 C for six hours using USP dissolution test method II at 50 rpm.

The following tables provide normal physiological ranges for other exemplary target molecules:

|  | Low | High | Unit |
|---|---|---|---|
| Metabolites |  |  |  |
| Urea | 7 | 18 | mg/dL |
| Creatinine - male | 0.7 | 1.3 | mg/dL |
| Creatinine - female | 0.6 | 1.1 | mg/dL |
| Hormones |  |  |  |
| Thyroid stimulating hormone (TSH) | 0.4 | 4.7 | mIU/L |
| Free thyroxine (FT4) | 9 | 24 | pmol/L |
| Free triiodothyronine (FT3) | 2.5 | 5.3 | pmol/L |
| Adrenocorticotropic hormone (ACTH) | 1.3 | 15 | pmol/L |
| Cortisol (morning) | 250 | 850 | nmol/L |
| Cortisol (afternoon) | 110 | 390 | nmol/L |
| Prolactin (male) | n/a | 450 | mIU/L |
| Prolactin (female) | n/a | 580 | mIU/L |
| Testosterone (male post-puberty) | 8 | 38 | nmol/L |
| Testosterone (male pre-puberty) | 0.1 | 0.5 | nmol/L |
| Testosterone (female) | 0.3 | 2.5 | nmol/L |

It will be appreciated that the desired set point for these and other target molecules can be readily determined for a variety of different applications. It will also be appreciated that the set point may need to be adjusted for certain patients (e.g., based on patient gender, patients with abnormally low or high levels of a target molecule, etc.) or applications (e.g., a drug delivery system designed to release on a more frequent basis may require a lower threshold concentration than a system designed to release less frequently).

It will be appreciated that a material having a desired set point may be generated via routine experimentation using the materials and methods described herein. For example, the same aptamer and conjugate can be combined to produce a series of materials with a gradually increasing ratio of aptamer to conjugate (w/w). These materials will cover a spectrum of set points. Once a lead material with a suitable set point has been identified the process can be repeated with a finer resolution to yield an optimized material. Alternatively (or additionally) the same conjugate can be combined with a plurality of different aptamers that have gradually increasing affinities for the conjugate. This will yield a plurality of materials with a spectrum of set points that can be further refined (e.g., by varying the w/w ratio of aptamer to conjugate). Alternatively one could initiate the process by combining the same aptamer with a plurality of different conjugates. In various embodiments, the conjugates may have varying affinities for the aptamer (e.g., as a result of including different affinity ligands). In various embodiments, the conjugates may include the same affinity ligands but have different molecular weights (e.g., as a result of different conjugate frameworks).

Uses

In another aspect, the present disclosure provides methods of using the materials. In general, the materials can be used to controllably release conjugates in response to a target molecule. As discussed below, the material can be brought into contact with the target molecule in vitro or in vivo.

In various embodiments, a material may be used as a component of an in vitro or in vivo chemical sensor. This aspect is described below in the context of glucose sensors; however, it will be appreciated from the foregoing that other chemical sensors may be prepared by simply using a different target molecule.

For example, in various embodiments, a material of the present disclosure may be used in glucose sensors that are based on fluorescence resonance energy transfer (FRET). FRET is based on the fact that when two different fluorophores are brought closely together this allows for energy transfer between the two fluorophores, resulting in a decrease in the fluorescence of one or both of the fluorophores, which is called fluorescence quenching (Ballerstadt et al., *Anal. Can. Acta* 345:203-212, 1997). For example, in certain embodiments, in the absence of glucose, a mixture of a fluorescently labeled aptamer and a fluorescently labeled conjugate will form an insoluble cross-linked material and the neighboring fluorophores will undergo FRET. In the presence of glucose, the average distance between the fluorescently labeled aptamer and the fluorescently labeled conjugate will increase causing the level of FRET to decrease and thereby leading to an increase in the individual fluorescence signals. The level of fluorescence can thereby be directly correlated with the level of glucose. It is to be understood that alternative pairs of labels that produce a measurable response when brought in close proximity may be used instead of a pair of fluorescent labels. Thus, in certain embodiments, the invention provides a method comprising steps of: (I) mixing: (a) multivalent polynucleotide aptamers with at least two binding sites for glucose, wherein the polynucleotide aptamers include a first label which generates a measurable response when in close proximity to a second label; (b) conjugates that comprise an affinity ligand and the second label; (II) exposing a sample to the mixture of multivalent polynucleotide aptamers and conjugates, wherein: (a) if glucose is absent from the sample, the conjugates form a cross-linked material with the polynucleotide aptamers through affinity binding to the polynucleotide aptamers to produce a measurable response; (b) if glucose is present in the sample, the response is reduced because formation of cross-linked material is inhibited as a result of glucose from the sample competing with the conjugates for the binding sites on the polynucleotide aptamers; and (III) detecting and optionally measuring the response with a sensor to determine the presence and optionally the amount of glucose in the sample. In certain embodiments, the first and second labels are fluorescent labels and the response is a fluorescent signal.

In certain embodiments, the two labels (e.g., fluorescent labels) may be located on different molecules that are brought into proximity by binding to the same polynucleotide aptamer. Thus, in certain embodiments, the invention provides a method comprising steps of: (I) mixing: (a) multivalent polynucleotide aptamers with at least two binding sites for glucose; (b) a first group of molecules that comprise an affinity ligand and a first label which generates a measurable response when in close proximity to a second label; and (c) a second group of molecules that comprise an affinity ligand and the second label; (II) exposing a sample to the mixture of multivalent polynucleotide aptamers, and the first and second groups of molecules, wherein: (a) if glucose is absent from the sample, members of the first and second group of molecules are brought in close proximity through affinity binding to the multivalent polynucleotide aptamers to produce a binding complex and a measurable response; (b) if glucose is present in the sample, the response is reduced because fewer of said binding complexes form as a result of glucose from the sample competing with the first and second molecules for the binding sites on the multivalent polynucleotide aptamers; and (III) detecting and optionally measuring the response with a sensor to determine the presence and optionally the amount of glucose in the sample. In certain embodiments, the first and second labels are fluorescent labels and the response is a fluorescent signal.

In other exemplary embodiments, materials of the present disclosure may be used in viscosity-based glucose sensors (e.g., see U.S. Pat. Nos. 6,267,002; 6,477,891; and 6,938,463). Conjugates and aptamers are again combined to form a cross-linked material. Addition of glucose to the material now causes a concentration dependent reduction in viscosity which can be measured (e.g., as a function of shear rate using a microviscometer set up in a cone-and-plate geometry). The viscosity of the sample can thereby be directly correlated with the level of glucose. It will be appreciated that these two exemplary glucose sensors do not require any drug to be present within the conjugates. It will also be appreciated that a viscosity-based sensor does not require a detectable label to be present within the conjugates.

In certain embodiments, the invention provides a method comprising steps of: (I) providing: (a) conjugates that comprises a plurality of affinity ligands, (b) multivalent polynucleotide aptamers with at least two binding sites for glucose; (II) mixing the conjugates and polynucleotide aptamers, wherein the viscosity of the resulting mixture is due to the binding between the conjugates and polynucleotide aptamers; (III) contacting the mixture with a sample containing glucose which displaces conjugates from the polynucleotide aptamers and causes a concentration dependent reduction in viscosity; and (IV) detecting and optionally measuring the resulting change in viscosity to determine the presence and optionally the amount of glucose in the sample.

In various embodiments, a material may be used to controllably deliver a drug to a patient. The invention encompasses treating a disease or condition by administering a material of the present disclosure. Although the materials can be used to treat any patient (e.g., dogs, cats, cows, horses, sheep, pigs, mice, etc.), they are most preferably used in the treatment of humans. A material can be administered to a patient by any route. In general the most appropriate route of administration will depend upon a variety of factors including the nature of the disease or condition being treated, the nature of the drug, the nature of the target molecule, the condition of the patient, etc. In general, the present disclosure encompasses administration by oral, intravenous, intramuscular, intra-arterial, subcutaneous, intraventricular, transdermal, rectal, intravaginal, intraperitoneal, topical (as by powders, ointments, or drops), buccal, or as an oral or nasal spray or aerosol. General considerations in the formulation and manufacture of pharmaceutical compositions for these different routes may be found, for example, in *Remington's Pharmaceutical Sciences*, 19$^{th}$ ed., Mack Publishing Co., Easton, Pa., 1995.

In various embodiments, the material may be administered subcutaneously, e.g., by injection. The material can be dissolved in a carrier for ease of delivery. For example, the carrier can be an aqueous solution including, but not limited to, sterile water, saline or buffered saline. In general, a therapeutically effective amount of a drug in the form of a conjugate will be administered. By a "therapeutically effective amount" of a drug is meant a sufficient amount of the drug to treat (e.g., to ameliorate the symptoms of, delay progression of, prevent recurrence of, delay onset of, etc.) the disease or condition at a reasonable benefit/risk ratio, which involves a balancing of the efficacy and toxicity of the drug. In general, therapeutic efficacy and toxicity may be determined by standard pharmacological procedures in cell cultures or with experimental animals, e.g., by calculating the $ED_{50}$ (the dose that is therapeutically effective in 50% of the treated subjects)

and the $LD_{50}$ (the dose that is lethal to 50% of treated subjects). The $ED_{50}/LD_{50}$ represents the therapeutic index of the drug. Although in general drugs having a large therapeutic index are preferred, as is well known in the art, a smaller therapeutic index may be acceptable in the case of a serious disease or condition, particularly in the absence of alternative therapeutic options. Ultimate selection of an appropriate range of doses for administration to humans is determined in the course of clinical trials.

In various embodiments, the drug is insulin and the average daily dose of insulin is in the range of 10 to 200 U, e.g., 25 to 100 U (where 1 Unit of insulin is ~0.04 mg). In certain embodiments, an amount of material with these insulin doses is administered on a daily basis. In certain embodiments, an amount of material with 5 to 10 times these insulin doses is administered on a weekly basis. In certain embodiments, an amount of material with 10 to 20 times these insulin doses is administered on a bi-weekly basis. In certain embodiments, an amount of material with 20 to 40 times these insulin doses is administered on a monthly basis. Those skilled in the art will be recognize that this same approach may be extrapolated to other approved drugs with known dose ranges, e.g., any of the approved insulin sensitizers and insulin secretagogues described herein.

It will be understood that the total daily usage of a drug for any given patient will be decided by the attending physician within the scope of sound medical judgment. The specific therapeutically effective amount for any particular patient will depend upon a variety of factors including the disease or condition being treated; the activity of the specific drug employed; the specific composition employed; the age, body weight, general health, sex and diet of the patient; the time of administration, route of administration and rate of excretion of the specific drug employed; the duration of the treatment; drugs used in combination or coincidental with the specific drug employed; and like factors well known in the medical arts. In various embodiments, a material of the present disclosure may be administered on more than one occasion. For example, the present disclosure specifically encompasses methods in which a material is administered by subcutaneous injection to a patient on a continuous schedule (e.g., once a day, once every two days, once a week, once every two weeks, once a month, etc.).

In certain embodiments, a material of the present disclosure may be used to treat hyperglycemia in a patient (e.g., a mammalian patient). In certain embodiments, the patient is diabetic. However, the present methods are not limited to treating diabetic patients. For example, in certain embodiments, a material may be used to treat hyperglycemia in a patient with an infection associated with impaired glycemic control. In certain embodiments, a material may be used to treat diabetes.

In various embodiments, a material of the present disclosure may be administered to a patient who is receiving at least one additional therapy. In various embodiments, the at least one additional therapy is intended to treat the same disease or disorder as the administered material. In various embodiments, the at least one additional therapy is intended to treat a side-effect of the primary drug. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a single material of the present disclosure may include more than one drug for treating the same disease or disorder. In certain embodiments, two or more separate materials of the present disclosure may be administered (as a mixture or separately) that include different drugs for treating the same disease or disorder. In certain embodiments, an unconjugated secondary drug may be included in a material of the present disclosure (i.e., a drug which is simply mixed with the components of the material and not covalently bound to the cross-linked material). For example, in certain embodiments, any of these approaches may be used to administer more than one anti-diabetic drug to a subject. Certain exemplary embodiments of this inventive approach are described in more detail below in the context of insulin-related therapies; however, it will be appreciated from the foregoing that other therapies will benefit from such combination approaches.

Insulin sensitizers (e.g., biguanides such as metformin, glitazones) act by increasing a patient's response to a given amount of insulin. A patient receiving an insulin sensitizer will therefore require a lower dose of an insulin-based material of the present disclosure than an otherwise identical patient would. Thus, in certain embodiments, a material comprising insulin conjugates may be administered to a patient who is also being treated with an insulin sensitizer. In various embodiments, the material of the present disclosure may be administered at up to 75% of the normal dose required in the absence of the insulin sensitizer. In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the materials of the present disclosure are only effective for this subclass of patients when they release high levels of insulin-conjugates in a suitable timeframe. In certain embodiments, the treatment of this subclass of patients may be facilitated by combining the two approaches. Thus in certain embodiments, a traditional insulin-based therapy is used to provide a baseline level of insulin and a material of the present invention is administered to provide a controlled supplement of insulin when needed by the patient. Thus, in certain embodiments, a material comprising insulin conjugates may be administered to a patient who is also being treated with insulin. In various embodiments, the insulin may be administered at up to 75% of the normal dose required in the absence of the material of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

Kits

In another aspect the present disclosure provides kits that include aptamers and conjugates and other reagents for preparing a material. For example, a kit may include separate containers that include a plurality of conjugates and a plurality of aptamers. When the conjugates and aptamers of the kit are mixed a cross-linked material is formed. In various embodiments, the material is designed for subcutaneous delivery and the kit includes a syringe. In various embodiments, a kit may include a syringe which is pre-filled with a cross-linked material. The kit may also include instructions for mixing the conjugates and aptamers to produce the cross-linked material.

In yet another aspect, the present disclosure provides libraries of conjugates and/or aptamers. These libraries may be particularly useful for generating materials with a desired set point. In various embodiments, a library may include a plurality of aptamers which produce different set points with the same conjugate. In various embodiments, a library may further include one or more conjugates which form cross-linked materials with aptamers in the library. When the library includes more than one such conjugate, the different conjugates may have different molecular weights, a different number of affinity ligands per conjugate molecule and/or different affinity ligands. In various embodiments, a library may include one or more of the conjugates that include more than one type of affinity ligand. In various embodiments, a library may include a plurality of conjugates which produce different set points with the same aptamer. In various embodiments, a library may further include one or more aptamers which form cross-linked materials with conjugates in the library.

In yet another aspect, the present disclosure provides a kit that comprises: (a) a first container that includes aptamers that include a first label which generates a measurable response when in close proximity to a second label; and (b) a second container that includes conjugates that comprise the second label.

In yet another aspect, the present disclosure provides a kit that comprises: (a) a first container that includes aptamers; (b) a second container that includes a first group of molecules that comprise an affinity ligand and a first label which generates a measurable response when in close proximity to a second label; and (c) a third container that includes a second group of molecules that comprise an affinity ligand and the second label. In certain embodiments, the first and second molecules are in the same container.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

EXAMPLES

Example 1

Monomeric Glucose-Binding Aptamers

Nuclease-resistant RNA sequences were identified that bind to immobilized glycogen at glucose concentrations <50 mg/dL and elute over a wide range of increasing glucose concentrations. An initial library of $10^{15}$-$10^{16}$ sequences was constructed according to established methods, for a DNA oligonucleotide with a sequence comprised of a T7 promoter region followed by a 20 base pair (bp) 5' primer, a 40 bp random region, and a 20 bp 3' primer site. T7 RNA polymerase was used with 2'-fluoro-2'-deoxypyrimidine 5'-triphosphates (2'-F-CTP and 2'F-UTP) in order to transcribe the modified RNA aptamers, which were used in a SELEX process with a cyanogen-bromide crosslinked oyster glycogen (MW=500,000 g/mol, Sigma Aldrich) as the binding stationary phase.

After six rounds of selection one viable monoclonal sequence (30106K$_1$) was found that had any glycogen bead binding affinity. 30106K1 was reverse-transcribed and mutated according to an existing methodology (see below), and the new pool was reselected using glycogen bead binding and glucose elution selection methodology in an attempt to obtain a sequence homologous family of aptamers in order to discover the minimal sequence motif necessary for reversible binding to the glycogen stationary phase.

After mutagenesis, two more rounds of selection were performed, and the resulting mixture was tested to obtain monoclonals, which were then sequenced to obtained 28 monoclonals, 7 of which were unique. Several of the sequences had a great deal of homology, while sequences 1, 4 and 6 differed substantially from the others.

Figure 1:
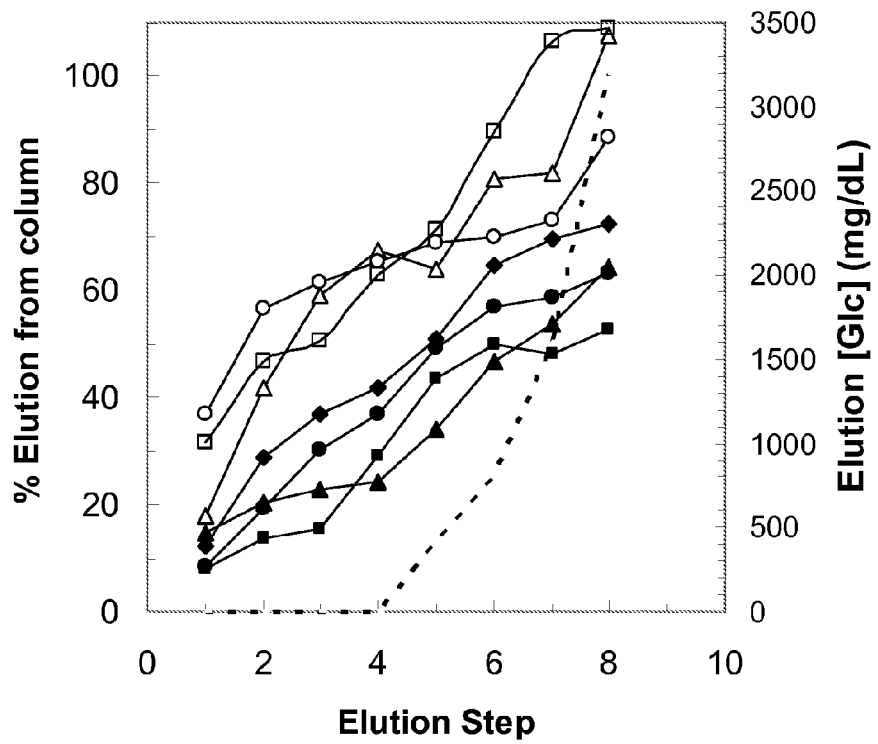
FIG. 1: shows individual monoclonal elution profiles from a glycogen bead column as a function of glucose. Open shapes—Monoclonals 1, 4 and 6. Closed shapes—Monoclonals 2, 3, 5, and 7. The dotted line refers to the glucose concentration used to elute at each step.

In order to determine the differences in monoclonal binding affinities for the glycogen resin, glycogen beads were added to a small column and washed extensively. The monoclonals were allowed to bind, and were then eluted with the binding step, followed by three wash steps with binding buffer. Next, the columns were eluted with 400, 800, 1600, and 3200 mg/dL glucose, and the optical density at 260 nm was measured at each step and plotted as a function of the original aptamer stock concentration (see FIG. 1). All monoclonals had an affinity for the glycogen beads, and all of them eluted from the column over a broad range of glucose values. However, a large portion (>50% of the total) of three of the bound sequences, 1, 4, and 6, washed off the beads even at zero glucose. Furthermore, >90% eluted from the column by 800 mg/dL, whereas <60% of the total amount bound for monoclonals 2, 3, 5, and 7 washed off the glycogen resin even at 3,200 mg/dl glucose. A comparison of the calculated secondary structure and sequence homology structure (FIG. 2) showed a strong correlation to the monoclonal glycogen-bead binding study results. Thus, the two sets of monoclonals provide two distinct pools of glycogen-binding aptamers with a range of low and high affinities, which could be used as a starting point for generating aptamers with a range of glycogen-binding affinities.

The structural homology between sequences was investigated using Mfold™ software, which is a free-energy minimization simulator to help predict possible secondary structures of the above monoclonals.

The structural results suggested that the evolved aptamer pool favors branched structures containing multiple 6 and 8 bp loops. Monoclonals 2, 3, and 7 contain nearly identical fold structures, and Monoclonal 5 contains some similarities to 2, 3, and 7. A re-examination of the monoclonal sequences (FIG. 2) shows that the 40 bp random region is very homologous between 2, 3, 5, and 7, and that the small differences in their sequences do not appear to affect their predicted fold structures. Monoclonals 4 and 6 differ dramatically in their sequence structure from the other 84 bp aptamers. Of particular note, however, is that the predicted fold structures for 4 and 6 share similar features to those of 2, 3, and 7.

Example 2

Self-Assembling Monomeric Glucose-Binding Aptamers into Multimers

A key design parameter for a glucose binding molecule to be used in an inventive material is that it must be multimeric, so it can form non-covalent crosslinks with the conjugate. Native Con A is tetrameric at physiological temperature and pH, and pegylated Con A is at least dimeric. Thus, in order for an RNA aptamer to be useful in the context of an inventive material, the aptamer must be made multimeric.

One convenient method for making multimeric constructs is the use of an avidin-biotin affinity tag system. Avidin, which is a native tetramer at physiological pH, is comprised of 4 monomers, each containing one binding site for biotin. The binding constant between biotin and avidin is extremely large ($10^{15}$ $M^{-1}$).

Figure 3:
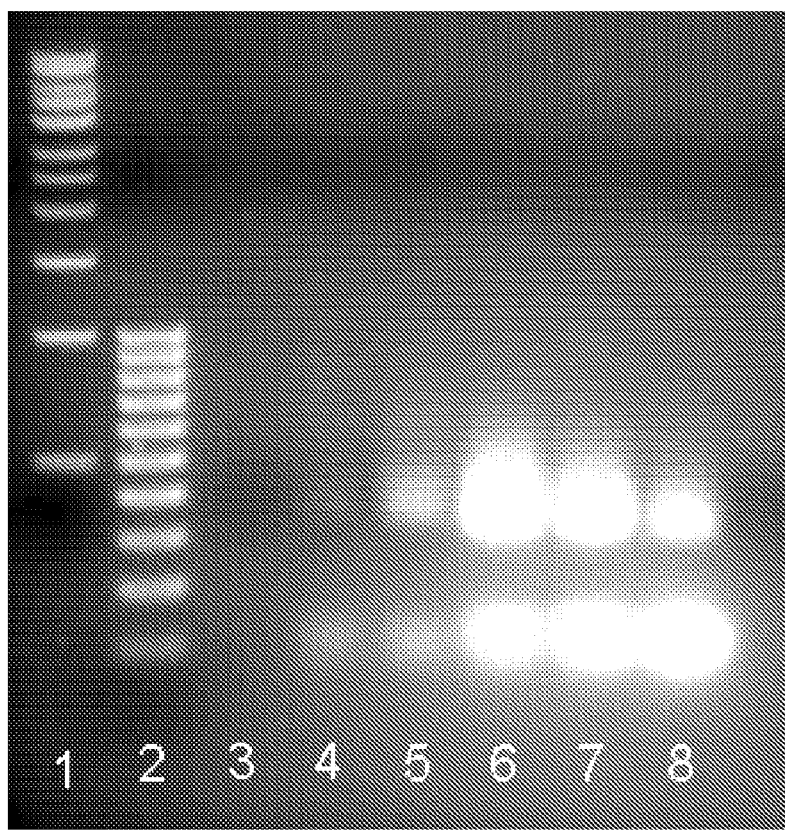
FIG. 3: shows picture of the following gels: Lane 1: 1,000-10,000 bp ladder; Lane 2: 100-1,000 bp ladder, Lane 3: avidin control; Lane 4: 1:2 mol. avidin:aptamer+10 mM biotin; Lane 5: 1:2 mol. avidin:aptamer; Lanes 6-8: 1:4, 1:8, and 1:16 mol. ratios of avidin:aptamer, respectively.

The monoclonal sequence 3 was truncated (bases 15-65, containing entire N40 region) in order to make the sequence more facile for chemical synthesis. Modified 2'-fluoro-pyrimidine RNA aptamer was synthesized by Dharmacon, Inc. from the 3' to 5' end, and a biotin tag was covalently bound to the terminal 5' end of the sequence. The sequence was desalted, HPLC, and gel purified by the manufacturer and was found to have an average of 1 mole of biotin tag per mole of sequence. Before use, we wanted to verify that avidin-biotinyl aptamer mixtures would give multimeric constructs. Avidin at 1.1 mg/ml was added at a constant concentration to serial dilutions of the biotinyl-aptamer to give avidin-biotinyl RNA molar ratios of 1:2, 1:4, 1:8, 1:16. These samples, along with control lanes were loaded onto a 1% agarose gel containing ethidium bromide were electrophoresed to demonstrate that avidin-biotinyl aptamers give higher MW complexes. The gel is shown in FIG. 3. The truncated biotinyl (non bound) sequence elutes at the 100 bp standard, while the multimeric avidin:aptamer complex elutes near the 400 bp ladder. Lanes 4 and 5 demonstrate that the specificity of binding is due specifically to the avidin-biotin interaction, since formation of the multimeric complex is inhibited in the presence of biotin. Also, it seems that a portion of the "biotinyl-aptamer" is not biotinylated, as at avidin-rich ratios (1:2, lane 5) there is a band migrating at the 100 bp standard.

Figure 4:
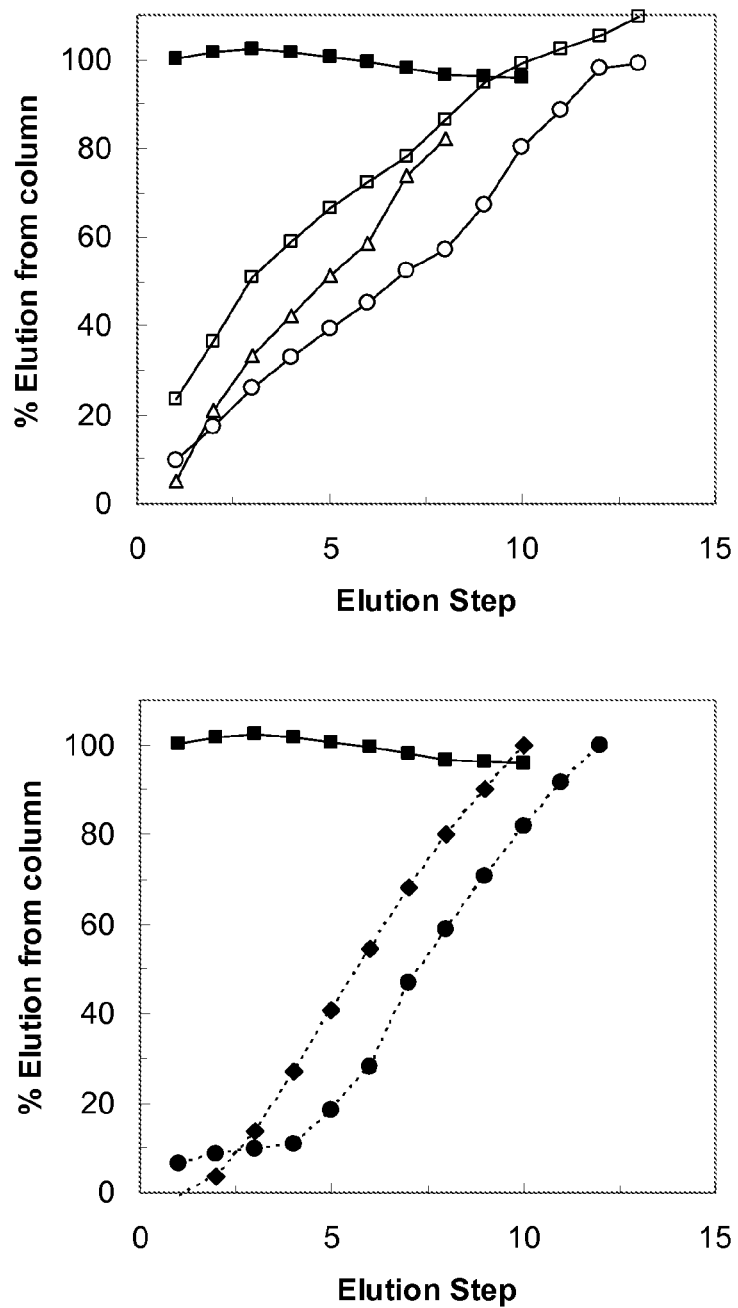
FIG. 4: (upper) shows biotinylated truncated aptamer 3 elution profiles from polyacrylamide bead column (■), glycogen bead column ( ), biotinylated aptamer mixed with avidin at a 4:1 aptamer:avidin molar ratio on glycogen bead column (○), and biotinylated aptamer only with glycogen bead column pre-equilibrated with 1600 mg/dL glucose prior to loading (□).

The truncated, biotinylated sequence was evaluated for its binding characteristics in the presence and absence of avidin on a glycogen bead affinity column. Column elution was measured by the optical density at 260 nm, and the binding profiles of the biotinyl aptamer sequence were compared to native Con A and pegylated Con A on the glycogen bead column (protein measured at 280 nm). A control column comprised of polyacylamide beads was also used to represent the case of no stationary phase binding. The results are shown in FIG. 4.

Con A and the monomeric biotinyl-aptamers elute immediately from the polyacrylamide column and elute slowly from the glycogen column over a broad range of glucose values. The 4:1 aptamer-avidin molar mixture of multimers (see FIG. 3) displays an enhanced affinity for the glycogen column, requiring higher glucose levels than the monomeric biotinyl-aptamers. In order to prove that the aptamer interaction with the column is specific for glucose/glycogen, another fresh glycogen column was equilibrated with 1600 mg/dl glucose prior to loading the monomeric biotinyl-aptamers (no avidin). The pre-loading equilibration with glucose led to more aptamer elution at lower glucose values, indicating that the biotinyl aptamer-glycogen bead interaction is a highly specific one that can be inhibited by the presence of glucose at high concentrations.

Example 3

Monomeric Aptamer Pools with Varied Conjugate Binding Affinities

Mutating Monoclonals Separately to Create Diverse Pools of Binders cDNA monoclonals are made with manganese salts in PCR by mixing 6 uL of 10×PCR Buffer, 6 uL of dNTPs 2 mM, 24 uL each of 5' and 3' Primers, 6 uL of Taq Polymerase and the rest of the PCR tube volume is filled with $MnCl_2$ and distilled deionized $H_2O$ at a serial dilution of $MnCl_2$ between 2 mM to 0625 mM to find the right concentration of $MnCl_2$ as measured by agarose gel electrophoresis. PCR is then run @ 30 cycles @ 95° C. for 45 seconds, 53° C. for 45 seconds, and 72° C. for 1 minute.

SELEX Protocol

Mutated, modified RNA pools are mixed with protein-free Oyster glycogen (Type II, Sigma Aldrich) and allowed to equilibrate at 37 C for 15 minutes. After this time, 100 ul of the glycogen/modified RNA solution is loaded onto a 1 mL capacity P-100 spin column equilibrated at 37 C, and the sample is centrifuged to remove unbound oligonucleotide, while allowing the glycogen-aptamer complex to pass through. A low concentration of glucose is added to the glycogen-aptamer mixture, which is passed through a fresh P-100 spin column again. This time, some aptamer-glycogen complex may be inhibited by glucose and stay in the spin column, while the glycogen is removed. The contents of the spin column, now free of glycogen, are simply eluted with 3×100 ul wash with binding buffer. The process is repeated for a range of glucose concentrations to obtain a diverse number of glucose pools. The obtained sequence(s) are reverse-transcribed into cDNA and amplified for the next round of transcription and selection. Monoclonal sequences can be obtained after several rounds of selection. The criteria for success includes measuring the A260 of the glycogen-aptamer complex as a function of glucose. If the pool is enriching toward higher glucose values then more aptamer should be bound to the glycogen, giving a measurably higher OD260 value for the glycogen-bound aptamer complex solution.

Example 4

Chemically Synthesized Multimeric Aptamers

Monoclonals identified in Example 3 are sequenced and chemically synthesized on a small scale using a chemical synthesizer, or on larger scales (>2 mg scale) from a manufacturer. These are covalently labeled with a 5'-thiol using a biotin phosphoramidite (Glen Research, Sterling, Va.) during the final round of chemical base synthesis.

The modified, thiolated RNA aptamer is then reacted in a modified binding buffer (50 mM HEPES, pH 6.8-7.0, 100 mM NaCl, with 1 mM $MgCl_2$) with a very slight molar excess (1.05:1) dimeric, trimeric, or tetrameric maleimide functionalized molecule also dissolved in the binding buffer. The maleimide will undergo a facile reaction with the 5'-modified aptamer at room temperature within minutes to give a stable thioether linkage between the aptamer and the multimeric spacer molecule. If dimers are desired, then bis-maleimidohexane (Pierce, Rockford, Ill.) are used, or if trimeric aptamers are desirable, then tris-(2-maleimidoethyl)amine are used to easily react with aptamer sulfhydryls.

The different monomeric monoclonal glycogen binding affinities, when formed as dimers or trimers should be capable of forming crosslinked hydrogels with glycogen or other drug-conjugates. The glucose responsiveness of the resulting materials can then be tested.

Example 5

Optimizing Aptamer-Drug-Conjugate Glucose-Responsive In Vitro Kinetics

This example involves synthesizing hydrogels using a drug-conjugate and a corresponding multivalent aptamer as outlined in Example 4.

Gel Crosslinking Experiments and Determination of Conjugate Release Kinetics

Each multimeric aptamer produced in Example 4 is dissolved at 50 mg/ml in a 50 mM HEPES buffer (pH=7.4) containing 10 mM $MgCl_2$ and 100 mM NaCl. Each drug-conjugate solution is prepared at 100 mg/ml in the same buffer. The drug-conjugate solutions are then diluted by a factor of two from 50 mg/ml to 6.25 mg/ml using the same buffer. 50 μL of drug-conjugate solution is then added to a 250 ml conical centrifuge tube, after which an equal volume of the multimeric aptamer solution is added, and the resulting solution mixed rapidly. The solutions are left to stand for 1 hr, after which any resulting aggregates are isolated by centrifugation at 360×g for 10 min (Allegra 21R, Beckman Coulter, Fullerton, Calif.). The supernatant is removed and stored for the drug measurement assay. The crosslinking efficiency ($Xc_L$) for each experiment is then determined from the difference in drug content before and after separation of the crosslinked aggregates. The formulations resulting in self-contained gels are then washed three times with buffer for 15 min, followed by centrifugation at 360×g for 10 min After removing the last wash solution, the gels are kept at 4 C overnight, and used subsequently for kinetic studies.

Using a kinetic assay, 1.0 ml of 50, 100, 200 and 400 mg/dl of D-glucose is added to each of 4×3 ml wells of a Multi-well™ 24 well plate (Becton Dickson). Each gel is then added to the solution and agitated at 37 C using a microplate incubator/shaker ("Jitterbug," Boekel Instruments). For example, for an insulin assay 125 ul of the release medium is removed every 15 min at first followed by every half hour after the first hour of the experiment. Each time, the release medium is supplemented with 0.125 ml of the same concentration of glucose. This process is repeated for at least 6 hours. The drug-conjugate dissolution at each time point will then be measured by ELISA (ALPCO Diagnostics) and the cumulative release of drug plotted as a function of time at each concentration. By fitting a line through the initial slopes of the release curves at each glucose concentration, the $R_{50}$, $R_{100}$, $R_{200}$, and $R_{400}$ values are readily obtained.

Example 6

Optimal Single-Dose Formulation for Fasting and Mealtime Glucose Control

The optimal dosage formulation and volume of an aptamer based material is determined by evaluating the extent and duration of reduced blood glucose levels and increased serum insulin-conjugate concentrations in STZ-induced diabetic rats. Rats (n=6) are fasted while providing water ad libitum for six hours prior to measuring blood glucose levels. Because each administration has a limited insulin capacity, fasting blood glucose levels are measured until a return to hyperglycemia is observed in order to establish the "lifetime" of each formulation. Those single dose formulations capable of reducing fasting glucose levels for at least three days are also evaluated for their ability to confront an intraperitoneal glucose tolerance test (IPGTT) administered on day one and day two of the experiment.

Induction of STZ-diabetes in SD rats (200-250 g) is done with an 60 mg/kg STZ (4% w/v in 0.1 M citrate buffer) i.p. injection using a 1 ml capacity syringe equipped with a 27 gauge-1 inch needle. Blood glucose levels are measured after a six hour fast on day five and day six post-STZ injection. Only those rats having fasting glucose levels >350 mg/dl for two consecutive days are used for the subsequent studies. Blood glucose levels in general are measured using test strips (Precision QID) and a MediSense glucometer from approximately 20 μl of blood extracted from the tail vein.

Serum insulin-conjugate levels are measured using a commercially available human insulin ELISA kit (Alpco Diagnostics, Windham, N.H.). To obtain samples for serum concentration determination, 250-500 μL of blood is extracted from the tail vein, centrifuged to separate cells from serum and stored at −20 C prior to ELISA. Intraperitoneal glucose tolerance test (IPGTT) are performed on fasted rats by i.p. injection of a 45% w/v D-glucose solution (Sigma-Aldrich, St. Louis, Mo.) at a dose of 1 g/kg of D-glucose. Throughout the experiment, blood samples (500 μL) are taken from the tail vein at t=−10, −5, 0, 5, 10, 15, 20, 25, 30, 40, 50, 60, 75, 90, 120, and 180 min to determine both blood glucose and serum insulin-conjugate levels. The peak glucose concentrations ($G_{max}$), time to peak glucose concentration ($T_{Gmax}$), and time to return to fasting blood glucose levels ($T_{fast}$) are compared to determine the ability of various formulations to confront the glucose load. Normal, non-diabetic rats (n=6) are used as controls to which all pharmacodynamic parameters will be compared.

Long-acting insulin supplements (Lantus®, Aventis Pharmaceuticals, 2 U) are provided to STZ-rats via s.c. injection to decrease blood glucose levels one day prior to each glucose-responsive formulation injection. Six of the experimental animals are provided "empty" formulations (i.e., without conjugated insulin) and six are provided with 1×PBS solutions as controls. The remaining rats are given the glucose-sensitive gel injections. Glucose-responsive gels constructed from both insulin-dextran and insulin-glycogen conjugates ($G_{10\%}$~50 mg/dl and 100 mg/dl) are injected at two different dosage levels (0.20 ml and 0.40 ml batch size). In addition, two different insulin-conjugate loadings are evaluated by synthesizing gels with (i) 100% insulin-conjugate and (ii) 50% insulin-conjugate and 50% unconjugated polymer.

Dosage frequency is determined by assuming a linear correlation between the injection volume of the optimal formulation and the duration of fasting blood glucose level control. The dosage volume is then scaled back to provide a single day of fasting blood glucose control. This volume (V), 80% of V, and 120% of V is injected s.c. into STZ-induced diabetic rats (n=6) once each morning and fasting blood glucose and serum insulin levels are measured each day for a total of seven days. The volume that provides the most stable (minimal increase or decrease) fasting blood glucose and serum insulin levels over the course of one week is used for the refinement of glucose set-point and insulin-conjugate loading experiments.

Glucose sensitivity adjustment for maximal control is achieved by increasing the glucose set point (GSP) assay setpoints by adjusting the ratio of aptamer to insulin-conjugate. Depending on the results of the previous dosage formulation, volume, and frequency experiments, gels are used at the optimized volume and dosage level. Formulations having a $G_{10\%}$ of 75, 90, 105, 120, and 135 mg/dl are injected into STZ-induced diabetic rats (n=6) once each morning for seven consecutive days. For each set point, insulin-conjugate loading is set to 50%, 75%, and 100% to further optimize the most appropriate insulin-conjugate concentration to prevent hypoglycemia while minimizing hyperglycemia. On each day, fasting blood glucose and serum insulin levels is measured prior to performing IPGTT as described above.

The average fasting blood glucose concentration as well as the average $G_{max}$, $T_{Gmax}$, and $T_{fast}$ from IPGTT is correlated to the glucose set points and insulin loadings of each injected formulation. Materials with higher glucose set-points should result in higher glucose concentrations over time than those programmed to dissolve at lower glucose concentrations.

Example 7

Verifying Increased Serum Half-Life of Aptamers

Oligonucleotides constructed from 2'-fluoro-pyrimidines have exhibited nuclease stability half-lives greater than several hours in vitro (e.g., see Dougan et al., Extending the lifetime of anticoagulant oligodeoxynucleotide aptamers in blood. *Nucl Med Biol* 2000, 27, (3), 289-97; Beigelman et al., Chemical modification of hammerhead ribozymes. Catalytic activity and nuclease resistance. *J Biol Chem* 1995, 270, (43), 25702-8; and Scaringe et al., Chemical synthesis of biologically active oligoribonucleotides using beta-cyanoethyl protected ribonucleoside phosphoramidites. *Nucleic Acids Res* 1990, 18, (18), 5433-41).

Therefore, free aptamers constructed from these modified bases would not survive a 24 hour dosing cycle. Nevertheless, we predict that while trapped within an inventive material, the aptamers are even more resistant to nuclease degradation based on steric hindrance. Therefore, a $t_s$>300 min should be sufficient to prevent excessive nuclease degradation of an inventive material over the lifetime of the daily dosage. This example provides experiments which can be used to confirm this prediction by determining the extent of drug-conjugate leakage from an inventive material in the presence of nucleases.

In vitro stability of the aptamers is determined by dispersing 0.02 µCi of the purified [$^{125}$I]-labeled aptamers in 20 µl of the appropriate fluid—human serum, human plasma, rat serum, and rat plasma (Sigma-Aldrich, St. Louis, Mo.) (e.g., see Dougan et al., supra). The samples are then be incubated at 37° C., and 2 µl aliquots withdrawn at time intervals between 30 and 72 h (e.g., see Beigelman et al., supra). Aliquots are quenched by the addition of 20 µl of 95% formamide, 0.5×TBE (50 mM Tris, 50 mM borate, 1 mM EDTA) and frozen prior to gel loading. Finally, the samples from each time point are fractionated by denaturing gel electrophoresis on 20% polyacrylamide followed by imaging using an Auto-Radiographer. The in vitro stability half-life ($t_s$) for each aptamer is calculated from exponential fits of plots of the percent of intact aptamer versus the incubation time (e.g., see Beigelman et al., supra).

In vivo elimination half-life is determined using a modified pharmacokinetic analysis procedure (e.g., see Dougan et al.; Scaringe et al., both supra; and Santulli-Marotto et al., Multivalent RNA aptamers that inhibit CTLA-4 and enhance tumor immunity. *Cancer Res.* 63:7483-7489, 2003). Briefly, Male Sprague-Dawley rats (Taconic, Germantown, N.Y.) weighing 200-250 g are injected both intravenously (i.v., n=6) and subcutaneously (s.c., n=6) with a sterilized, 1×PBS solution of [$^{125}$I]-labeled aptamer (0.25 ml containing 10 µCi). Throughout the experiment, blood samples (300 µl) are taken from the tail vein at t=0, 5, 15, 60, 120, 240, 480, 960, and 1440 min, centrifuged for one minute at 10,000 g at 4° C. to harvest the plasma, and stored at −20° C. until analyzed for radioactivity using a scintillation counter. The in vivo elimination half-life ($t_{1/2}$) for each aptamer is calculated by estimation from the terminal linear segment of the plasma concentration vs. time curve. For the purpose of this experiment, i.v. injections are administered with a 27 gauge, ½-inch needle into the tail veins and s.c. injections are administered with a 27 gauge, ½-inch needle into the back of the neck.

Example 8

Assessing Glucose Dependent Drug-Conjugate Release

This example describes in vitro and in vivo methods which can be used to assess the extent of drug-conjugate release from an inventive material in the presence of glucose.
In Vitro Glucose Set-Points in Serum A glucose set point (GSP) assay is performed using human and rat serum instead of PBS for each glucose incubation stage. First, 1.0 ml of serum containing 50 mg/dl of D-glucose is added to each of the 24×3 ml wells of a Multiwell™ 24 well plate (Becton Dickson). Each gel (prepared from fluorescent conjugates) is added to the solution and agitated at 37° C. for one hour using a microplate incubator/shaker ("Jitterbug," Boekel Instruments). After one hour, 0.5 ml of the release medium is removed and analyzed for fluorescence ($\lambda_{ex}$=485 nm; $\lambda_{em}$=538 nm). The release medium is then supplemented with 0.5 ml of serum containing 150 mg/dl of glucose to make a 100 mg/dl solution and the gels are agitated for another hour. This process is repeated for release medium glucose concentrations of 200, 400, 800, and 1600 mg/dl for a total of 6 concentrations over 6 hours. The cumulative conjugate dissolution is then calculated by normalizing the cumulative concentration of conjugate in the release medium by that released at 100% dissolution. $G_{10}$% and $G_{50}$% are determined by plotting cumulative release as a function of glucose concentration and estimating the glucose concentration at which 10% and 50% of the conjugate is released, respectively.
In Vivo Fasting Blood Glucose Levels Gels ($G_{10\%}$~50 mg/dl and 100 mg/dl) are injected subcutaneously into the back of the necks of male Sprague-Dawley rats weighing 200-250 g (n=6) at a dose of 0.2 mg insulin/kg of body weight using a 27 gauge ½ inch needle. For the negative controls, sterile 1×PBS solutions are also injected subcutaneously (n=6). The experimental and control groups are then fasted while providing water ad libitum for six hours prior to measuring blood glucose levels. Fasting blood glucose levels are then measured using test strips (Precision QID) and a MediSense glucometer from approximately 20 µl of blood extracted from the tail vein.

Example 9

Quantifying Subcutaneous Injection Compatibility

The subcutaneous biocompatibility of inventive materials is assessed by acute inflammatory response and systemic antibody production. Each gel is evaluated for its capacity to induce inflammation at the injection site. In each case, materials are injected under the skin of the right hind quarter of six normal SD rats (200-250 g body weight) using a 0.5 ml capacity syringe equipped with a 27 gauge ½ inch needle.

For each separate material evaluation, rats are euthanized in a carbon dioxide chamber five days after injection to allow enough time to develop an acute immune response. Any tissue exhibiting an adverse acute inflammatory response is excised along with comparably sized contralateral control samples for histological examination (Advanced Microscopy Lab, Joslin Diabetes Center, Boston, Mass.). The samples are then fixed in 4% paraformaldehyde for a minimum of three days, dehydrated in ethanol, and then cleared in xylene (e.g., see The and Feltkamp, *Immunology* 18:875-81, 1970). After fixation, the tissue is embedded in paraffin under vacuum and sectioned into 12 µm thick planes. Histologic staining with hematoxylin and eosin is used to determine fibrous capsule and necrotic tissue thickness. In addition, immunochemical labeling with ED1 is used to assess macrophage density. Finally, toluidine blue is used to assess the infiltration of granulocytes and lymphocytes (e.g., see The and Feltkamp, *Immunology* 18:865-73, 1970). A histological score is given to each section and a student t-test (p<0.05) is used to verify that the difference in localized lymphocyte and macrophage densities is less than 10% of the control rat population.

In order to investigate whether systemic conjugate- or aptamer-specific antibody levels are elevated in the presence of an inventive system, a standard immunization protocol is performed on each gel formulation. In each case, materials are injected on days 1, 14, and 28 under the skin of the back of the neck of six normal SD rats (200-250 g body weight) using a 0.5 ml capacity syringe equipped with a 27 gauge ½ inch needle. Blood samples (500 µl) are taken before the experiment and on days 28 and 35. Each sample is centrifuged for one minute at 10,000 g at 4° C. to harvest the serum, and stored at −20° C. until analyzed for antibody concentration. For these experiments, 1×PBS solutions (n=6) serve as negative controls and Freund's complete adjuvant (Sigma-Aldrich, St. Louis, Mo.) plus conjugate (n=6) and aptamer (n=6) serve as positive controls.

Custom-made enzyme-linked immunosorbent assays (ELISA's) targeted to the aptamer and conjugates (Proteo-Cell Biotechnologies, Inc., Quebec, Canada) are used to measure the concentration of specific IgG, IgA, IgM and IgE-class antibodies relative to the negative controls. Briefly, the target material is adsorbed to the surface of a 96-well plate by incubating each well with 100 µl of a 1-10 µg/ml solution followed by the addition of blocking buffer, washing, drying, and storage at 4° C. After addition of and incubation with an appropriately diluted serum solution, an antibody-HRP conjugate (anti-IgG, IgA, IgM and IgE is added followed by a TMB substrate and stop solution all from a commercially available kit (Alpha Diagnostics, San Antonio, Tex.)). The intensity of the resulting yellow color is read at 450 nm using a UV-visible absorbance plate reader (SpectraMax, Molecular Devices, Sunnyvale, Calif.) and correlated to the relative concentration of antibodies.

Example 10

Reducing 30-Day $HbA_{1c}$ Levels in Diabetic Rats

Reduction in $HbA_{1c}$ levels are determined for the optimized once-a-day formulation from Example 6 and compared to daily injections of long-acting Lantus® (Aventis Pharmaceuticals, Bridgewater, N.J.) as well as sustained release implants (Linplant®, LinShin Canada Inc., 1.5 implants, 3 U/day constant release). $HbA_{1c}$ levels are measured using 20 µL of blood placed on a capillary holder that is subsequently inserted into a reagent cartridge and analyzed using a $HbA_{1c}$ blood glucose meter (DCA 2000® Analyzer, Bayer Healthcare LLC, Elkhart, Ind.).

Each experimental group (inventive system, Lantus®, and Linplant®) consists of 12 STZ-induced diabetic rats. The rats are injected each morning for 60 consecutive days. Every three days throughout the course of the experiment, blood glucose and serum insulin levels are measured in the morning and evening. $HbA_{1c}$ levels are measured after 14 days and 30 days of treatment and correlated to the type of treatment. An absolute value reduction of 0.5% in $HbA_{1c}$ levels (p<0.05) or more will verify the ability of our optimized formulation to provide significantly better glycemic control when administered daily as a s.c. injection.

Example 11

Materials and Methods

This example describes some of the materials and methods that are used in the previous examples.
Radiolabeled Aptamers These are prepared with specific activity of 1,000-2,000 Ci/mmole according to previously published methods (e.g., see Dougan et al., supra) using [$^{125}$I]NaI in 0.1 N NaOH (Amersham Biosciences, Piscataway, N.J.). Radioactive aptamers are easily prepared as the sodium salts using commercial Centri-Spin-10 size exclusion columns following the supplier's directions (Princeton Separations, Adelphia, N.J.).
Insulin-Glycogen Conjugate This is synthesized using a modified cyanogen bromide (CNBr) coupling reaction (e.g., see Kagedal and Akerstrom, *Acta. Chem. Scand.* 25: 1855-159, 1974). Briefly, 500 mg of glycogen is dissolved in 50 ml of deionized water. 56 mg of solid CNBr is added to the resulting solution and the pH maintained constant at 10.7+/−0.2 using 5 N sodium hydroxide (NaOH) solution. After stirring for 15 minutes, another 56 mg of solid CNBr is added and the pH maintained constant at 10.7+/−0.2 while stirring for 45 minutes. 50-250 mg of human recombinant insulin (Sigma-Aldrich, St. Louis, Mo.) is then added to the solution and the pH adjusted to 9.15 using solid sodium bicarbonate. The solution is stirred overnight, ultrafiltered exhaustively against deionized water using a 10 K MWCO polyethersulfone disc membrane filter (Millipore, Bedford, Mass.), and lyophilized. The resulting powder is then purified from unconjugated insulin by high-performance liquid chromatography (Waters, Milford, Mass.) using a 1 M acetic acid mobile phase over a Superdex™ 75 (Amersham Biosciences, Piscataway, N.J.) packed column. The conjugated fraction is then lyophilized to obtain the conjugate as a pure white powder. The degree of insulin conjugation is determined by UV spectroscopy and amino acid analysis (UCLA Biopolymers Laboratory).
Chemically Crosslinked Glycogen This is synthesized using a modified CNBr coupling procedure and provides the aptamer selection stationary phase. Briefly, 2 g of glycogen is dissolved in 50 ml of deionized water. 225 mg of solid CNBr is added to the resulting solution and the pH maintained constant at 10.7+/−0.2 using 5 N sodium hydroxide (NaOH) solution. After stirring for 15 minutes, another 225 mg of solid CNBr is added and the pH maintained constant at 10.7+/−0.2 while stirring for 45 minutes. The pH is then adjusted to 9.15 using solid sodium bicarbonate, and the resulting dispersion is stirred overnight. The crosslinked glycogen is then centrifuged at 3,000×g for 10 min and washed exhaustively with 1×PBS, and then aptamer binding buffer (50 mM HEPES, pH 7.4, 100 mM NaCl, 10 mM $MgCl_2$. The particles are kept at 4° C. until needed.
Pegylated-Con A This is prepared by dissolving 500 mg of Con A in 50 ml of a 100 mM pH 7.4 BES buffer containing 1.0 M NaCl, 1 mM $Ca^{2+}$ and $Mn^{2+}$. A desired amount of PEGylation agent (e.g., PEG-SMB-5k, Nektar Therapeutics, Huntsville, Ala.) is dissolved in a small volume of reaction buffer and slowly added to the Con A solution. The resulting solution is allowed to react overnight at room temperature, followed by exhaustive filtration via a tangential flow membrane with a cutoff of 50 kDa (Millipore, Billerica, Mass.). Once purified of free PEG reagent, the solution is concentrated in an ultrafiltration cell (Amicon, Millipore, Billerica, Mass.) until the concentration is 100 mg/ml Con A equiv. by assaying the absorbance at 280 nm The % PEGylation is determined by normalizing the absorbance of a 1 mg/ml solution at 278 nm to that of unmodified Con A and also by polyacrylamide gel electrophoresis (SDS-PAGE).

Glucose-Responsive Gels

These are synthesized by combining 0.100 ml of a 100 mg/ml aptamer (or Con A) solution with 0.100 ml of a 5-100 mg/ml conjugate solution through co-injection through a dual syringe apparatus. For in vitro studies, the resulting gels are deposited in a 1.5 ml centrifuge tube for one hour, after which the resulting gels are separated from the supernatant and washed twice with 1 ml of deionized water and then twice with 1 ml of 1×PBS before being stored at 2-8 C for GSP or kinetic studies.

Example 12

Conjugates of Formula (I)

This example describes some exemplary conjugates of formula (I):

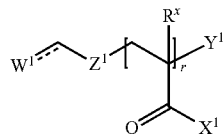

Yet other embodiments of these conjugates as well as intermediates and methods of making these conjugates can be found in U.S. Provisional Application No. 61/162,105 filed Mar. 20, 2009 and corresponding PCT application filed on Jan. 27, 2010. The entire contents of these related applications are incorporated herein by reference.

In certain embodiments, a conjugate of formula (I) may include one or more of the following exemplary groups:

$R^x$

In certain embodiments, $R^x$ is hydrogen. In certain embodiments, $R^x$ is optionally substituted $C_{1-6}$ alkyl. In certain embodiments, $R^x$ is optionally substituted $C_{1-3}$ alkyl. In certain embodiments, $R^x$ is optionally substituted methyl. In certain embodiments, $R^x$ is —$CH_3$.

$Z^1$

In certain embodiments, $Z^1$ is an optionally substituted bivalent $C_{1-10}$, $C_{1-8}$, $C_{1-6}$, $C_{1-4}$, or $C_{1-2}$ hydrocarbon chain. In certain embodiments, $Z^1$ is —(CH$_2$)—, —(CH$_2$CH$_2$)—, —(CH$_2$CH$_2$CH$_2$)—, —(CH$_2$CH$_2$CH$_2$CH$_2$)—, —(CH$_2$CH$_2$CH$_2$CH$_2$CH$_2$)—, or —(CH$_2$CH$_2$CH$_2$CH$_2$CH$_2$CH$_2$)—. In certain embodiments, $Z^1$ is —(CH$_2$)— or —(CH$_2$CH$_2$)—. In certain embodiments, $Z^1$ is —(CH$_2$)—. In certain embodiments, $Z^1$ is —(CH$_2$CH$_2$)—. In certain embodiments, $Z^1$ is —(CH$_2$CH$_2$CH$_2$)—. In certain embodiments, $Z^1$ is —(CH$_2$CH$_2$CH$_2$CH$_2$)—.

In certain embodiments, $Z^1$ is an optionally substituted bivalent $C_{1-10}$ hydrocarbon chain, wherein 1, 2 or 3 methylene units of $Z^1$ are optionally and independently replaced with one or more groups selected from —S—, —O—, —NR$^a$—, —(C=NR$^a$)—, —(C=O)—, —(S=O)—, —S(=O)$_2$—, —(CR$^b$=CR$^b$)—, —(N=N)—, an optionally substituted arylene moiety or an optionally substituted heteroarylene moiety. In certain embodiments, $Z^1$ is an optionally substituted bivalent $C_{1-10}$ hydrocarbon chain, wherein 1, 2 or 3 methylene units of $Z^1$ are optionally and independently replaced with one or more groups selected from —S—, —O—, —NR$^a$—, —(C=NR$^a$)—, or —(C=O)—. In certain embodiments, $Z^1$ is —CH$_2$CH$_2$NH(C=O)C(CH$_3$)$_2$—, —CH$_2$CH$_2$N(C=NH)(CH$_2$)$_3$S—, —CH(R$^f$)$_2$, —CH$_2$CH(R$^f$)$_2$, —CH$_2$CH$_2$CH(R$^f$)$_2$—, —CH$_2$S—, or —CH$_2$CH$_2$S—, wherein R$^f$ is optionally substituted aliphatic, optionally substituted heteroaliphatic, optionally substituted aryl, optionally substituted heteroaryl (e.g., in certain embodiments, R$^f$ is optionally substituted aryl; in certain embodiments, R$^f$ is phenyl). In certain embodiments, $Z^1$ is —CH$_2$CH$_2$NH(C=O)C(CH$_3$)$_2$— or —CH$_2$CH$_2$N(C=NH)(CH$_2$)$_3$S—. In certain embodiments, $Z^1$ is —CH$_2$CH$_2$NH(C=O)C(CH$_3$)$_2$—. In certain embodiments, $Z^1$ is —CH$_2$CH$_2$N(C=NH)(CH$_2$)$_3$S—.

$Y^1$

In certain embodiments, $Y^1$ is a fragment of a free radical initiator. Such a fragment is encompassed by the definition of $Y^1$, as initiator fragments may include halogen, —OR$^e$, —SR$^e$, optionally substituted aliphatic, optionally substituted heteroaliphatic, optionally substituted aryl, and optionally substituted heteroaryl moieties.

In certain embodiments, $Y^1$ is hydrogen, halogen, or an initiator fragment. In certain embodiments, $Y^1$ is hydrogen or halogen. In certain embodiments, $Y^1$ is hydrogen or bromine.

$X^1$

In certain embodiments, $X^1$ is —OR$^c$. In certain embodiments, $X^1$ is a mixture of —OR$^c$ and —N(R$^d$)$_2$. In certain embodiments, $X^1$ is —N(R$^d$)$_2$.

$W^1$ and ------

In certain embodiments, ------ is a single covalent bond.

In certain embodiments, $W^1$ is covalently bound to the polymer via an amino group. In certain embodiments, $W^1$ is covalently bound to the polymer via a primary amino group.

For example, in certain embodiments, the group

corresponds to the group

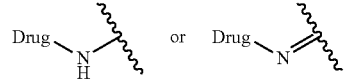

wherein the group [Drug-NH—] or [Drug-N=] is the drug directly covalently conjugated via a primary amino group. In other embodiments, the drug may include a spacer group (e.g., an alkylene group, arylene group, heteroarylene group, ester linkage, amide linkage, and the like) which terminates with a pendant amino group. The latter embodiments enable greater separation between the active portion of the drug and the polymer.

r

In certain embodiments, r is an integer between 10-25, inclusive. In certain embodiments, r is an integer between 15-25, inclusive. In certain embodiments, r is an integer between 20-25, inclusive. In certain embodiments, r is an integer between 5-20, inclusive. In certain embodiments, r is an integer between 10-20, inclusive. In certain embodiments, r is an integer between 15-20, inclusive. In certain embodiments, r is 5, 6, 7, 8, 9, 10, 11, 12, 13, 14, 15, 16, 17, 18, 19, 20, 21, 22, 23, 24 or 25. In certain embodiments r is 5. In certain embodiments r is 10. In certain embodiments r is 15. In certain embodiments r is 20. In certain embodiments r is 25.

In certain embodiments, the group:

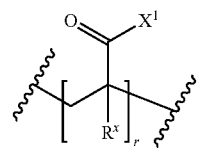

corresponds to a mixture of the groups:

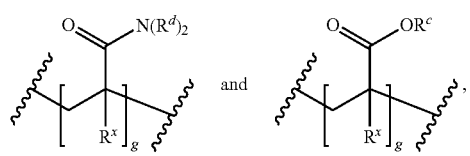

wherein the sum of (g+t) is equal to r. In certain embodiments, each instance of g and t is, independently, an integer between 1 and 24, inclusive, with the proviso that the sum of (g+t) is greater than or equal to 5 and less than or equal to 25. In certain embodiments, g and t are present in a ratio of about 1:10, 1:9, 1:8, 1:7, 1:6, 1:5, 1:4, 1:3, 1:2, or 1:1 (g to t). In certain embodiments, t and g are present in a ratio of about 1:10, 1:9, 1:8, 1:7, 1:6, 1:5, 1:4, 1:3, or 1:2 (t to g).

Exemplary Conjugates

In certain embodiments, a conjugate of formula (I-a1) may be used:

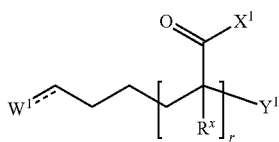

In certain embodiments, a conjugate of formula (I-a2) may be used:

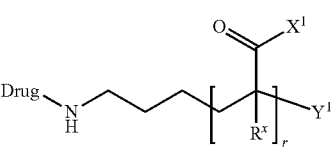

In certain embodiments, a conjugate of formula (I-b1) may be used:

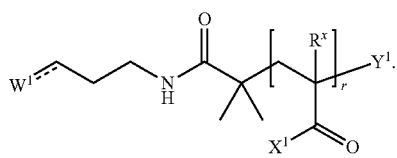

In certain embodiments, a conjugate of formula (I-b2) may be used:

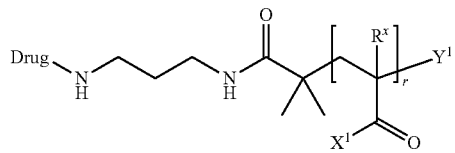

In certain embodiments, a conjugate of formula (I-c1) may be used:

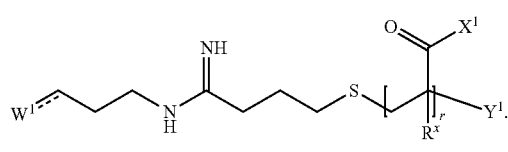

In certain embodiments, a conjugate of formula (I-c2) may be used:

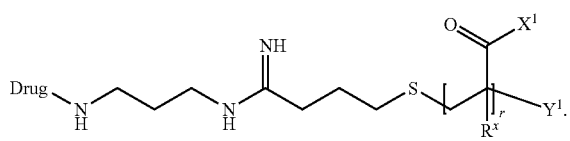

In any of these exemplary conjugates, the group:

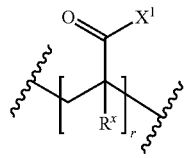

may correspond to a mixture of the groups:

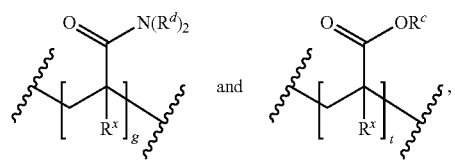

wherein the sum of (g+t) is equal to r, respectively. In certain embodiments, r is 10. In certain embodiments, r is 20.

Characterization of Conjugates

The conjugates can be characterized by any analytical method including nuclear magnetic resonance (e.g., $^1$H NMR); gel permeation chromatography (GPC) for molecular weight and polydispersity; and Fourier transform infrared spectroscopy (FTIR) or acid titration for determination of the number of acid groups per chain.

In certain embodiments the conjugate framework (i.e., without including the affinity ligands, drug or detectable label) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

In certain embodiments, a mixture of conjugates is generated. The conjugates in this mixture may have the same or different molecular weights. In one embodiment, the polydispersity of the mixture is less than 1.5. In one embodiment, the polydispersity of the mixture is less than 1.25.

Example 13

Conjugates of Formula (II)

This example describes some exemplary conjugates of formula (II):

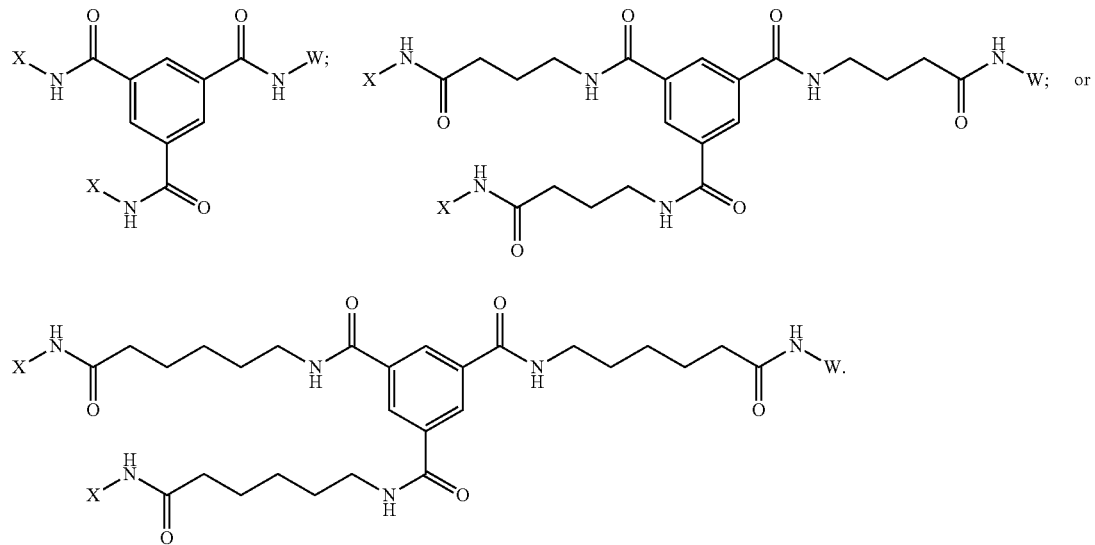

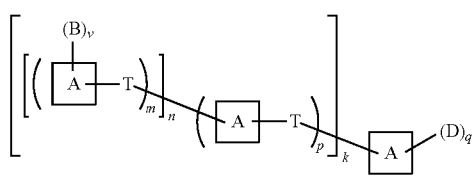

filed Mar. 12, 2009, U.S. Provisional Application No. 61/162,107 filed Mar. 20, 2009, U.S. Provisional Application No. 61/163,084 filed Mar. 25, 2009, U.S. Provisional Application No. 61/219,897 filed Jun. 24, 2009, U.S. Provisional Application No. 61/223,572 filed Jul. 7, 2009, U.S. Provisional Application No. 61/252,857 filed Oct. 19, 2009, and corresponding PCT application filed on Jan. 27, 2010. The entire contents of these related applications are incorporated herein by reference.

In some embodiments, the present disclosure provides conjugates of general formula (II-a1):

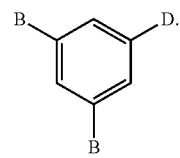

For example, in some embodiments, the present disclosure provides conjugates of formula:

In some embodiments, the present disclosure provides conjugates of general formula (II-a2):

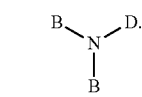

Yet other embodiments of these conjugates as well as intermediates and methods of making these conjugates can be found in U.S. Provisional Application No. 61/147,878 filed Jan. 28, 2009, U.S. Provisional Application No. 61/159,643

For example, in some embodiments, the present disclosure provides conjugates of formula:

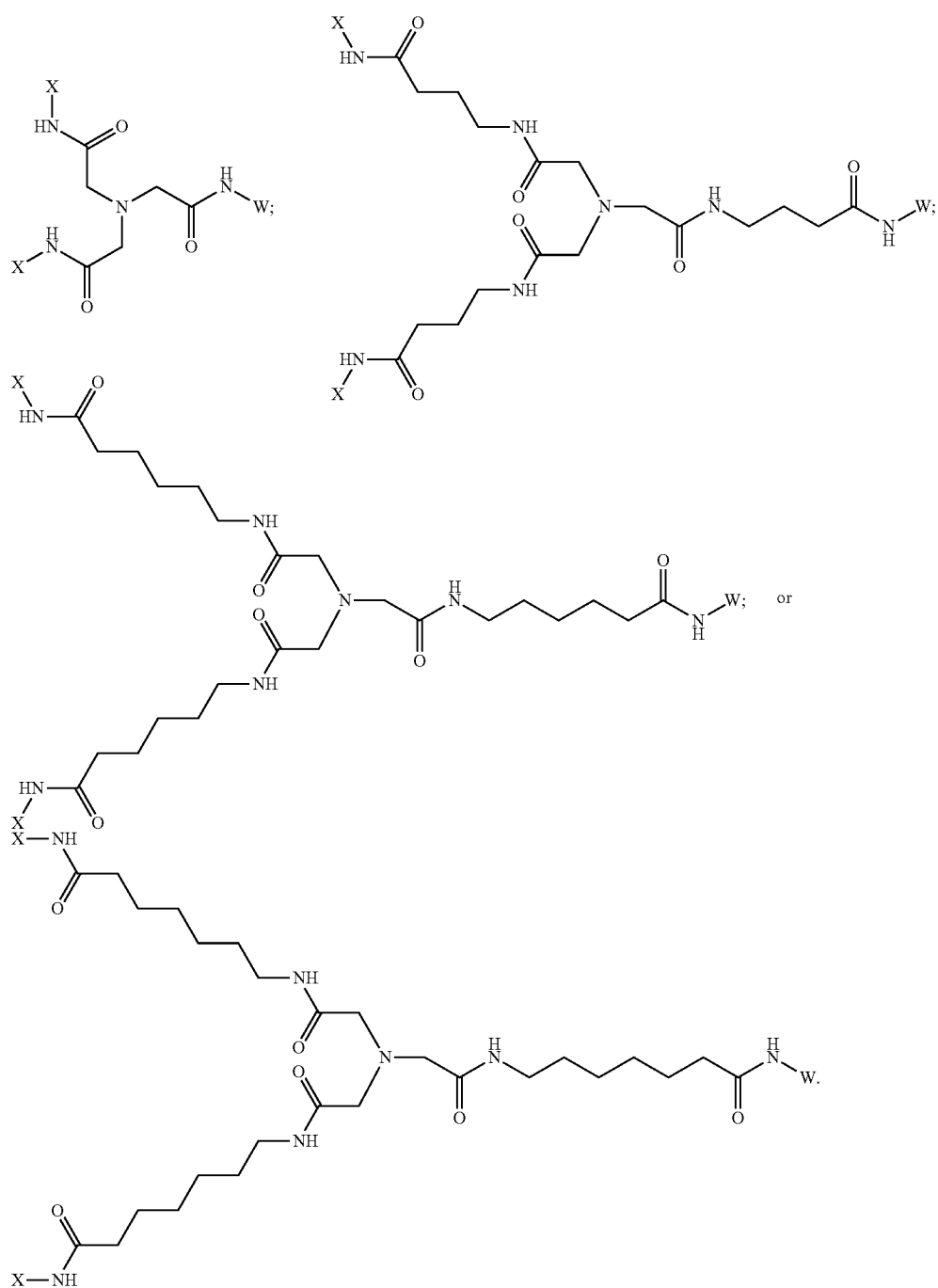
In some embodiments, the present disclosure provides conjugates of general formula (II-a3):
For example, in some embodiments, the present disclosure provides conjugates of formula:
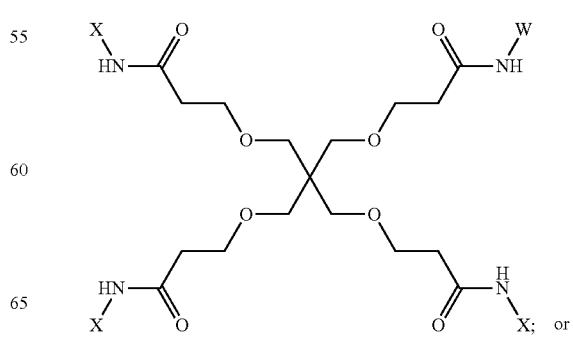

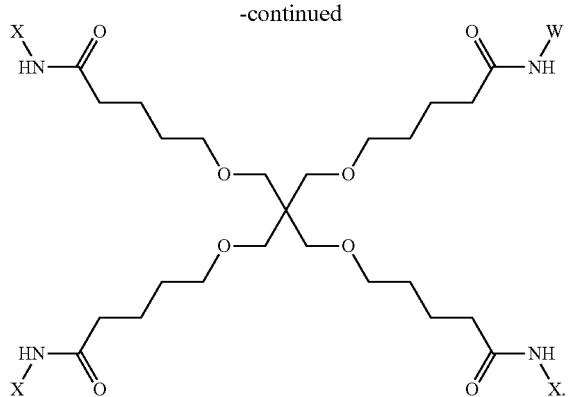

Characterization of Conjugates

The conjugates can be characterized by any analytical method including nuclear magnetic resonance (e.g., $^1$H NMR); gel permeation chromatography (GPC) for molecular weight and polydispersity; Fourier transform infrared spectroscopy (FTIR), etc.

In certain embodiments the conjugate framework (i.e., without including the affinity ligands, drug or detectable label) has a molecular weight of less than 10,000 Da, e.g., in the range of about 100 to about 10,000 Da. In certain embodiments, the conjugate framework has a molecular weight in the range of about 300 to about 5,000 Da. In certain embodiments, the conjugate framework has a molecular weight in the range of about 500 to about 2,500 Da. In certain embodiments, the conjugate framework has a molecular weight in the range of about 1,000 to 2,000 Da. In certain embodiments, the conjugate framework has a molecular weight in the range of about 200 to 1,000 Da. In certain embodiments, the conjugate framework has a molecular weight in the range of about 300 to 800 Da.

Other Embodiments

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A cross-linked material comprising:
   (a) multivalent polynucleotide aptamers that bind glucose, wherein the multivalent aptamers comprise
      (i) at least 40 contiguous nucleotides that are 90% identical to nucleotides 20-59 of SEQ ID NO: 2, 3, 5, or 7;
      (ii) nucleotides 20-59 of SEQ ID NO: 4 or 6; or
      (iii) nucleotides 20-45 of SEQ ID NO: 1; and
   (b) conjugates that include two or more separate affinity ligands bound to a conjugate framework, and wherein the two or more affinity ligands compete with a target molecule for binding with the aptamers and wherein the conjugates are cross-linked within the material as a result of non-covalent interactions between aptamers and affinity ligands on different conjugates.

2. The material of claim 1, wherein the conjugates further comprise a drug bound to the framework.

3. The material of claim 1, wherein the target molecule is glucose.

4. The material of claim 3, wherein the affinity ligands of the conjugates include a saccharide.

5. The material of claim 2, wherein the drug is an antidiabetic drug.

6. The material of claim 2, wherein the drug is an insulin molecule.

7. The material of claim 2, wherein the at least one conjugate includes a structure of formula:

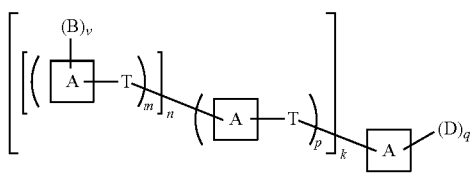

II wherein:

each occurrence of [(A-T)] represents a potential branch within the at least one conjugate;

each occurrence of (A-T) represents a potential repeat within a branch of the at least one conjugate;

each occurrence of A is independently a covalent bond, a carbon atom, a heteroatom, or an optionally substituted group selected from the group consisting of acyl, aliphatic, heteroaliphatic, aryl, heteroaryl, and heterocyclic;

each occurrence of T is independently a covalent bond or a bivalent, straight or branched, saturated or unsaturated, optionally substituted $C_{1-30}$ hydrocarbon chain wherein one or more methylene units of T are optionally and independently replaced by —O—, —S—, —N(R)—, —C(O)—, —C(O)O—, —OC(O)—, —N(R)C(O)—, —C(O)N(R)—, —S(O)—, —S(O)$_2$—, —N(R)SO$_2$—, —SO$_2$N(R)—, a heterocyclic group, an aryl group, or a heteroaryl group;

each occurrence of R is independently hydrogen, a suitable protecting group, or an acyl moiety, arylalkyl moiety, aliphatic moiety, aryl moiety, heteroaryl moiety, or heteroaliphatic moiety;

—B is -T-$L^B$-X;

each occurrence of X is independently an affinity ligand selected from the group consisting of aminoethylglucose (AEG), aminoethylmannose (AEM), aminoethylbimannose (AEBM) and aminoethyltrimannose (AETM);

each occurrence of $L^B$ is independently a covalent bond or a group derived from the covalent conjugation of a T with an X;

-D is -T-$L^D$-W;

each occurrence of W is independently a drug or a detectable label;

each occurrence of $L^D$ is independently a covalent bond or a group derived from the covalent conjugation of a T with a W;

k is an integer from 2 to 11, inclusive, defining at least two k-branches within the conjugate;

q is an integer from 1 to 4, inclusive;

k+q is an integer from 3 to 12, inclusive;

each occurrence of p is independently an integer from 1 to 5, inclusive; and each occurrence of n is independently an integer from 0 to 5, inclusive; and each occurrence of m is independently an integer from 1 to 5, inclusive; and each occurrence of v is independently an integer from 0 to 5, inclusive, with the proviso that within each k-branch at least one occurrence of n is ≥1 and at least one occurrence of v is ≥1.

8. The material of claim 7, wherein at least two occurrences of X include an affinity ligand that comprises a saccharide.

9. The material of claim 7, wherein at least two occurrences of X include an affinity ligand that comprises a bimmanose or a trimannose.

10. A method comprising administering a material of claim 2 to a patient.

11. The method of claim 10, wherein the patient is diabetic.

* * * * *